(12) United States Patent
Vleugels

(10) Patent No.: US 12,205,504 B2
(45) Date of Patent: Jan. 21, 2025

(54) AUTOMATED VISION CARE DIAGNOSTICS AND DIGITALLY COMPENSATED SMART EYEWEAR

(71) Applicant: Roka Labs, Inc., Austin, TX (US)

(72) Inventor: Katelijn Vleugels, Austin, TX (US)

(73) Assignee: Roka Labs, Inc., Austin, TX (US)

( * ) Notice: Subject to any disclaimer, the term of this patent is extended or adjusted under 35 U.S.C. 154(b) by 680 days.

(21) Appl. No.: 17/404,802

(22) Filed: Aug. 17, 2021

(65) Prior Publication Data

US 2022/0058999 A1 Feb. 24, 2022

Related U.S. Application Data

(60) Provisional application No. 63/067,182, filed on Aug. 18, 2020.

(51) Int. Cl.
*A61B 3/12* (2006.01)
*A61B 3/14* (2006.01)
*G06F 3/01* (2006.01)
*G09G 3/02* (2006.01)

(52) U.S. Cl.
CPC .............. *G09G 3/02* (2013.01); *A61B 3/12* (2013.01); *A61B 3/14* (2013.01); *G06F 3/015* (2013.01); *G09G 2380/08* (2013.01)

(58) Field of Classification Search
CPC ........ G09G 3/02; G09G 2380/08; A61B 3/00; A61B 3/12; A61B 3/14; G06F 3/015
See application file for complete search history.

(56) References Cited

U.S. PATENT DOCUMENTS

| 9,852,496 | B2 | 12/2017 | Marchand et al. |
| 10,409,068 | B1 | 9/2019 | Wiemer et al. |
| 10,459,255 | B2 | 10/2019 | Tuan et al. |
| 10,649,239 | B2 | 5/2020 | Kneiss et al. |
| 2003/0028115 | A1 | 2/2003 | Thomas |
| 2010/0110379 | A1* | 5/2010 | Zhou ..................... A61B 3/103 351/205 |

(Continued)

OTHER PUBLICATIONS https://digitalnature.slis.tsukuba.ac.jp/wp-content/uploads/2018/06/2018-siggraph-retinal.pdf.

(Continued)

*Primary Examiner* — Abdullahi Nur
(74) *Attorney, Agent, or Firm* — Prince Lobel Tye LLP

(57) ABSTRACT

Systems and methods for implementing digital vision diagnostics are described and can include: (1) projecting images onto an individual's retina; (2) modelling the optics of the retina; (3) collecting user input/feedback in response to the projected image(s); (4) collecting other known vision-related data or contextual metadata; (5) diagnosing at least one vision-related or diagnostic parameter of the individual based on a combination of (1)-(4). Systems and methods for implementing digital vision compensation are further described and can include: (1) digitally capturing image(s) of an individual's field-of-view or portion thereof, or retrieving pre-recorded image(s); (2) determining or retrieving at least one vision-related or diagnostic parameter of the individual (e.g., using digital vision diagnostic technique(s)); (3) process the captured or pre-recorded digital image(s) to create compensated digital image(s); and (4) display or project the compensated digital image(s) to the individual.

29 Claims, 21 Drawing Sheets

(56) References Cited

U.S. PATENT DOCUMENTS

| | | | |
|---|---|---|---|
| 2010/0149073 A1* | 6/2010 | Chaum | G02B 27/0075 |
| | | | 345/8 |
| 2011/0317751 A1* | 12/2011 | Roethig | H04L 25/03885 |
| | | | 375/232 |
| 2012/0194781 A1* | 8/2012 | Agurok | A61B 3/113 |
| | | | 351/201 |
| 2013/0120390 A1* | 5/2013 | Marchand | G06T 5/80 |
| | | | 345/428 |
| 2017/0316609 A1* | 11/2017 | Dunn | G06F 3/013 |
| 2019/0223716 A1 | 7/2019 | Abou Shousha et al. | |

OTHER PUBLICATIONS https://www.cnet.com/news/how-google-glass-works-now-and-tomorrow.

https://www.d-eyecare.com.

Alonso, Jr. et al., "Image pre-compensation to facilitate computer access for users with refractive errors," Behaviour and Information Technology 24(3): 161-173, May 2005.

International Search Report and Written Opinion of the International Searching Authority for counterpart PCT/US2021/046345, mailed on Nov. 11, 2021.

* cited by examiner

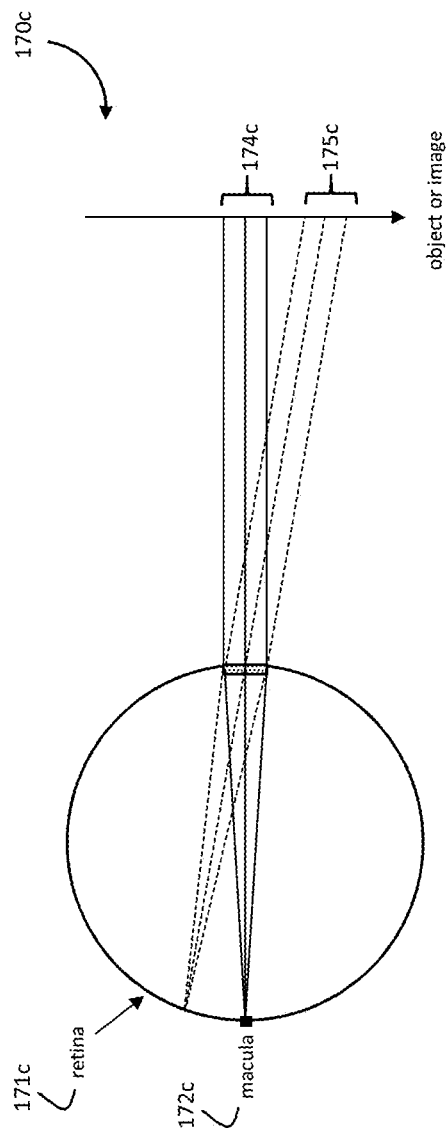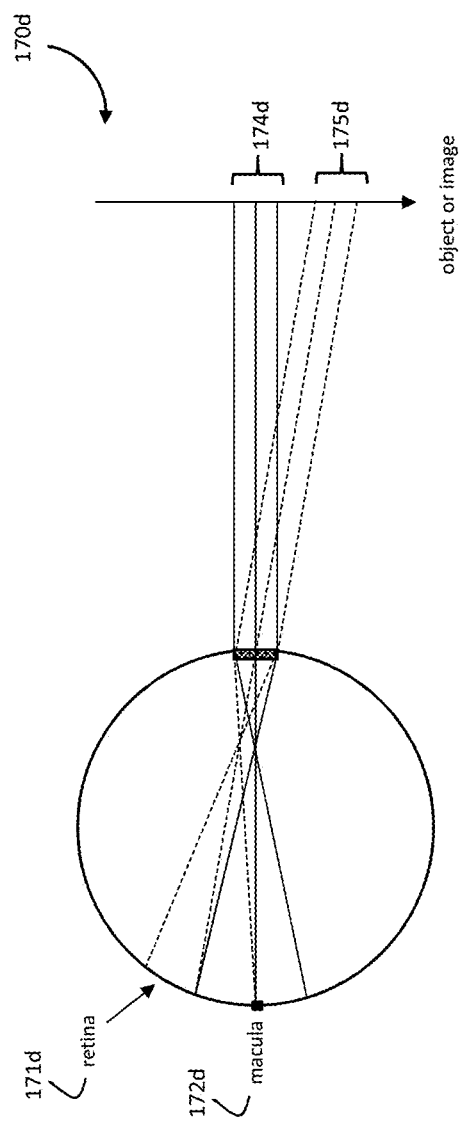
FIG. 1C
FIG. 1D

AUTOMATED VISION CARE DIAGNOSTICS AND DIGITALLY COMPENSATED SMART EYEWEAR

CROSS-REFERENCE TO RELATED APPLICATIONS

This application claims priority to and the benefit of U.S. Provisional Patent Application No. 63/067,182, filed on Aug. 18, 2020, the contents of which is hereby incorporated by reference in its entirety.

BACKGROUND

Today, eye exams are being performed by optometrists and ophthalmologists who use expensive vision diagnostics equipment such as phoropters, ophthalmoscopes, autorefractors, etc. to determine an individual's vision problems such as refractive errors, vision impairments and other problems.

A refractive error is a problem of focusing light directly on the retina of the eye due to the shape of the eye. The most common types of refractive error are near-sightedness (or myopia), far-sightedness (or hyperopia), astigmatism, and presbyopia. Near-sightedness is due to the length of the eyeball being too long, far-sightedness is due to the length of the eyeball being too short, astigmatism is due to the cornea being the wrong shape, and presbyopia is due to the aging of the lens of the eye such that it cannot change shape sufficiently. The number of people globally with refractive errors has been estimated at one to two billion.

A vision impairment refers to macular degeneration, retinopathy, retinitis pigmentosa, glaucoma, or other impairments caused by damage of one or more portions of the retina. Vision problems may also refer to difficulty seeing in the dark (e.g. night blindness), difficulty transitioning from a light to a dark setting, or difficulty distinguishing between colors. Other examples of vision problems are known in the art.

To date, physical lenses have been used to compensate for refractive errors. Physical test lenses are used in diagnostic eye exams to determine the power of a patient's lens prescription. People then wear corrective physical lenses, in the form of prescription glasses or contact lenses that have been selected based on the test lenses used in the eye exam, to correct for refractive errors. The cost of diagnostic equipment, and of manufacturing custom prescription lenses, are high.

It also takes a lot of time to both schedule/conduct eye exams, and then manufacture the corrective lenses. For example, in order to obtain prescription eyewear, an individual needs to undergo a refraction test that allows the optometrist to approximate the individual's lens prescription that comes closest to giving the individual ideal (i.e., 20/20 vision). One eye at a time, the optometrist may change out the lenses in the phoropter and ask the individual each time which lens is clearer. Based on the individual's answers, the optometrist comes up with the best combination and determines the individual's prescription for eyeglasses or contact lenses. Alternatively, or in addition, an optometrist may use an autorefractor to measure how light changes as it propagates through the eye and reflects on the back of the eye. From several readings, obtained by moving a picture in and out of focus, the autorefractor can compute the parameters for an individual's eyewear prescription.

Software-based image processing methods have been proposed to help enhance the vision of a user with a vision problem, for example, by rendering images that have been compensated for the individual's vision error or visual impairment (Alonso et al., Marchand et al., Tuan et al.). However, such methods require as an input some quantification or approximation of the individual's vision problem, which is not always available. Today, such inputs usually need to be obtained through traditional eye exam methods as described above, which are expensive and time-consuming.

Software-based vision care diagnostics methods that can eliminate the need for an expensive, in-person eye exam with an eye doctor or other vision care practitioner (e.g., optometrist or ophthalmologist) are thus desirable. Such software-based vision care diagnostics methods would make it possible to diagnose a vision problem such as a refractive error or vision impairment, and/or to determine a parameter that characterizes such a vision problem such as for example a parameter of an eyewear prescription, a localization of retinal damage, or a gradation of night blindness. Moreover, such software-based vision care diagnostics methods could be performed at any location and at any time, provided the individual being tested has access to a commonplace handheld computing device such as a mobile phone, tablet or computer.

Individuals with vision problems make use of vision aid devices to access analog visual information (i.e., visual information that can be processed by individuals to enable them to observe and interact with the world around them, such as the information gathered by an individual driving a car, regarding what obstacles lie on a road ahead of his or her moving vehicle). To correct refractive errors such as near-sightedness, farsightedness, presbyopia, or astigmatism, an individual may wear prescription glasses or contact lenses. Such traditional corrective devices use optical lenses to optically adjust the focus of an incoming light beam before it reaches an individual's retina, which means they) need to be custom made for each individual, which in turn drives up time and money cost as described above.

Furthermore, for strong prescriptions, optical lenses can become thick, making them non-discreet to wear, or even impractical to manufacture.

In certain circumstances, an individual may desire or be obligated to wear protective eyewear such as sunglasses, swim goggles, ski goggles, or safety glasses that tend to be mass-produced and non-corrective. In these circumstances, an individual with vision problems needs to wear prescription glasses or contact lenses underneath the protective eyewear, which can be inconvenient or impractical. In some cases, the individual can order custom built prescription protective eyewear, but again, such eyewear is typically costly as described above.

Another problem for someone with vision problems such as farsightedness or presbyopia for example, is that it may be easy to forget to always bring along his/her prescription/reading glasses or contact lenses. It is therefore desirable to have digital, software-based refractive error correction functionality integrated in common multi-functional electronic devices such as smart phones or smart watches that are less likely to be forgotten.

With the proliferation of connected or "smart" devices, and the anticipated emergence of Augmented Reality ("A/R") and Virtual Reality ("V/R") interfaces over the coming years, it would be desirable to leverage those platforms and integrate digital, software-based refractive error correction methods. This would end reliance on the traditional optical methods, which suffer from the deficiencies outlined above.

U.S. Pat. No. 10,459,255 to Tuan et al. (hereinafter Tuan) describes an eye-mounted display to enhance vision for individuals with eye problems that cannot be corrected with optical glasses or contact lenses. More specifically, Tuan proposes compensation methods such as magnification of a captured image, compression of the angular extent of a captured image, enhancement of the contrast of a captured image, or overlaying of identification information over a captured image. While such methods may be beneficial for individuals with severe vision impairments due to retinal damage or night blindness, for example, the methods proposed by Tuan are not suitable when correcting for refractive errors because they do not substantially match the functionality provided by optical solutions (such as optical glasses or contact lenses). Furthermore, eye-mounted displays as proposed by Tuan may not be desirable for certain individuals as they can cause irritations of the eye and require frequent maintenance and charging.

"Image pre-compensation to facilitate computer access for users with refractive errors," Alonso Jr. et al., Behaviour and Information Technology 24(3):161-173, May 2005 (hereinafter Alonso Jr.) and U.S. Pat. No. 9,852,496 to Marchand et al. (hereinafter Marchand) both propose digital pre-compensation methods to compensate for refractive errors. However, the methods proposed by Alonso Jr. and Marchand are aimed at facilitating computer access for consumption of digital content. Their methods do not address how individuals with refractive errors can access analog visual information to enable them to observe and interact with the world around them.

SUMMARY

Aspects and embodiments of the present invention are generally directed to systems and methods for determining optical information associated with vision. One such set of embodiments describes a method for passively determining optical information associated with vision including the steps of: obtaining a digital reference image; projecting the digital reference image from a first image plane via a first optical axis, on to a retina; receiving a reflected image from the retina via a second optical axis, at a second image plane; recording a digital representation of the reflected image; modeling using an optical transfer function comprising one or more optical parameters, the optics between the first image plane and the retina along the first optical axis, the optics associated with absorption or reflection of light at the retina, and the optics between the retina and the second image plane along the second optical axis; and comparing the digital reference image to the digital representation of the reflected image, to calculate an error value for one of the optical parameters.

Another set of embodiments describes another method for passively determining optical information associated with the vision of a person including the steps of: obtaining a digital reference image; projecting the digital reference image from a first image plane via a first optical axis, on to a retina; recording a digital representation of the neurological image sensed by the person via at least one brain-computer interface, wherein the neurological image is associated with one or more nerve signals received by the light-sensing nerve cells when that person's retina detects the digital reference image; modeling using an optical transfer function comprising one or more optical parameters, the optics between the first image plane and the retina along the first optical axis; and comparing the digital reference image to the digital representation of the neurological image to calculate an error value for one of the optical parameters.

Further aspects and embodiments of the present invention are generally directed to systems and methods for providing adaptive electronic vision compensation. One such set of embodiments describes an adaptive electronic eyewear system including an image display component configured to display images within a field of view of an individual; at least one processor communicatively coupled to the image display component and configured to: receive an optical parameter associated with a vision problem of a person; calculate an inverse optical transfer function based on the optical parameter; create a pre-compensated image by using the inverse optical transfer function; and cause the image display component to display the pre-compensated image.

Still other aspects, embodiments, implementations, and advantages of these examples are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment in any manner consistent with at least one of the objectives, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIG. 1C is a diagram illustrating aspects and embodiments of an eye that is functioning without a refractive error;

FIG. 1D is a diagram illustrating aspects and embodiments of an eye exhibiting nearsightedness;

DETAILED DESCRIPTION

Figure 1A:
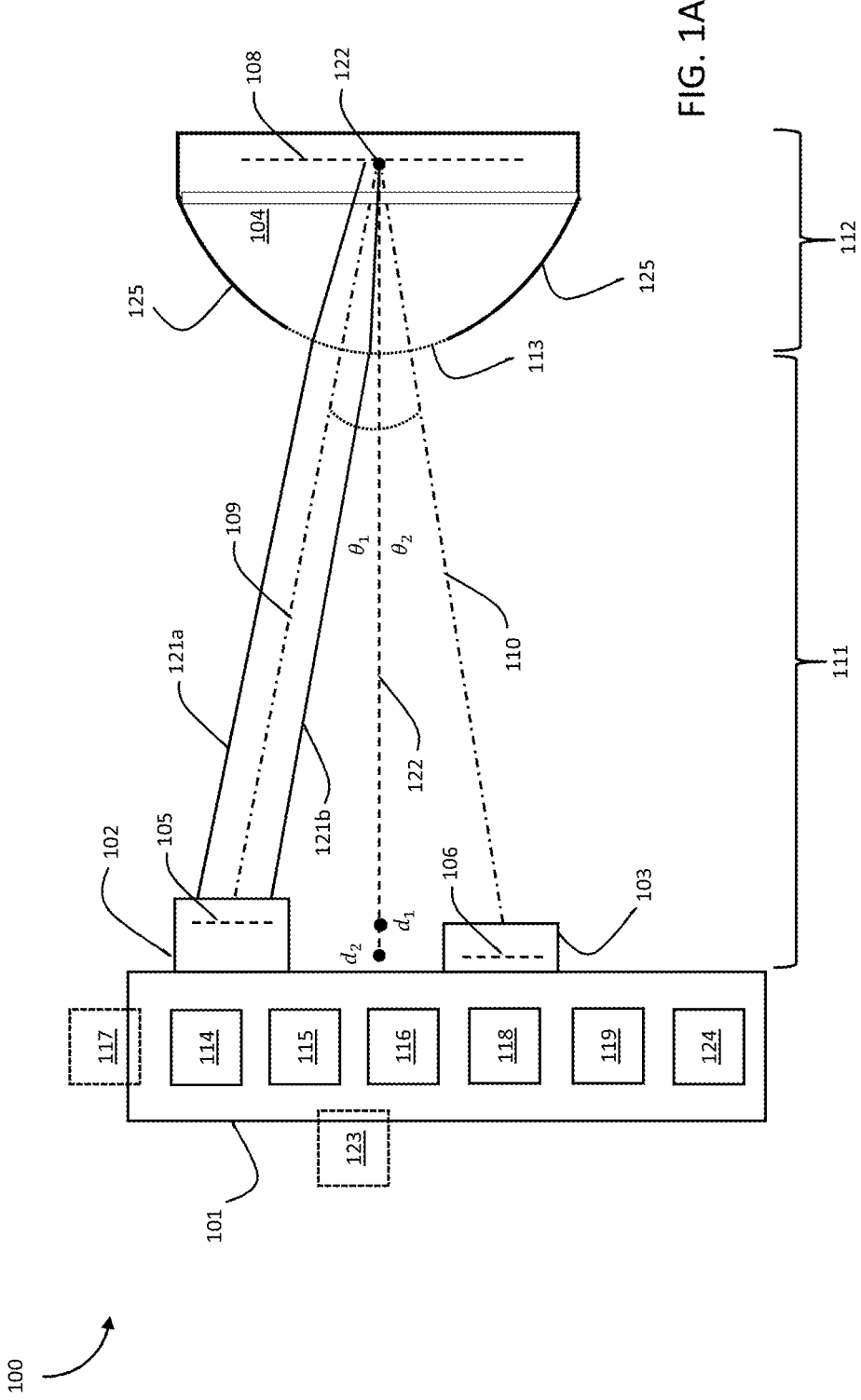
FIG. 1A is a diagram illustrating aspects and embodiments of a system for providing automated vision care diagnostics.

The following description is merely exemplary in nature and is not intended to limit the present disclosure, application, or uses. It should be understood that, throughout the drawings, corresponding reference numerals indicate like or corresponding parts and features.

Various embodiments and implementations of the present invention provide systems and methods for diagnosing and/or compensating for a user's vision problems. Vision problems may include refractive errors, vision impairment, vision loss, and other known types of vision issues.

In embodiments relating to diagnosing vision problems, the systems and methods described herein may include hardware and/or software capable of projecting, capturing, recording, and digitally processing images and other analog signals to facilitate, in response to images projected onto or displayed to the user's retina, the collection of data relating to those vision problems. The data can either be actively provided by the individual/user being diagnosed as she communicates the quality of the images she is detecting, or passively provided by observing the images formed at the retina, as the light beams/rays that form those images arrive at the individual's retina. Said systems and methods may further comprise the receipt of inputs from a user, or the retrieval of inputs from memory, which inputs indicate that user's degree or type of vision problem.

The invention further includes techniques for generating one or more prescription parameters (e.g., for glasses or contact lenses) based on the data relating to vision problems that are collected by the systems and methods described herein. Using those prescription parameters, an image or series of images can be processed by a signal processing unit based on previously collected data about a given individual's vision problems to change or manipulate the light sent to that individual's retina by altering, for example, the optical focus of those images when projected onto that given individual's retina. The signal processing unit processes the image or series of images using data about that given individual's vision problems such that when the processed image or series of images is projected onto the individual's retina, after propagation through other parts of the individual's eye such as the lens, it has a different focus as compared to the optical focus of an unprocessed version of that image that is projected onto that given individual's retina. The images that have been processed as such are tailored for that given individual and may be perceived as out-of-focus if presented to another individual that has no vision problems or has vision problems that are different than those of the given individual. Note that the degree to which said processed image(s) would appear out-of-focus to an individual with a healthy eye or a different vision problem, will depend upon the relative severity of the vision problem being compensated for. In some cases, for example when compensating for an individual with a significant refractive error problem, the processed images will appear obviously out-of-focus to an individual with a healthy eye.

FIG. 1A is a diagram illustrating a system 100 for providing automated vision care diagnostics according to various embodiments of the present invention. It also illustrates an individual's eye 104. The system 100 includes an electronic device 101, which could be for example a mobile phone, a tablet, or smart eyewear including smart glasses, smart contact lenses, A/R eyewear, V/R eyewear or smart goggles. The electronic device 101 may also be a game console, a watch or any other wearable, a medical device, a piece of diagnostic vision equipment, a smart windshield, or a smart window. The electronic device 101 includes at least one processor 114, and may include at least one memory subsystem 115 for volatile data retention and/or at least one storage subsystem 116 for persistent storage retention. The electronic device 101 may also run one or more operating systems, drivers, firmware, and/or application programs. The electronic device 101 may further include an image projection module 102 capable of electronically projecting reference images from a first digital reference image plane 105, onto the cornea 113 (as distinct from the other parts of the eyeball 125 surface, such as the sclera) of the individual's eye 104, for eventual processing at the individual's retinal image plane 108 using the internal mechanisms of the eye. For example, the image projection module 102 may include an LCD, LED, DLP image projector, retinal projector (e.g., a virtual retinal display) or femtoprojector and, associated processing circuitry and/or device-level software. In some embodiments, the image projection module 102 may comprise one or more light source(s) and/or array(s) of light sources (e.g., one or more LEDs) configured to project digital images onto an image plane (e.g., a reflective screen or backlit display) positioned within the field of view of the individual's eye. In other embodiments, the image projection module 102 may alternately or additionally comprise one or more light source(s) and/or array(s) of light sources configured to project digital images directly onto the individual's eye 104 (e.g., via one or more femtoprojector(s)). Said light source or video projector may be communicatively coupled to said associated processing circuitry.

The electronic device 101 may further include an image capture module 103 capable of electronically capturing and/or recording images received at a second image plane 106, which images are based on those being processed at the retinal image plane 108. For example, the image capture module 103 may include a digital camera and associated image processing circuitry and/or device-level software, image sensors, wavefront sensors, charge-coupled device (CCD) image sensor, and CMOS sensors. The image projection module 102 and image capture module 103 may each also include at least one dedicated processor, memory subsystem and/or storage subsystem (not illustrated).

The system 100 may optionally include at least one neural sensor module 117 communicatively coupled to the electronic device 101. The neural sensor module 117 comprises one or more neural sensors capable of collecting neural information from the individual undergoing examination. The neural sensor module 117 may be internal to the electronic device 101, external to the electronic device 101, or partially external to the electronic device 101 (e.g., mounted as an attachment). In some implementations, some portions of the neural sensor module 117 may be internal to the electronic device 101 (e.g., signal processing circuitry), while others may be external (e.g., neural sensors). The neural sensor module 117 may include at least one dedicated processor, memory subsystem, and/or storage subsystem. In some cases, the neural sensor module 117 may further include additional processing circuitry and/or device-level software.

The electronic device 101 may optionally include at least one user interface 118 for accepting user input. The electronic device 101 may optionally include at least one wired or wireless communications interface 119 for communicating with local and remote networks (e.g., a Wi-Fi or Ethernet interface capable of accessing remote servers via the Internet).

In at least one embodiment of the present invention, the system 100 is operable to diagnose a vision problem of an individual undergoing an eye examination. The electronic device 101 is positioned in the field of view of an individual's eye 104. The image projection module 102 is programmed to project at least one digital reference image ("DRI") onto the cornea 113 of the individual's eye 104 along a first optical axis 109. Preferably, the optical axis 109 of the image projection module 102 is aligned to match or substantially match the central axis 122 of the individual's field of view. Such a DRI is received at the cornea 113 of the individual's eye 104 and relayed onto a retinal image plane 108 corresponding to an image that is received and processed by the retina (not shown) of the eye 104. The retinal image plane 108 further includes a central portion 122 that includes the macula portion of the retina, which contains the highest concentration of light-sensitive neurons and corresponds to the central portion of an individual's field of view. The DRI is projected across an external optical channel 111, and then from the cornea 113 to the retinal image plane 108 via an internal optical channel 112 within the eye.

In certain embodiments, the image projection module 102 can be configured to project at least one pre-compensated digital reference image ("PCDRI") that has been modified based on one or more vision-related parameter(s) or contextual metadata. Said vision-related parameters and contextual metadata may be locally stored on electronic device 101 and may be received or determined based on data previously or currently being collected by the image capture module 103, neural sensor module 117, user interface 118, or communications interface 119.

Contextual metadata may include one or more of the following: a distance between a display and/or camera and an eye, an individual's pupil size, display parameters (for example, but not limited to, resolution, size, luminance), and an ambient light level (e.g. room illuminance). Additional ancillary sensor inputs may be used to calculate one or more contextual metadata inputs. Ancillary sensors may include but are not limited to one or more of the following: camera, ambient light sensor, speaker, microphone, motion sensor (e.g. accelerometer, gyroscope, magnetometer), or vital sign sensor (e.g. blood pressure sensor, heart rate sensor, body temperature sensor). In addition to or instead of ancillary sensor inputs, an individual's personal information may also be used to provide one or more contextual metadata. Personal information may among other information include one or more of the following: age, gender, medical history (e.g. smoking, diabetes, retinopathy, glycemic control), current or historical activity or behavior information (e.g. physical activity, sleep patterns, stress). For example, typical pupil diameters for an eye in total darkness, and pupil size changes in lit situations, vary with age. An individual's age can therefore be used in the calculation or estimation of said individual's pupil size. In another example, typical pupil diameters reduce when ambient light level increases. It may therefore be possible to calculate an individual's pupil size from said individual's pupil size at a known ambient level and a measurement of the current ambient light level.

In response to the DRI or PCDRI projected by image projection module 102, a reflected retinal image ("RRI") is reflected back out of the individual's eye towards the electronic device 101. The image capture module 103 is configured to receive the RRI along a second optical axis 110 and capture and/or record the RRI at a second image plane 106. The neural sensor module 117 may also be configured to measure one or more neural signals of the individual before, during, and after the DRI or PCDRI is being viewed by the individual's eye. The one or more user interfaces 118 may also be configured to collect user input/feedback before, during, or after the DRI or PCDRI is being viewed by the individual. The one or more communications interfaces 119 may further be configured to collect vision-related data or contextual metadata before, during, or after the DRI or PCDRI is being viewed by the individual's eye.

In certain embodiments, the electronic device 101 further includes an outward sensor unit 123 (e.g., an outward-facing camera) configured to capture image(s) or image parameter(s) falling within the individual's field of view. For example, the electronic device 101 may include a smartphone or smart eyewear, and outward sensor unit 123 may include a camera configured to capture and digitize images falling within the individual's field of view. The electronic device may further include a signal processing unit 124 (which may include a combination of hardware and/or software) configured to process images or image parameters received by the outward sensor unit 123. Said processed images or image parameters may further be used to generate a DRI or PCDRI that displays a compensated version of the image(s) captured by outward sensor unit 123. In some embodiments, such processing may be performed in real-time or near real-time. For example, the outward sensor unit 123 may capture an image falling within the individual's field of view, the signal processing unit 124 may process this image and use the processed image to generate a DRI/PCDRI, and the image projection module 102 may project the DRI/PCDRI onto the individual's retinal image plane 108 such that the projected image appears differently to the individual than the analog contents of the individual's field of view would appear without any visual compensation mechanism.

The individual's eye 104 can be modeled as a Linear Shift-Invariant ("LSI") system described by its pupil function ("PF"), or by its optical transfer function ("OTF") and point spread function ("PSF"). The eye's PF describes how incident light waves are affected upon transmission through the eye 104 and captures optical aberrations that occur between the cornea 113 and the retinal image plane 108. The PF may be expressed according to the following equation:

$$PF(\rho,\theta)=A(\rho,\theta)e^{ikW(\rho,\theta)} \quad \text{(Eq. 1)}$$

where $\rho$ and $\theta$ are the polar coordinates in the pupil, and $W(\rho,\theta)$ is the wavefront aberration function, $A(\rho,\theta)$ is the amplitude function describing the relative efficiency of light passing through the pupil, $i=\sqrt{-1}$, and $k=2\pi/\lambda$ where $\lambda$ is the wavelength, and $\rho$ and $\theta$ are the polar coordinates in the pupil. $W(\rho,\theta)$ is a function of the individual's vision error and of the contextual metadata (e.g. pupil size, distance between reference image plane and eye, wavelength $\lambda$).

The OTF, which specifies how different spatial frequencies are handled by the eye, can be derived as the autocorrelation of the PF. The PSF, which describes the response of the eye to a point source, can be calculated as the inverse Fourier Transform of the OTF and the square absolute of the inverse Fourier transformed PF.

The wavefront aberration function $W(x,y)$ represents the deviation of the light wavefront from a purely spherical pattern as it passes through the optical elements of the eye and can be modeled as a Zernike polynomial series. For example, in case of a second-order aberration like myopia or hyperopia, the aberration can be modeled as a Zernike polynomial $Z_0^0$ with second-order radial mode and zeroth-order meridional frequency, and the PF could be represented by the following equation:

$$PF(\rho,\theta)=A(\rho,\theta)e^{ik(\beta*(2\rho^2-1))} \quad \text{(Eq. 2)}$$

where $\beta$ is the fitting coefficient expressing the wavefront errors in wavelengths, and a function of the severity of myopic/hyperopic vision error. $\beta$ can be calculated from a physical lens arameters such as the lens power (aka sphere or strength).

To fully capture the Bidirectional Optical Transfer Function ("BOTF") of the optical path traversed by an incoming and reflected light wave, one further needs to consider absorption/reflection at the retinal plane and account for the fact that the light wave traverses the optical elements of the system (including the eye) twice: once on the optical path into the retina, along a first optical axis 109, and once (with respect to the reflected image) on the optical path out, along a second optical axis 110. The relationship between the DRI and the recorded RRI can then be expressed as follows:

$$RRI=BOTF(DRI) \quad \text{(Eq. 3)}$$

In some embodiments of the present invention, the incoming optical path may differ from the outgoing optical path. For example, as shown in FIG. 1A, an incoming optical path associated with the projected DRI can follow a first optical axis 109 aligning the center of the first image plane 105 with the center of the individual's eye 104. An outgoing optical path associated with the captured RRI can follow a second optical axis 110 aligning the center of the individual's eye 104 with the center of the second image plane 106. Distance parameters d1 and d2 refer to the distance between the center of the individual's eye 104 and the first and second image planes 105 and 106, respectively. Angular offset parameters $\theta_1$ and $\theta_2$ refer to the angular offset of the first and second optical axis 109 and 110, respectively, relative to the central axis of the individual's field of view. The system may be configured to calculate a delta between the first and second optical axis. In some embodiments, the system may determine and/or use the distance parameters and/or angular offset parameters to calculate the delta between the first and second optical axis.

In various embodiments of the system 100, the RRI (or one or more parameters associated with the RRI) may be modified to compensate for an angular offset between the first optical axis and the second optical axis, or to compensate for an offset between the distance (e.g., $d_1$) from the individual's eye to the first image plane 105, versus the distance from the individual's eye to the second image plane 106 (e.g., $d_2$). In certain embodiments of the system 100, the OTF, PSF, PF, BOTF, and/or their respective inverse functions (or one or more parameters associated therewith) may alternately or additionally be adjusted to compensate for such angular offsets or distance offsets.

The system 100 further illustrates how rays of incident light (e.g., 121a and 121b) produced by the image projection module 102 travel along the first optical axis 109 and interact with an individual's eye 104 within the internal optical channel 112. As is further illustrated by way of example in FIG. 1C, in a healthy eye, incoming incident light at or near the central portion of an individual's field of view (e.g., 121b) is focused by the optics (meaning the absorption, transmission and/or deflection behaviors, characteristics and/or properties exhibited by light) of the internal optical channel 112 causing the incoming incident light to converge at or substantially at the central portion 122 of the retinal image plane 108. Similarly, in a healthy eye, incoming incident light closer to the periphery of the individual's field of view is focused by the optics of the internal optical channel 112 causing the incoming incident light to converge at the retinal image plane 108. However, as is further illustrated by way of example in FIG. 1D, the eye of an individual experiencing nearsightedness is unable to properly focus incoming incident light causing the light to converge inside the internal optical channel 112 before reaching the retinal image plane 108.

The optics of the internal optical channel 112 can be modelled by the OTF, PSF, PF, and/or incoming portion of the BOTF as discussed above. Although not shown, outgoing rays of light corresponding to the RRI travel along the second optical axis 110 and similarly interact with the internal optical channel 112 of the individual's eye. The outgoing optics within the internal optical channel 112 can be modelled by the inverse OTF, inverse PSF, inverse PF, and/or outgoing portion of the BOTF. In various embodiments of the system 100, the optics of the external optical channel 111 can be modelled using an amplitude function (e.g., an equation mapping amplitude loss of incident light as function of distance from the first image plane 105 or the cornea 113). The behavior of the external optical channel 111 may further be included in the OTF, PSF, PF, inverse functions thereof, and/or the BOTF, so that said function(s) account for the optics of both the external optical channel 111 and the internal optical channel 112.

Thus, the OTF, PSF, PF, and/or incoming portion of the BOTF can be used to model the incoming optics between the first image plane 105 and the retinal image plane 108. Similarly, the inverse OTF, inverse PSF, inverse PF, and/or outgoing portion of the BOTF can be used to model the outgoing optics between the retinal image plane 108 and the second image plane 106. Accordingly, since the BOTF models both the incoming and outgoing optics of the external optical channel 111 and the internal optical channel 112, the BOTF can be used to model an expected RRI received at the second image plane 106 based on a DRI/PCDRI projected from the first image plane 105.

In various embodiments, the OTF, PSF, PF, BOTF, their respective inverse functions, and/or respective optical parameters within these functions may be modified to account for a known or suspected vision problem of the individual. In various embodiments, a DRI, PCDRI, and/or respective image parameters within these images may be alternately or additionally modified to account for a known or suspected vision problem of the individual. In embodiments including outward sensor module 123, said modifications to the above optical function(s) or DRI/PCDRI(s) may be configured to cause image projection module 102 to project an image onto the individual's retinal image plane 108 that appears differently to the individual relative to the analog contents of their field of view (without using any compensation).

For example, considering an individual with nearsightedness, the electronic device 101 may use outward sensor module 123 to capture an image falling within the individual's field of view and project a DRI/PCDRI onto the individual's retinal image plane 108. The projected DRI/PCDRI can be digitally compensated such that when it is received at the individual's retinal image plane 108 it appears to be in focus (or more in focus) to the individual's eye, relative to the analog contents of the individual's field of view that would be sensed by the user without compensation. In embodiments where the electronic device 101 includes a backlit display (e.g., a screen, which may or may not coincide with the first image plane 105), the DRI/PCDRI may similarly be used to compensate for the analog appearance of the backlit display to the user's eye. For example, considering an individual with nearsightedness, the appearance of the backlit display may normally appear blurry when displaying digital images that appear to be in focus to a healthy eye. The electronic device 101 may project a DRI/PCDRI onto the individual's retinal image plane 108 such that the modifications to the above optical function(s) or DRI/PCDRI(s) cause the appearance of the projected image to be in focus (or more in focus) to the individual's eye relative to the analog contents of the backlit display without using any modification.

The various components of electronic device 101 may be internal, external, partially external (e.g., mounted) to the electronic device 101. Although shown in FIG. 1A as a singular device, the components of the electronic device 101 may be distributed amongst multiple other electronic devices that each include a subset of the components constituting the electronic device 101. These other multiple electronic devices may communicate with each other such that equivalent functionality of electronic device 101 is achieved via coordination amongst these other multiple electronic devices. For example, the image projection module 102 or image capture module 103 may be embedded in a piece of smart eyewear; whereas the processor 114 and memory 155 may be embedded in a mobile phone or tablet that communicates wirelessly (e.g., via a Bluetooth or Wi-Fi connection) with the smart eyewear.

Throughout this disclosure, various examples of image planes (e.g., first image plane 105, second image plane 106, and retinal image plane 108 in FIG. 1A) are described and/or illustrated as flat surfaces. However, it should be understood that in various embodiments of the present invention, an image plane may possess a degree of curvature. For example, the retinal image plane 108 can be curved to match the curved surface of a retina.

Figure 1B:
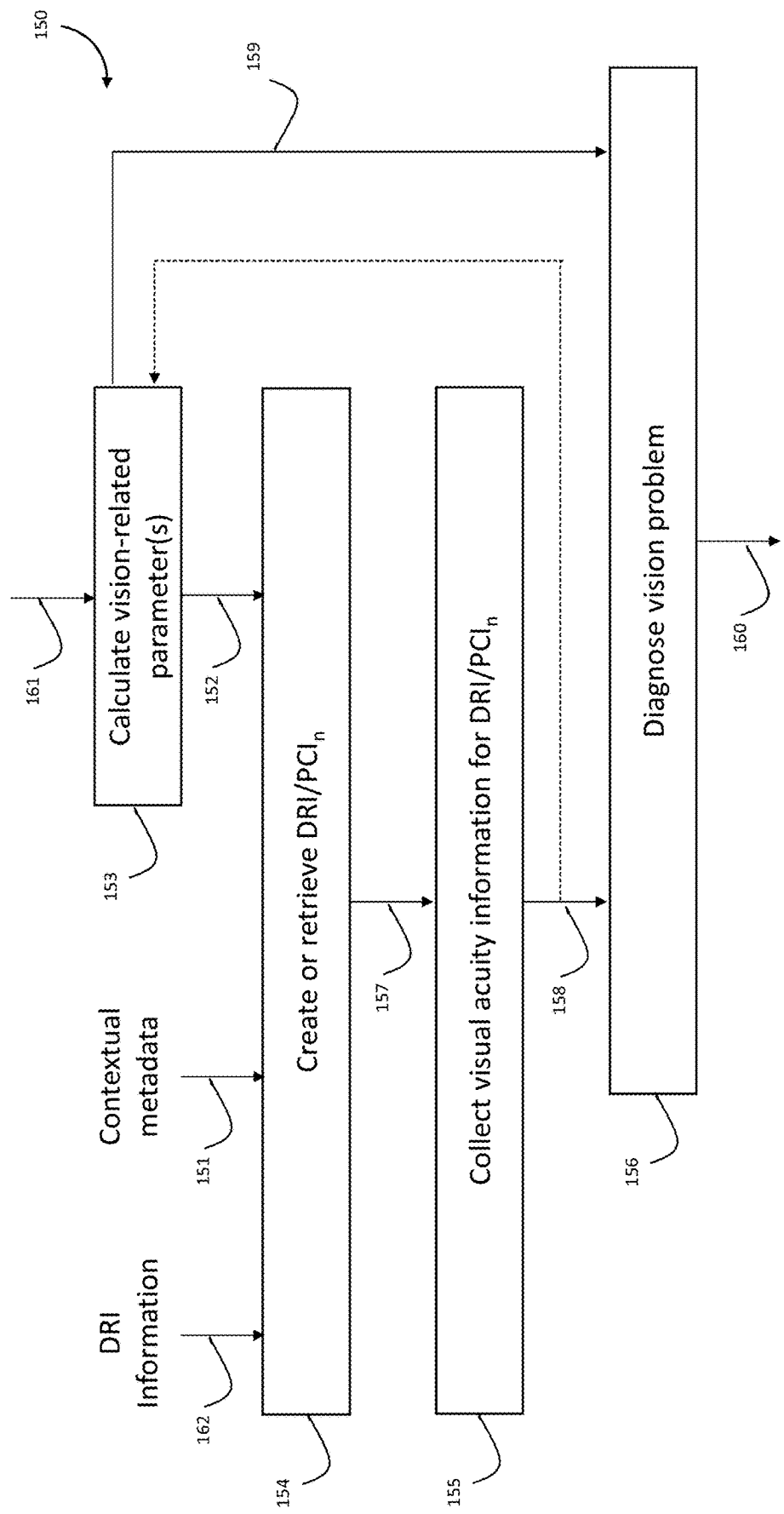
FIG. 1B is a diagram illustrating aspects and embodiments of a method for diagnosing vision problems.

FIG. 1B illustrates aspects and embodiments of a method 150 for diagnosing an individual's vision problem(s) and parameters associated with one or more vision problems. The method 150 may be implemented using the system 100 illustrated in FIG. 1A. As described above, vision problems generally refer to a deficiency of the eye causing an imperfection in vision, and include refractive errors such as myopia, hyperopia, astigmatism, and/or presbyopia, as well as vision impairments such as macular degeneration, retinopathy, retinitis pigmentosa, and/or glaucoma. Vision problems may also mean difficulty seeing in the dark (e.g. night blindness), difficulty transitioning from a light to a dark setting, or difficulty distinguishing between colors.

At step 153, the value of one or more vision-related parameter(s) is calculated based on individual (e.g., patient) information 161 that is either stored in advance or collected via a user interface or communications interface. Step 153 may be implemented, for example, using the electronic device 101 illustrated in FIG. 1A. In certain embodiments, the vision-related parameter(s) may alternately or additionally comprise default/test values not specifically derived from the individual undergoing testing. In certain embodiments, vision-related parameters may be physical optical parameters, such as for example a lens power. In other embodiments, vision-related parameters may be optical image processing parameters. In certain embodiments, vision-related parameters may describe a vision problem type or vision problem degree of severity. In some embodiments, it may be desirable to calculate optical image processing parameters from one or more physical optical parameters. For example, if the vision problem is myopia or hyperopia, it may be desirable to calculate a value of the fitting coefficient $\beta$ in Eq. 2 from a value of the lens power parameter. The process of determining the value of one or more vision-related parameters may involve normalizing a received or retrieved parameter and/or converting parameters to intermediate form(s).

At step 154, a DRI is generated, received as an input 162, or retrieved from internal storage or memory. In some embodiments, step 154 may involve receiving or retrieving information related to a DRI and subsequently generating a DRI based on the received information. The DRI may be processed to create a PCDRI based on, (i) the vision-related parameter(s) 152 received as an output of step 153, and, (ii) in some instances, contextual metadata 151. Step 154 may be implemented, for example, using the electronic device 101 illustrated in FIG. 1A. Step 154 may involve one or more image processing steps to pre-compensate for one or more vision errors. Processing steps may include but are not limited to filtering, image inversion, image mirroring, image rotation, image scaling (amplification or attenuation), image superposition, modifying image color, brightness or contrast, modifying color, brightness or contrast of one or more specific pixels within the image, modifying parameters that correlate with color, brightness or contrast of one or more pixels within the image (e.g. RGB values), applying a brightness or contrast gradient to one, all or a subset of pixels, superimposing color, brightness or contrast information related to one pixel onto one or more other pixels; altering color, brightness or contrast of one or more pixels based on the position or location of said pixel or pixels in the image, calculating a Point Spread Function ("PSF"), calculating a PF, calculating an OTF, calculating a BOTF, and/or calculating inverse functions thereof.

Step 154 may further utilize statistical analysis methods, machine learning methods, and other artificial intelligence methods, possibly in combination with one or more processing techniques described above, to determine the color, brightness and/or contrast for one or more pixels of the PCDRI. Other processing steps are also possible. A signal processing unit (e.g., the signal processing unit 124 of the system 100) may also take into account user input or inputs obtained from one or more ancillary sensors or components.

It is possible that some of the contextual metadata are retrieved from a tracking device (e.g. a wearable), a medical record or a patient information management system. It is possible that the individual undergoing the eye exam is asked to confirm one or more contextual metadata inputs, before those inputs are used to perform image pre-compensation at step 154. It is also possible that the individual might be asked to consent to the tracking/recording of information and/or consent to the use of the tracked/recorded information for the purpose of the eye exam. In some embodiments, one or more contextual metadata input(s) may change over the course of an eye exam, and step 154 may be used to dynamically compute a PCDRI taking into account the most recent contextual metadata input(s) available. In other embodiments, the vision diagnostic system may collect contextual metadata input(s) at or prior to the start of the eye exam, and then use those collected metadata inputs as static values in computation during step 154.

At step 155, one or more DRIs and/or one or more PCDRIs are shown to the individual using one or more displays/screens or are otherwise projected onto the individual's retina using one or more image projectors and visual acuity information about said image(s) is collected. Step 155 may be implemented, for example, using the electronic device 101 illustrated in FIG. 1A. In some embodiments, the method for diagnosing an individual's vision problem and parameters associated with said vision problem may be an iterative process. An individual may be shown a sequence of PCDRIs, optionally following an initial DRI (e.g., using the image projection module 102 shown in FIG. 1A). In some embodiments, steps 153, 154, and 155 may be repeated iteratively (as illustrated by the dashed line from step 155 returning to step 153). Visual acuity information may be obtained during each iteration and input back into step 153 to compute a next set of vision-related parameter values, where it can be used to generate a subsequent PCDRI at step 154 and repeat the cycle.

At step 155, DRIs and/or PCDRIs are shown to the individual and visual acuity information is obtained in response to each of the one or more DRIs and/or PCDRIs that are shown. Visual acuity information may be obtained using one or more passive and/or active techniques. For example, an electronic device such as the electronic device 101 illustrated in FIG. 1A may be used to perform one or more of the following techniques: operate an image capture module (e.g., 103 in FIG. 1A) to passively capture and record an RRI from the individual's retina, in response to the individual viewing one or more DRIs/PCDRIs; operate a neural sensor module (e.g., 117 in FIG. 1A) to passively sense one or more neurological responses generated in response to the individual viewing each DRI/PCDRI (neurological responses include but are not limited to, brain wave patterns); operate one or more user interfaces (e.g., 118 in FIG. 1A) to actively collect user input data from the individual before, during, or after she views each DRI/PCDRI; and operate one or more communications interfaces (e.g., 119 in FIG. 1A) to send or receive exchange data with an external node or database. Visual acuity information of one or more previously displayed images (e.g., DRIs/PCDRIs) may be taken into account to calculate the value of one or more vision-related parameters used for the creation of a new pre-compensated image in the sequence (as illustrated by the dotted feedback line that extends from the output of step 155 to an input of step 153 in FIG. 1B).

At step 156, visual acuity information 158 output by step 155, is optionally combined with vision-related parameters 159 (output by step 153, which may include some or all of the vision-related parameters 152) to determine one or more additional vision-related parameters or diagnostic parameters 160. Step 156 can be used to diagnose a vision problem and/or derive the value of at least an additional vision-related parameter (e.g., besides the values of the vision-related parameters 152, 159 that are generated as outputs by step 153) or diagnostic parameter for the individual undergoing the exam.

Other embodiments of the method of FIG. 1B as described above are also contemplated. For example, step 153 which computes one or more vision-related parameters, may optionally take as an input 161 the vision problem category for which the individual is being tested. Example categories may include but are not limited to one or more of the following: nearsightedness (or "myopia"), farsightedness (or "hyperopia"), astigmatism, presbyopia, night blindness, color blindness, retinopathy, macular degeneration, glaucoma. Said vision problem category input may be taken into account to determine a set of relevant vision-related parameters and/or values for said vision-related parameters. As an example, if the vision problem falls into a refractive error category (e.g. nearsightedness, farsightedness, astigmatism, presbyopia), vision-related parameters may refer to traditional lens prescription parameters, and said parameters may for example be used by step 154 to calculate a PSF, a PF, an OTF, a BOTF, and/or inverse functions thereof. In another example, if the vision problem falls into one of the retinal damage categories (e.g. retinopathy, macular degeneration), one or more parameters may correspond to specific image coordinates and may be used by step 154 to re-direct content of the original DRI, or adjust parameter(s) (e.g. brightness, color, contrast) for one or more pixels in the area defined by said image coordinates. Other examples are also possible.

In certain embodiments, step 153 may optionally take as an input historical information 161 about the vision problem for which the individual is being tested (e.g., using the electronic device 101 of FIG. 1A to access locally stored data and/or remotely stored data using a communications interface 119). Examples of such historical information may include but are not limited to parameters and/or date of most recent and/or historical eyewear prescription(s), information from a medical record or other patient information management system, such as localization information about damaged areas of the retina as previously diagnosed by a doctor. Historical information inputs may for example be used to calculate or otherwise generate an initial set of values for one or more relevant vision-related parameter(s). Using historical information inputs to generate an initial set of values may make the diagnosis process faster or more efficient.

Some of the inputs 161 used for step 153 can be retrieved from a medical record or other patient information management system (e.g., using a communications interface 119 of the electronic device 101 shown in FIG. 1A). It is also possible that the individual undergoing the eye exam is asked to confirm one or more additional inputs before they are used (e.g., via a user interface 118 of the electronic device 101 shown in FIG. 1A). It is also possible that the individual is asked to consent to one or more additional inputs being used to inform parameter calculation at step 153 (e.g., via a user interface 118 of the electronic device 101 shown in FIG. 1A). As previously mentioned, step 153 may optionally take as an input, visual acuity information collected by the system at step 155 for one or more previously displayed images. Previously displayed images may include one or more DRIs and/or PCDRIs.

In one example, in an eye exam with an objective of determining an individual's lens power, parameter values corresponding to a lens power strength in the mid-range of a distribution of lens power that is recorded for a number of individuals, may be fed as inputs to step 154 to create a DRI or PCDRI. Based on the ensuing visual acuity information collected at step 155 for the DRI or PCDRI, and optionally also based on visual acuity information previously collected for one or more previous DRIs/PCDRIs, step 103 may calculate a new set of parameter values corresponding to the current PCDRI to be generated and displayed in a subsequent iteration. Step 153 may continue to update its parameter outputs using this iterative technique, until no further or little improvement (e.g., improvement less than a pre-configured threshold) is detected in visual acuity information from two or more consecutive generated/displayed PCDRIs. This is just one illustrative example. Other iterative algorithms to dynamically derive a new set of values for vision problem-related parameters from visual acuity information previously collected from the individual are also possible.

In a different embodiment, step 153 may not take into account visual acuity information previously collected from the individual to determine a next set of parameter values. It may for example output a pre-configured sequence of parameter values (e.g., default or test values), which may be based on patient information 161.

In specific embodiments, step 153 may further take as an input an individual's personal information 161. Personal information may among other information include one or more of the following: age, gender, medical history information (e.g. smoking, diabetes, retinopathy, glycemic control), current or historical activity or behavior information (e.g. physical activity, sleep patterns, stress). It is possible that some of the inputs to step 153 are retrieved from a tracking device, a medical record or other patient information management system (e.g., using the electronic device 101 of FIG. 1A to access locally stored data and/or remotely stored data using a communications interface 119). It is also possible that the individual undergoing the eye exam is asked to confirm one or more inputs before they are used by step 153 (e.g., via a user interface 118 of the electronic device 101 shown in FIG. 1A). It is also possible that the individual is asked to consent to the tracking/recording of information and/or consent to the use of the tracked/recorded information for the purpose of the eye exam (e.g., via a user interface 118 of the electronic device 101 shown in FIG. 1A).

In certain embodiments, it may be possible for step 154 to create one or more PCDRIs ahead of time, prior to the start of the eye exam. In such embodiments, step 154 may rely on vision-related parameters 152 received from step 153, patient information 161, and/or contextual metadata 151, to determine which existing PCDRI to display to the individual. In other embodiments, step 154 may create PCDRIs in real-time or near real-time.

In various embodiments of the method 150, at step 156, visual acuity information 158 and/or vision-related parameters 159 or 152 (via intermediate steps 154 and 155) may taken as inputs and processed to diagnose an individual's vision problem(s) and derive one or more additional vision-related parameters or diagnostic parameters 160 associated with such vision problem(s). Examples of such parameters 160 are eyewear lens prescription parameters, parameters that localize damaged area(s) of the retina and possibly additional parameters indicative of the severity of retinal damage in those areas, or parameters that quantify a gradation of color blindness or night blindness. Other examples are also possible. In one such set of embodiments, a sequence of PCDRIs are displayed using a pre-defined sequence or one of the dynamic iterative methods described herein, visual acuity information for each image is collected, and the parameters associated with the pre-compensated image that yields the highest visual acuity rating are selected. Other examples are also possible. In some embodiments, step 156 may calculate a first additional vision-related parameter based on inputs 158, 159, and/or 152 (via intermediate steps 154 and 155) and subsequently calculate a diagnostic parameter 160 or second additional vision-related parameter 160 based on the first additional vision-related parameter.

In certain embodiments of the method 150, creation of a PCDRI may not be necessary. For example, if the purpose of the examination is to localize retinal damage, showing only one or more DRI(s) to the individual may be sufficient, and post-processing on the DRI(s) and corresponding feedback (e.g., RRIs) may be sufficient to localize one or more damaged sections of the retina. In that case, some processing may still be required to normalize, convert, or otherwise adjust for context based on the contextual metadata inputs 151 and/or patient information 162 (e.g., information specifying the types or degrees of the vision problem(s) at issue). Such processing could be performed as pre-compensation step prior to steps 155 or 156, or alternatively, it may in some embodiments be implemented as a post-processing step following steps 155 or 156.

Some or all outputs 160 of diagnosis step 156 may be stored on a local electronic device such as a smartphone, tablet, laptop or smart eyewear (e.g. A/R or V/R eyewear). Alternatively, or in addition, said outputs may also be sent to and stored in a medical record or other patient information management system. Some or all outputs 160 may also be sent to an eyewear ordering system. In some embodiments, transmission of this data is in electronic format over a network connection. Some or all outputs 160 may be used to configure or adjust a digital display, A/R or V/R glasses or contact lenses. Some or all outputs 160 may be used to adjust the content, brightness or contrast of one or more images or recordings, or of one or more pixels of one or more images or recordings, prior to being displayed on a digital display or on A/R or V/R glasses or contact lenses.

If an output 160 is a lens prescription for contact lenses, output 160 may among other parameters, include power (aka sphere or strength), base curve, diameter, brand, etc. If the output 160 is a lens prescription for eyeglasses, output 160 may among other parameters, include power (aka sphere or strength), cylinder, axis, add, prism, base, acuity, pupillary distance, etc. Other parameters are also possible. Other information about prescription, such as the type of eyewear (contact lens, glasses, etc.), and the vision problem (near-sightedness, farsightedness, astigmatism, etc.), may also be included in output 160. (e.g., vision problem type, location(s) on retina, power [aka sphere or strength], base curve, diameter, brand, etc.). If the output 160 is a lens prescription for eyeglasses, output 160 may among other parameters include power (aka sphere or strength), cylinder, axis, add, prism, base, acuity, pupillary distance, etc. Other parameters are also possible.

In some cases, it may be sufficient to determine the image processing parameters needed to correct for an individual's vision problem related errors, and it may not be necessary to compute physical vision problem-related parameters, such as for example eyewear lens prescription parameters. In such embodiments, it may be possible to simplify the vision diagnostics methods. For example, a series of (processed)

images may still be shown, and visual acuity information about said images may still be collected (either with active input from the individual or automatically). Optimal image processing parameters for the individual may be obtained by selecting the image processing parameter values for the processed image that received the highest visual acuity rating. Other selection criteria are also possible. In certain embodiments, step 155 includes displaying and/or projecting the contents of the DRI and/or PCDRI(s) to an individual using one or more displays and/or more projectors and collecting visual acuity information about said DRI and/or PCDRI. In one such set of embodiments, visual acuity information may be obtained by the individual providing input. An individual is shown a series of PCDRIs on an electronic device (or as projected from an electronic device). The one or more displayed images reach the individual's retina. The one or more images are each processed to compensate for different gradations and/or types of refractive errors. The individual is asked for his/her assessment of the visual acuity of each image in the series of images. Alternatively, the individual may be asked to read out loud the text shown in PCDRI and the individual's voice response may be recorded and processed to determine a visual acuity measure/proxy for that image. Other methods to determine a visual acuity measure are also possible.

Visual acuity information may also be obtained in step 155, automatically, for example, by capturing one or more images of the retina while the image is being projected onto the retina. Visual acuity information may for example be a visual acuity rating. Visual acuity information may also be obtained from comparing a captured RRI, after further processing, to a DRI or PCDRI.

Different methods may be used to collect or determine an individual's visual acuity with regard to a displayed image. The displayed image can be the original image or a pre-compensated image. In one specific embodiment of the present disclosure, an individual may be asked to rate the visual clarity of an image on a scale of 1 to 10 for example. In another embodiment, an individual may be asked to compare the visual clarity of two or more images, or to rank two or more images based on visual clarity.

In yet another set of embodiments, the image(s) may be an eye chart or otherwise contain letters, numbers, words and/or sentences. The individual may be asked to read out the text he/she sees on the image, or record it either an electronic device (e.g., via a user interface), or by writing it down on paper. Other methods to collect the content of the DRI/PCDRI as perceived by the individual ("user input") are also possible (e.g., sign language).

Figure 1E:
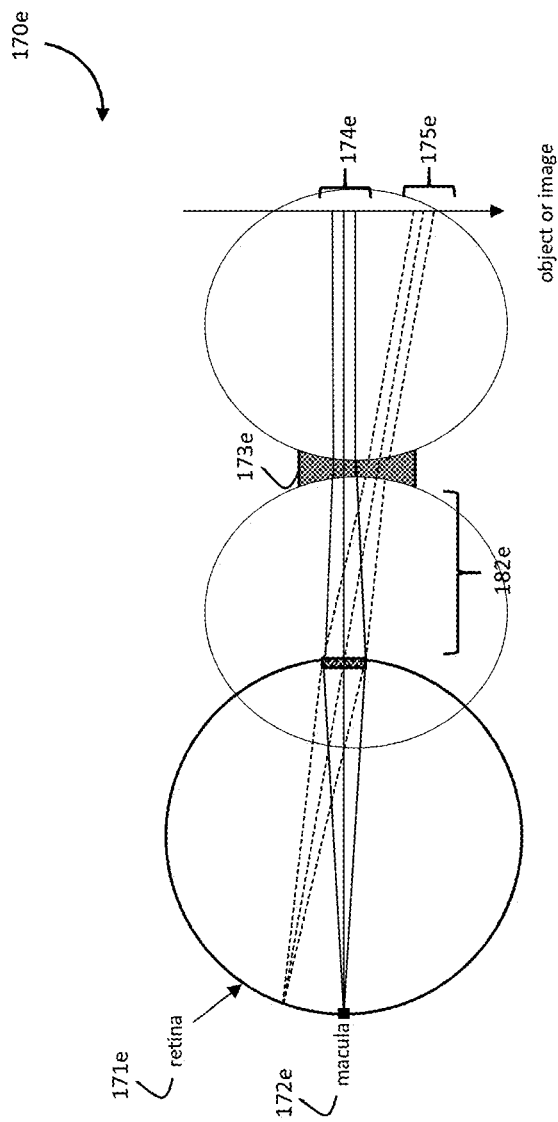
FIG. 1E is a diagram illustrating aspects and embodiments of a physical lens being used to change the optics of light entering an eye.
Figure 1F:
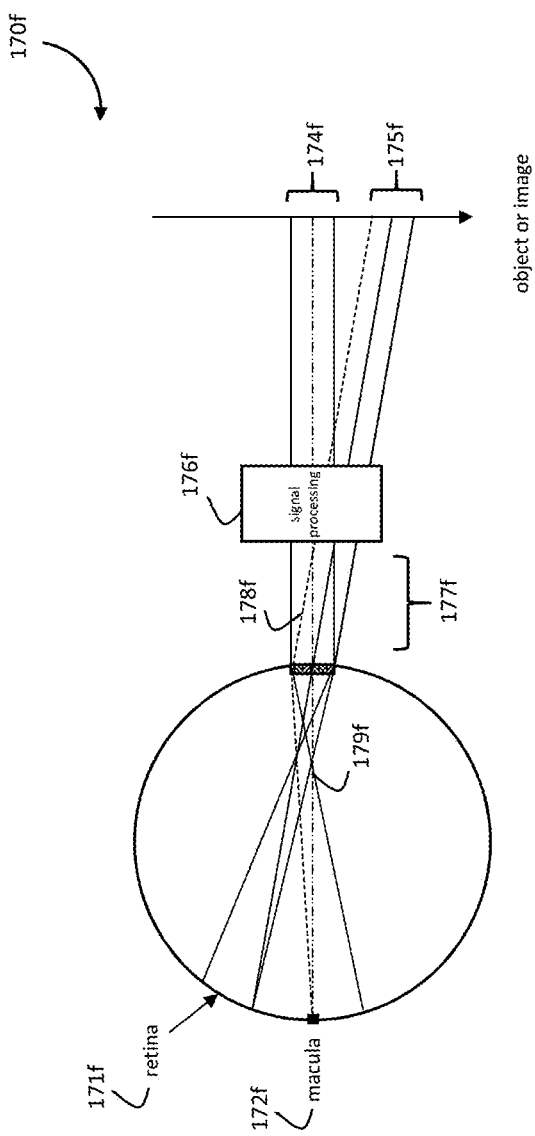
FIGS. 1F and 1G are diagrams illustrating aspects and embodiments of a conceptual signal processing unit that is used to generate and/or manipulate light entering an eye.
Figure 1G:
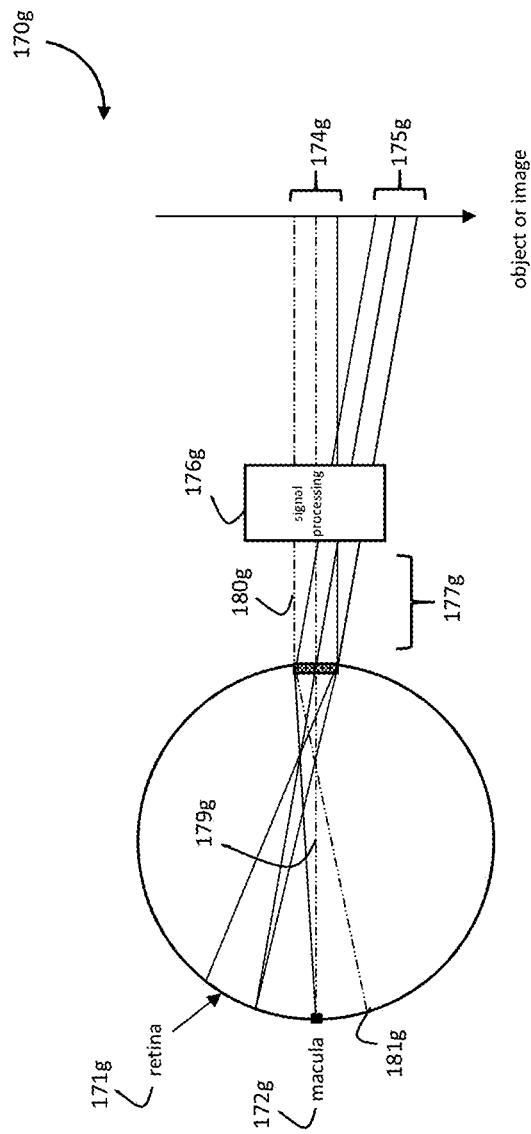

Examples of several diagnoses (i.e., relating to vision problems) as generated by the system 100 of FIG. 1A and/or the method 150 of FIG. 1B, and examples of signal processing actions that can be taken to correct the diagnosed vision problems, as also generated by the system 100 of FIG. 1A and the method 150 of FIG. 1B, are illustrated by FIGS. 1G and 1F and discussed below.

FIG. 1C shows an example of a system 170c including an eye that does not suffer from a refractive error. It can focus parallel rays of light on the retina 171c. Incident light rays 174c that are aligned or substantially aligned with the central axis of the eye's field of view ("direct incident light") are focused such that they converge at or substantially at the macula 172c portion of the retina, where the concentration of light-sensitive neurons is greatest. Incident light rays 175c with an angular offset more towards the periphery of the eye's field of view ("peripheral incident light") are focused such that they still converge on the retina 171c, but at a location displaced from the macula 172c.

FIG. 1D shows an example of a system 170d including an eye exhibiting nearsightedness, causing rays of incident light 174d and 175d to converge before they reach the retina 171d. Accordingly, both direct incident light 174d and peripheral incident light 175d will appear blurry to the eye exhibiting nearsightedness because the respective rays of light converge inside the eye's internal optical cavity (before the retina) and re-diverge upon arriving at the retina 171d at the rear surface of the internal optical cavity. In contrast, in the healthy eye shown in FIG. 1C, both direct incident light 174c and peripheral incident light 175c is focused by the optics of the healthy eye such that the respective rays of light converge at or substantially at the retina 171c (and further at the macula 172c in the case of direct incident light). FIGS. 1C and 1D are shown as a one-dimensional cross-section, but it should be understood that these describe three-dimensional optical behavior of an eye. The macula 172c-g, is a part of the retina 171c-g at the back of the eye responsible for central vision. It has a very high concentration of photoreceptor cells that detect light and send signals to the brain, which interprets them as images. The rest of the retina 171c-g processes peripheral (side) vision.

FIG. 1E shows an example of a system 170e including an eye and a physical lens 173e being used to change the optical focus of rays of incident light 174e and 175e as they propagate and reach the eye's retina 171e. In this example, a concave lens is used, and the rays of incident light are diverged 182e before reaching the eye, moving the optical focus from before the retina onto the retina 171e (and further onto or substantially onto the macula 172e in the case of direct incident light 174e).

FIG. 1F and FIG. 1G conceptually depict embodiments and examples of systems 170f and 170g, respectively, each including an eye and a signal processing unit 176f-g configured to perform corrective actions in response to one or more vision problems, for example the nearsightedness illustrated in FIG. 1D. In these embodiments, an optical signal processing device ("optical signal processing unit" or "signal processing unit") 176f-g is positioned in the field of view of an individual's eye and used to digitally capture, intercept, and/or manipulate one or more rays of direct incident light 174f-g and/or peripheral incident light 175f-g propagating towards the eye. In various embodiments of the present invention, rather than modifying the direction of incident light by means of a physical optical lens (or other analog optics), the image content itself can be modified (e.g., at least in part by digital or electronic components) to cancel out the blur caused by the eye's refractive error. For example, the electronic device 101 of the system 100 may implement the optical signal processing unit 176f-g and may further perform image capture and/or image projection functions described elsewhere in this specification for digitally correcting an optical parameter and/or vision problem associated with an individual's eye.

More specifically, the system 170f (FIG. 1F) depicts a set of embodiments where such an optical signal processing unit 176f generates and/or changes information encoded in one or more image pixels displayed to the eye to correct for the nearsightedness illustrated in FIG. 1D. The optical signaling processing unit 176f may do so by ensuring the information carried by the ray of light in the center 179f reaching the macula 172f, cancels or partially cancels the information carried by ray of light 178f that originates from peripheral vision, but otherwise reaches the macula 172f instead of the peripheral portion of the retina 171f due to the eye's nearsightedness.

More specifically, the system 170g (FIG. 1G) depicts a set of embodiments where an optical signal processing unit 176g generates and/or changes the information encoded in one or more image pixels displayed to the eye to correct for the nearsightedness illustrated in FIG. 1D. Without correction being applied by the optical signal processing unit 176g, the information carried by a ray of light from the edge of focal vision 180g is projected on the eye's retina 171g outside the macula area 172g due to the eye's nearsightedness. The optical signal processing unit 176g generates and/or changes the information encoded in one or more pixels near the center of focal vision 179g such that the information from the edge of focal vision 180g is partially or completely canceled by the information carried near the center 179g projected onto the eye's macula.

The optical signal processing units 176f-g, as mentioned above, may be implemented by the electronic device 101 of the system 100 such that the electronic device 101: (a) modifies the image it generates outside of the external optical channel 111 and internal optical channel 112, and then (b) sends the modified image through the external optical channel 111 and internal optical channel 112 onto to the eye 104. System 100 may use one or more signal processing steps to manipulate digital image parameters in this manner, including but not limited to image scaling such as image amplification or image attenuation; image superposition; image inversion; modifying image color, brightness or contrast; modifying color, brightness or contrast of one or more specific pixels within the image; modifying parameters that correlate with color, brightness or contrast of one or more pixels (e.g. RGB values), applying a brightness or contrast gradient to one, all or a subset of pixels; superimposing color, brightness or contrast information related to one pixel onto one or more other pixels; altering color, brightness or contrast of one or more pixels based on the position or location of said pixel or pixels in the image. The signal processing performed by system 100 may use statistical analysis methods, machine learning methods and other artificial intelligence methods possibly in combination with one or more processing techniques described above to determine the color, brightness and/or contrast for one or more pixels of the image output. Other signal processing steps are also possible. The signal processing unit 176g-f may also take into account user input or inputs obtained from one or more ancillary sensors. Accordingly, in various embodiments the signal processing unit 176f-g can function as a "virtual lens" capable of digitally intercepting and compensating the optics of incident light onto an eye without the use of (or without fully relying upon) conventional analog optical element(s) (e.g., a lens), but in a manner that causes the displayed light to appear to the eye as if it had been modified by said conventional analog optical element(s). In a preferred set of embodiments, said virtual lens functionality is applied to compensate for a refractive error of the eye, such as the nearsighted eye shown in FIG. 1D.

While FIG. 1F and FIG. 1G illustrate examples of how signal processing can be applied to project the desired image content, color, brightness and/or contrast onto the eye's macula, those skilled in the art will appreciate upon learning about the present invention that similar signal processing techniques may also be applied to (1) correct for other types of vision problems and refractive errors; and/or (2) project the desired image content, color, brightness and/or contrast on other areas of the eye's retina that are responsible for peripheral (side) vision. In various embodiments and examples of the present invention, the system 100 of FIG. 1A may be used to implement the examples described in FIGS. 1G and 1F such that electronic device 101 includes/performs the functions associated with the optical signal processing unit 176f-g. For example, the optical signal processing unit 176f-g may model the optics of light projected onto an eye using an OTF, PF, PSF, inverse functions thereof, and/or a BOTF, as is further described in the context of the system 100 of FIG. 1A. The modified image parameters discussed above may be determined by the signal processing unit 176f-g and projected onto the eye based on a comparison of an RRI, contextual metadata, personal data, user input, and/or other user types of inputs or feedback discussed throughout this specification (e.g., in FIGS. 1A and 1B). In so doing, the signal processing unit 176f-g may generate a PCDRI that digitally corrects for a known or suspected vision problem of the eye. For example, a PCDRI correcting for a refractive error will appear to be in focus to the eye suffering from the refractive error, but would otherwise appear blurry or out-of-focus to a healthy eye.

In various embodiments implementing an optical signal processing unit 176f-g, the electronic device 101 of the system 100 may include an image projection unit configured to digitally project an image directly onto the retina of an individual and/or onto the retinal image plane 108 positioned within the field of view of the individual's eye. In such embodiments, electronic device 101 may alternately or additionally include a display component (e.g., an LCD, LED, or OLED display) configured to digitally display an image on an image plane (e.g., a screen) positioned within the field of view of the individual's eye. As discussed above, the displayed/projected images are generated by system 101, so as to digitally compensate for an individual's vision problems by modeling the optical signal processing unit 176f-g. Accordingly, digital image parameters may be adjusted to compensate for an individual's known or suspect vision problems and/or associated optical parameters.

Figure 2:
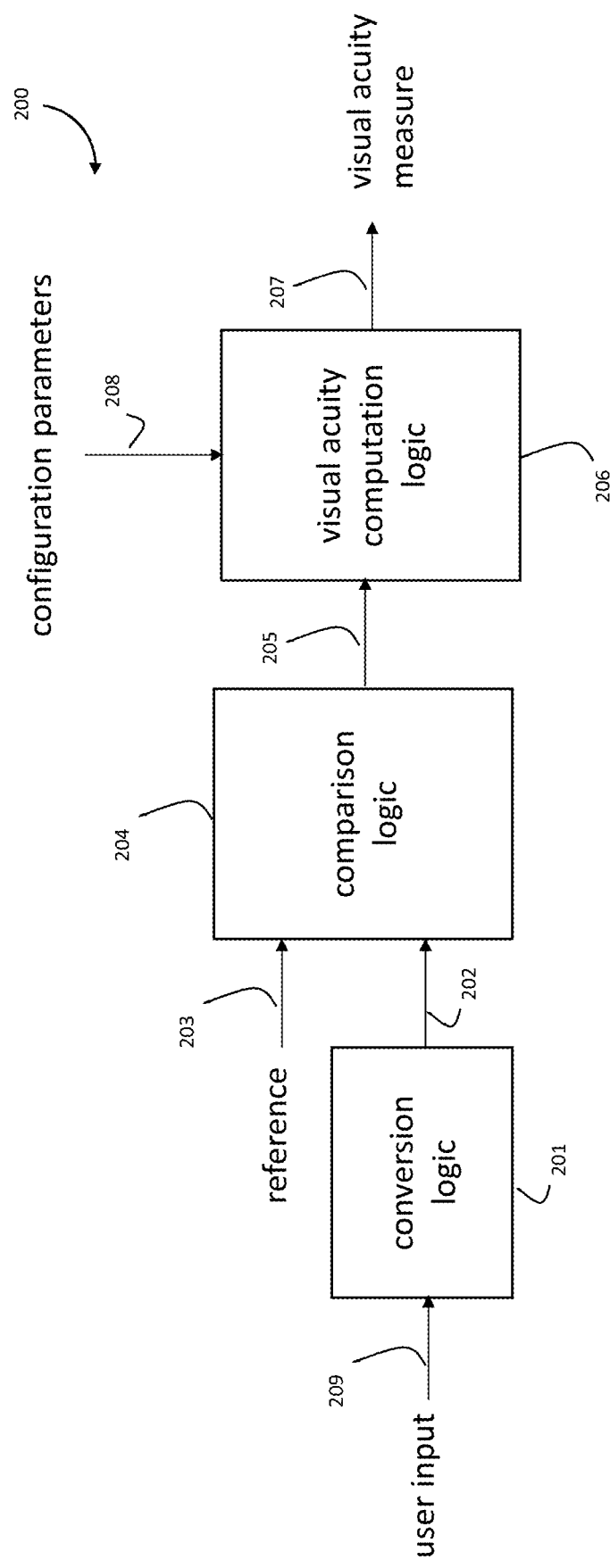
FIG. 2 is a diagram illustrating aspects and embodiments of a system for performing visual acuity computations.

FIG. 2 shows a diagram of a system 200 for performing visual acuity computations based on user input in accordance with at least one embodiment of the present disclosure. The system 200 may be implemented, for example, as part of the electronic device 101 shown in FIG. 1A. The system 200 may further implement some or all of the steps of method 150 illustrated in FIG. 1B, and in some embodiments describes further characteristics of the method 150.

The system 200 includes conversion logic 201, which is configured to receive and/or convert user input 209 characterizing the user's vision problems and/or perception of the DRI/PCDRI (e.g., content of the DRI/PCDRI as perceived by the user) into a machine-readable data format 202. The machine-readable data format may comprise a string, bitstream, vector, array, or combinations thereof. Other known machine-readable data formats are also possible. Conversion logic 201 may further include data recording and/or data processing logic.

For example, if the user input is a voice input characterizing the user's perception of the DRI/PCDRI, voice recording and voice recognition methods may be used to convert the audio input into a machine-readable data format that represents the content of the text spoken by the individual. If the input method is sign language, a video recording of the individual may be recorded and image processing and image recognition methods, including but not limited to artificial intelligence ("AI") and machine learning ("ML") techniques, may be used to convert the image recording content into a machine-readable data format. The user input can also include a captured RRI caused by the projection of the DRI/PCDRI onto the retina 201 of the eye 104. When implementing an AI or ML technique, the system 200 may further include and/or utilize a communications module to exchange data with one or more external servers, nodes, or databases (e.g., using an API call).

In some embodiments, the system 200 further includes comparison logic 204 capable of receiving reference signal(s)/data 203 that are either locally stored or retrieved from an external server, node, or database using a communications interface. Regardless of the format of the user input and method of retrieval, it may be compared or rated against a reference 203. Reference 203 may include original text that was shown to the individual to obtain/prompt user input 209. If reference 203 is also in a machine-readable format, comparison logic 204 may be used to compare converted user input 209 against reference 203. If it is not in a machine-readable format, reference 203 may be converted to a machine-readable format by additional functionality in the comparison logic 204 (or by other functionality capable of performing such a conversion in the electronic device 101 of system 100). Additional processing steps may be required before a comparison can be performed to normalize the values being compared. The output 205 of comparison logic 204 may be fed into visual acuity computation logic 206 to assign a visual acuity measure 207 to the user input and/or corresponding DRI/PCDRI. Visual acuity computation logic 206 may instead or additionally compute the value for one or more vision-related parameters for the individual subjected to the eye exam.

In one set of examples, the output 205 of the comparison logic may, for example, include a count of the number of characters that differ between the reference input and the user input, or a count of the number of words that are different between both inputs. Other outputs are also possible.

Visual acuity computation logic 206 may take into account one or more configuration parameters 208. Configuration parameters 208 may include, but are not limited to, the size of the displayed text for which user input 201 was collected, or a metric representative of said size; the distance between the user and the display, or a metric representative of said distance; the display brightness; the display contrast. Other configuration parameters are also possible.

Figure 3:
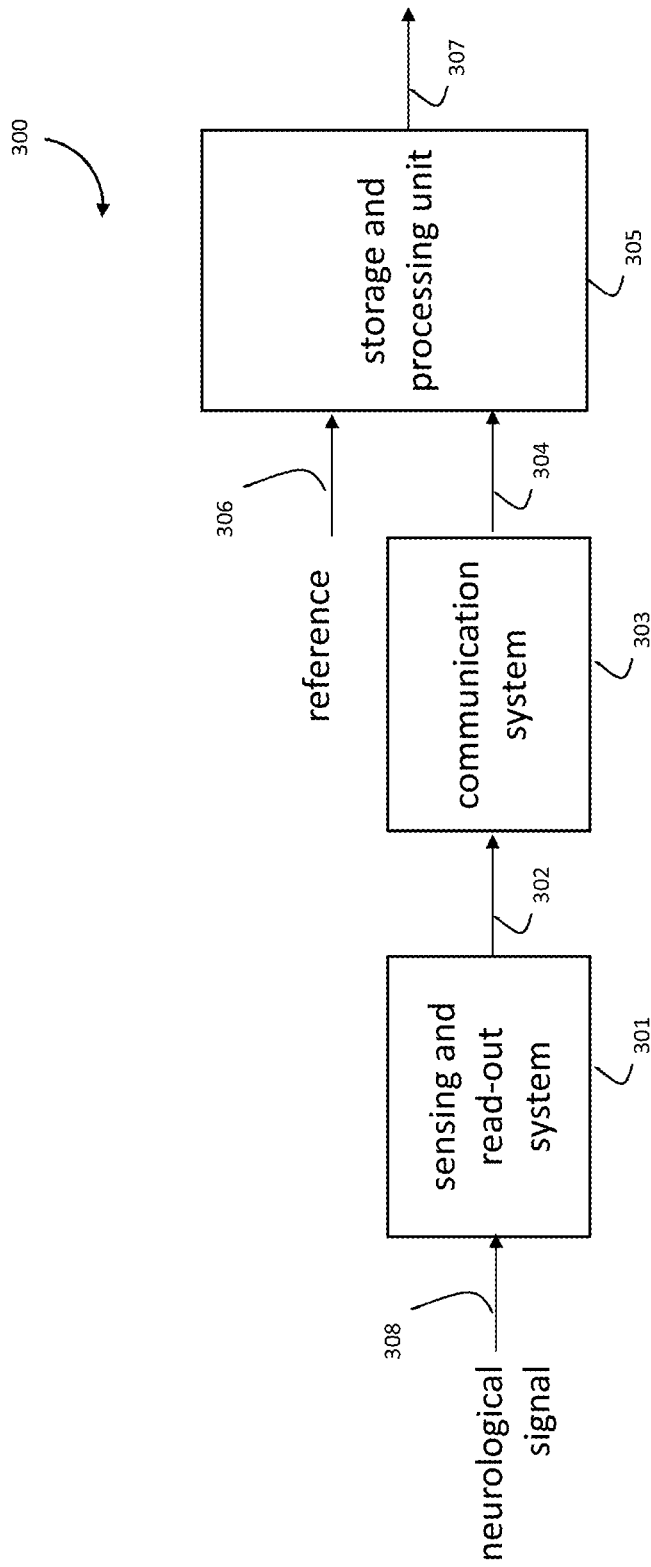
FIG. 3 is a diagram illustrating aspects and embodiments of a system for collecting visual acuity information.

FIG. 3 shows a diagram of a system 300 for passively collecting visual acuity information using a brain-computer interface ("BCI") in accordance with at least one embodiment of the present disclosure. The system 300 may be implemented, for example, using the electronic device 101 shown in FIG. 1A. The system 300 may further implement some or all of the steps of method 150 illustrated in FIG. 1B, and in some embodiments describes further characteristics of the method 150.

The system 300 includes neurological sensing and read-out subsystem 301 configured to sense and process one or more neurological signals 308 related to the stimulation of the nerve cells in the retina in response to the reception of said image. Neurological sensing and read-out subsystem 301 may as one example use an electroencephalogram (EEG) sensor to read brain waves through the scalp. Processing steps performed by sensing and read-out subsystem 301 may further include but are not limited to one or more of the following: filtering, amplification, resampling, analog-to-digital conversion, transformation to a frequency domain signal and superposition. Output 302 of sensing and read-out subsystem 301 may be transferred to an internal or external storage and processing unit 305 using a communication link/system 303. Communication system 303 may use wireless communication protocols such as Wi-Fi, RFID, Bluetooth, inductive transfer, Zigbee, etc. Other wireless communication protocols are also possible. Alternatively, communication system 304 may use a wired link. Data inputs 304 to the communication system 303 may be stored in memory that may be accessed by one or more processing units.

In some embodiments, a reference signal/data 306 may also be stored or otherwise be accessible by storage and processing unit 305. Storage and processing unit 305 may manipulate data input 304 and/or reference input 306 and process the raw and/or manipulated inputs to determine or estimate a refractive error and/or one or more lens prescription parameters. For example, storage and processing unit 305 may map input 304 to a two-dimensional array of pixels. Said two-dimensional array may then be compared to reference 306 or a processed version of reference 306, to diagnose vision problems, using methods similar to the methods described elsewhere in this disclosure. Other examples are also possible.

Storage and processing unit 305 may consider additional parameters in setting up the comparison between the sensed data 304 and reference data 306. For example, the unit 305 may consider the type(s) of sensors and measurements present in the sensing and read-out system 301. The unit 305 may retrieve such additional parameters from a local memory or storage and/or receive such additional parameters from the sensing and read-out system 301 (via communication system 303), from the communication system 303 via an external node (e.g., an Internet connection), and/or from the reference input 306.

The unit 305 may further normalize and/or convert received sensor data 304 or reference data 306 to one or more intermediate forms so that it is possible to directly compare the two data sets. In some embodiments, this may include processing the neurological data 304 to normalize, convert, and/or parametrize the data into one or more intermediate forms so that it can be directly compared to the reference data 306. In other embodiments, unit 305 may process the reference data 306 to normalize, convert, and/or parametrize the data into one or more intermediate forms so that it can be directly compared to the sensed data 304. And in yet further embodiments, unit 305 may normalize, convert, and/or parametrize both the sensed data 304 and the reference data 306 so that direct comparison(s) are possible.

Figure 4:
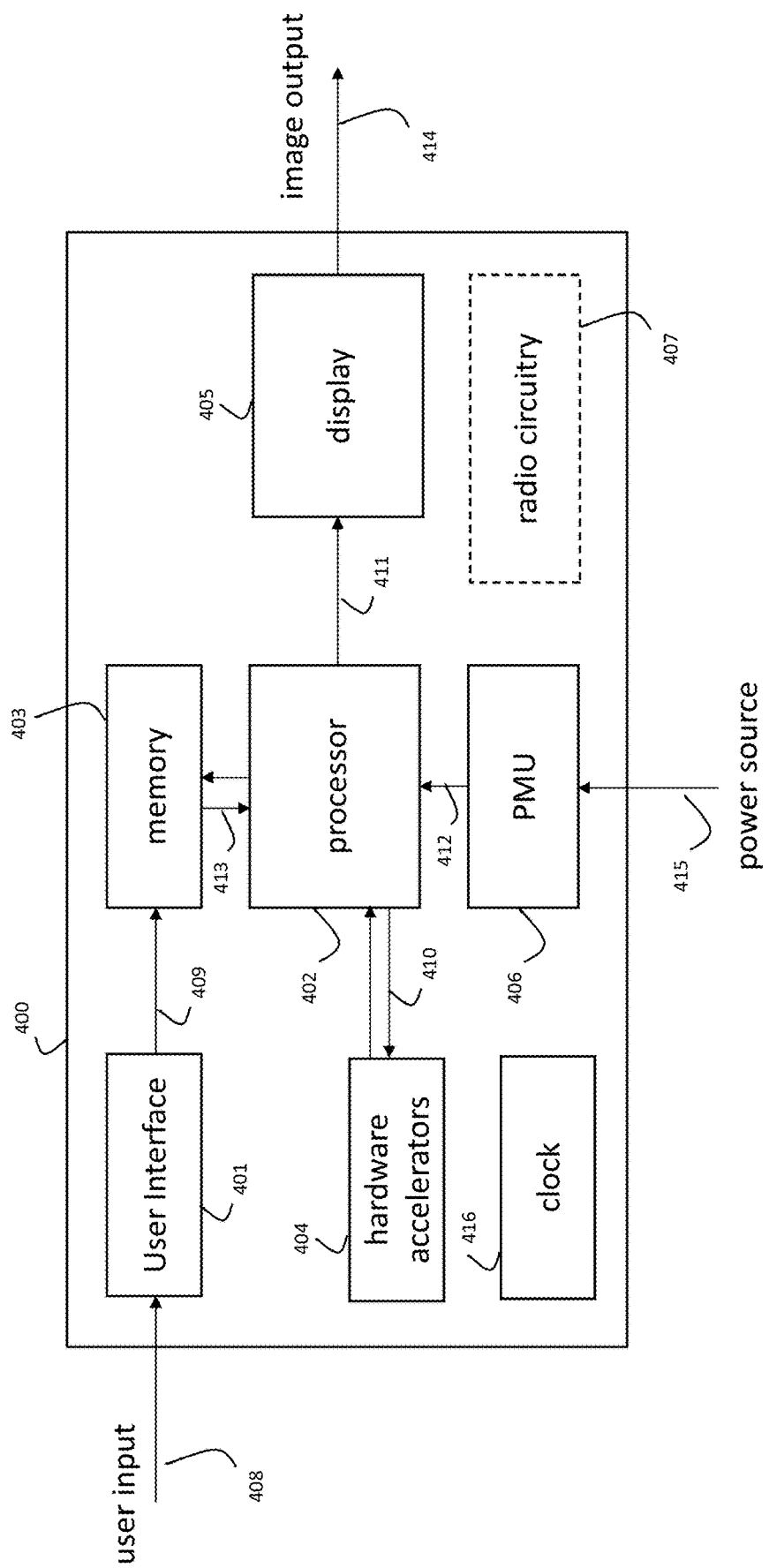
FIG. 4 is a diagram illustrating aspects and embodiments of a device capable of receiving user feedback and providing image output to a user.

FIG. 4 is a diagram illustrating embodiments of an electronic device 400 capable of receiving user input or feedback 408 and providing at least one image output 414, in accordance with this invention. In some embodiments, the electronic device 400 may be integrated with or within the electronic device 101 shown in FIG. 1A. The electronic device 400 may be a mobile phone, tablet, television, electronic billboard, game console, watch or other wearable, medical device, smart eyewear including smart glasses or smart contact lenses, A/R eyewear, V/R eyewear, diagnostic vision equipment, LCD or other electronic display, smart windshield, smart window, smart goggles. Other electronic devices are also possible.

Electronic device 400 typically includes, at least in part, a processor unit 402, memory 403, a clock or crystal 416 and a power management unit ("PMU") 406. Electronic device may also include one or more user interfaces 401, one or more displays 405, one or more hardware accelerators 404 to support or accelerate the execution of instructions by processor 402, and one or more radio modules 407. Although not shown, other components like one or more camera modules, sensors, capacitors, resistors, inductors may also be included in said electronic device. A camera may be used to collect user input passively (e.g., by recording an RRI).

The power source 415 for the electronic device may be a battery. Alternatively, the device may be mains powered, or it may use energy harvesting to generate the power necessary for the electronic device to function. Other power sources are also possible.

While FIG. 4 shows all components housed in a single electronic device, components may also be distributed across multiple physical devices or chassis. For example, display 405 may be housed in a device that is separate from electronic device 400 and said separate electronic device may communicate with electronic device 400 using radio circuitry 407. The device housing the display may also be connected with a cable or wire to electronic device 400. Other examples where components are distributed over multiple devices are also possible. It is also possible that electronic device 400 projects one or more images on a display that is external to electronic device 400. The display can for example be a wall or a screen. Other displays are also possible.

In one set of embodiments, electronic device 400 stores one or more images in a memory 403. Images may be the original DRIs, and/or the PCDRIs made from DRI that have been compensated to account for various levels and/or types of vision problems. The PCDRIs may have been created from one or more original DRIs. The one or more PCDRIs may be created using circuitry and logic that is housed inside electronic device 400. Alternatively, the one or more PCDRIs may be created on a device or server that is external to electronic device 400 and may subsequently be stored in memory 403 of electronic device. 400. In some instances, an external device or server may assist the electronic device 400 in creating a PCDRI such that some of the processing is performed remotely and the remaining processing is performed locally on the electronic device 400.

The creation of the one or more PCDRIs may be performed in real-time or near real-time. Alternatively, the one or more PCDRIs may have been created at an earlier time that is different from and/or not directly related to the time of the exposure of of the PCDRIs before the individual/ patient.

Electronic device 400 may access one or more images (DRIs/PCDRIs) from memory 403 and show them on display 405. An individual may be asked to provide input 408 on shown image(s) using the one or more user interfaces 401. User input 408 may include input on the visual acuity of said image. User input 408 may for example be a written or typed input, a voice input, or a hand gesture input. Other user input formats are also possible. User input 408 may be in structured or non-structured format. User input 408 may be processed to convert it to a standardized and/or structured format. User input 408 (raw and/or manipulated/processed) may be stored in memory 403. User input 408 may be stored in a data record using a structured data format, along with the physical vision problem related parameters and/or the image processing parameters of the image on which the individual provided input. It is also possible that the raw and/or manipulated/processed user input is transferred to and stored on an electronic device, database or server that is external to electronic device 400. Radio circuitry 407 may, among other methods, be used to transfer the data. User inputs may be stored in a structured data format such as a vector, a string or an array. Other data formats are also possible.

Software instructions executed on processor unit 402 may take as input one or more user visual acuity inputs 408 to compute (or select if image has already been created) the image to display next. It is also possible that the order in which processed images are displayed has been pre-configured. It is also possible that the one or more user inputs are transferred to a device that is external to electronic device 400, such that the computation or selection of the image(s) to show next is determined by said external device and that said external device communicates the information on what image(s) to display next back to electronic device 400. Radio circuitry 407 may be used to facilitate communication between electronic device 400 and said external device.

In various examples, the electronic device 400 might be implemented by hardware circuitry, by program instructions that are executed by a general-purpose processor in the electronic device, or by a combination thereof. Where it is indicated that a processor does something, it may be that the processor does that thing as a consequence of executing instructions read from an instruction memory wherein the instructions provide for performing that thing. Where it is described that a processor performs a particular process, it may be that part of that process is done separately from the electronic device, in a distributed processing fashion. Thus, a description of a process performed by a processor of the electronic device need not be limited to a processor within the electronic device 400, but perhaps a processor in a support device that is in communication with the electronic device 400.

In one set of embodiments of device/system 400, a user interface comprises a camera module 401 for capturing one or more images or a sequence of images. The sequence of images may be a series of still images or a video recording. The one or more images may be stored in memory unit 403. It is also possible that one or more images were electronically generated and stored in memory 403. This could for example be the case if the image is an eye chart. Other examples of electronically generated images are also possible. The one or more images may have been electronically generated using circuitry and/or software that is housed inside electronic device 400. Alternatively, one or more images may have been electronically generated by an electronic device that is different from electronic device 400. It is also possible that the one or more images were captured at a time in the past and/or by a camera that is not housed inside electronic device 400. One or more images that have been generated, either electronically or through a camera image capture, may be transferred to electronic device 400 using radio circuitry 407 and stored in memory unit 403. The image could also be a scanned image. Memory may be temporary or persistent, or a combination of temporary and persistent.

Processing unit 402 may access one or more images in memory unit 403, and execute program instructions to modify the content, brightness, color and/or contrast of one or more pixels in one or more images. As an example, program instructions may be executed to modify one or more RGB values of one or more pixels. The modifications of one or more specific pixels may be based at least in part on content, brightness, color and/or contrast of one or more other pixels. The modifications may also be based at least in part on location of said pixel or pixels within the image. The modifications may also be based on user inputs and/or inputs obtained from one or more ancillary sensors such as light sensors, microphones, motion sensors, temperature sensors, image stabilization sensors. Other sensors, sensor modules, and/or sensor arrays are also possible.

The executable program code may among other steps include scaling, superposition, filtering. The program code may among other methods use statistical analysis methods, machine learning methods and other artificial intelligence methods to determine when and/or how to modify the content, color, brightness and/or contrast of one or more pixels. Processing unit 402 may offload one or more processing steps to one or more hardware accelerator circuity 404. This could for example be to speed up the processing, to free up the processing unit for other tasks, to improve power efficiency of the processing.

Processing unit 402 may send one or more modified images to memory unit 403 for storage. If image processing involves a number of steps, image outputs of intermediate steps may also be stored in memory unit 403. They may be stored in temporary memory or in permanent memory. Processing unit 402 may retrieve one or more modified images from memory unit 403 and send to display unit 405 for display of image(s) 414 to one or more users. In a different embodiment of the invention, display unit 405 may communicate directly with memory unit 403 to retrieve one or more images. The output of electronic device 400 may be a projected image, and the display may be a screen or other surface outside electronic device 400.

Figure 5:
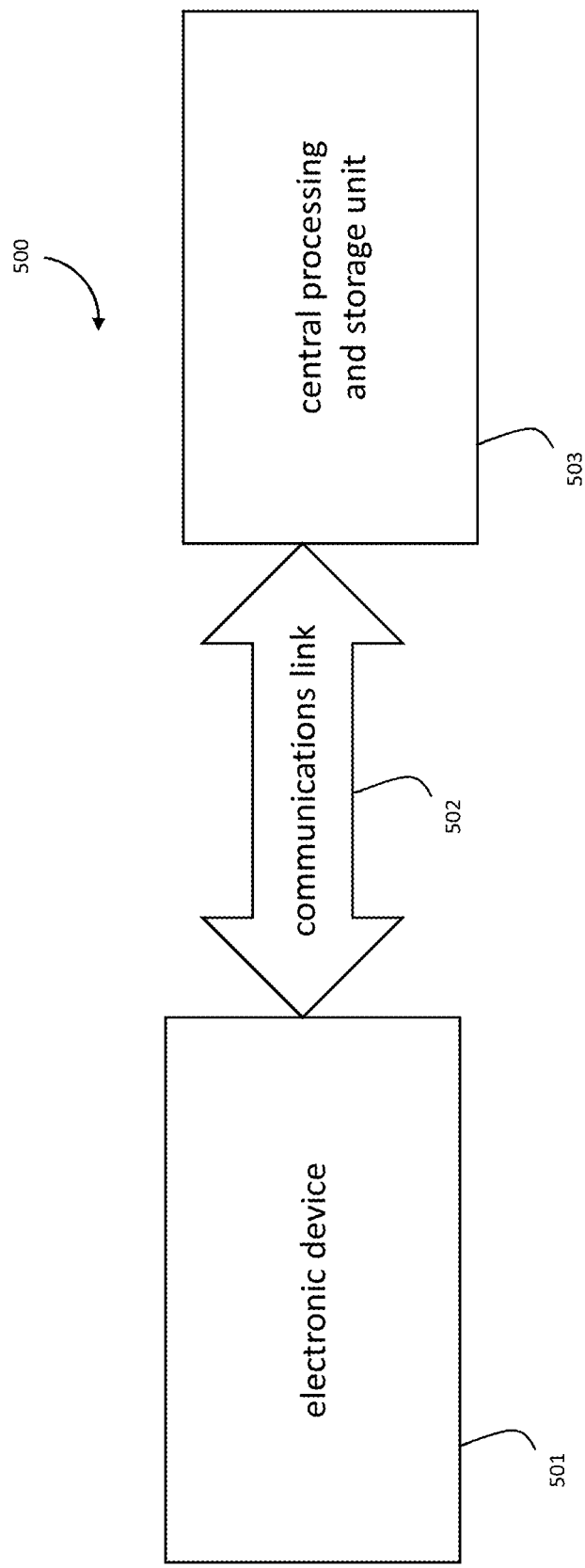
FIGS. 5 and 6 are diagrams illustrating aspects and embodiments of a system including an electronic device and a communications link.

FIG. 5 is a diagram illustrating embodiments of a system 500 including an electronic device 501 communicatively coupled to a processing and storage unit 503 via a communications link 502, which processing and storage unit 503 may be for example the electronic device 101 shown in FIG. 1A and which may practice the method 150 described by FIG. 1B. In certain embodiments, the electronic device 501 may be the electronic device 101 shown in FIG. 1A or the electronic device 400 shown in FIG. 4. The various processing hardware, processing logic, and/or processing steps described in the present disclosure may be implemented over communications link 502 using a central processing unit 503. The communications link 502 may include a network link (e.g. local or Internet) accessed by electronic device 501 via a wired or wireless communications interface. Central processing and storage unit 502 includes one or more processors, servers, computers, and/or storage devices and may be located at the same physical location as electronic device 500 or at a remote location.

Figure 6:
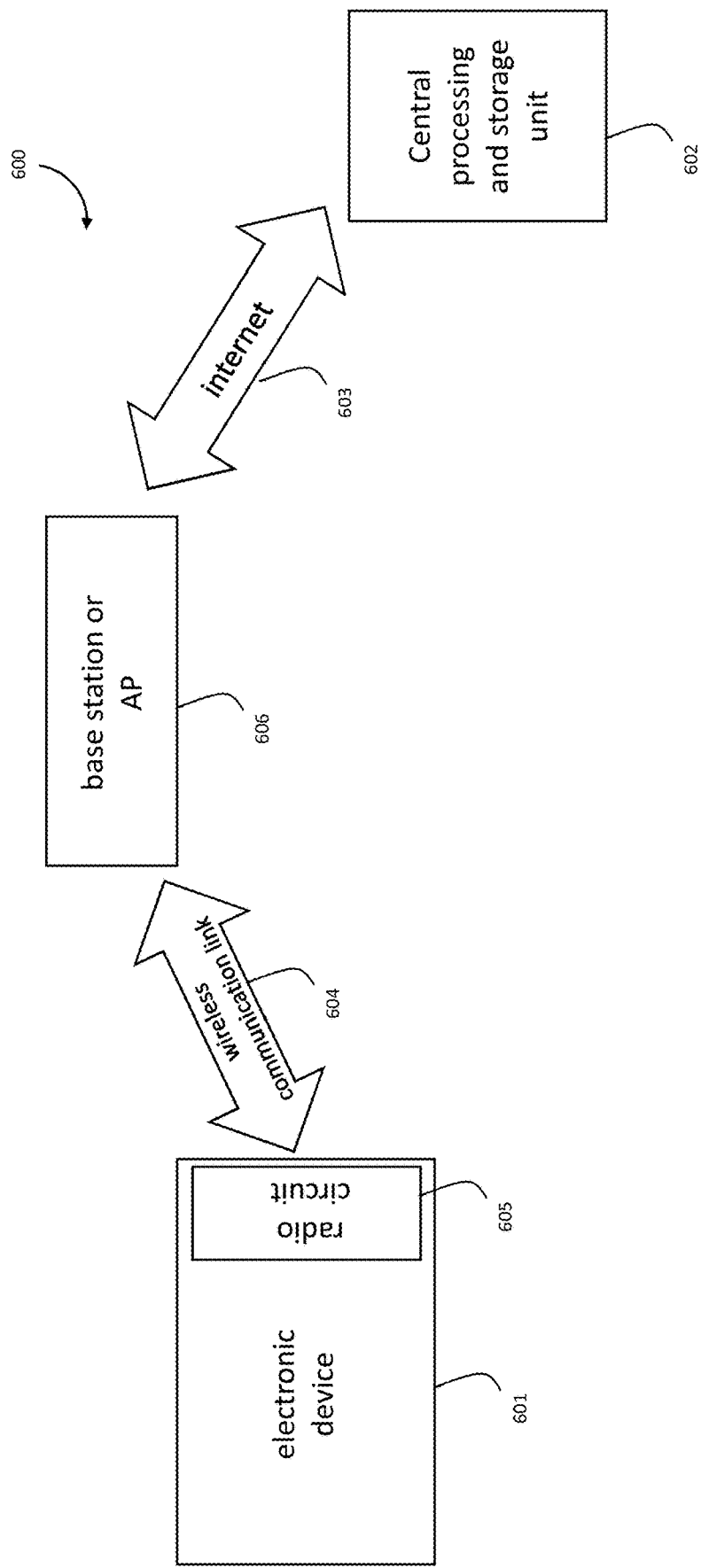

FIG. 6 is a diagram illustrating embodiments of a system 600 including an electronic device 601 communicatively coupled to a processing and storage unit 602 via a wireless base station or access point (AP) 606, which processing and storage unit 602 may be for example the electronic device 101 shown in FIG. 1A, and which may practice the methods described by FIG. 1B. In various embodiments, the system 600 describes further characteristics of the system 500 shown in FIG. 5 or the system 100 shown in FIG. 1A. Electronic device 601 communicates with base station or AP 606 over wireless communication link 604 using radio circuitry unit 605. Base station or AP 606 in turn communicates with central processing and storage unit 602 over internet link 603. Central processing and storage unit 602 may be at the same physical location as electronic device 601 or at a remote location.

As described above, various embodiments of the present invention include systems and methods for performing eye diagnostics based on passive and/or active user input or feedback. Certain embodiments alternately or additionally include systems and methods for digitally compensating vision.

In such embodiments that implement vision diagnostics using passive user input, in addition to or instead of asking an individual for his/her inputs, one or more automatic or passive techniques may be used to determine, or approximate, a user's visual acuity or vision problem-related parameter(s). Automatic or passive techniques do not rely on explicit, active user input. A DRI (or PCDRI) may be projected onto the individual's retina. One or more photos, series of photos, and/or video recordings of the individual's retina (RRIs) may be captured while the DRI/PCDRI is being displayed/projected onto the individual's retina. The image capture is done preferably with a high-resolution camera or similar electronic capturing/recording device. The individual's eye(s) may or may not be dilated for this procedure. It is also possible that the illuminance or ambient light level as observed by the eye can be reduced or controlled to trigger a natural dilation of the eye and associated ambient RRI, which enables a higher quality RRI to be captured and/or reduces the amount of light that needs to be actively projected onto the individual's retina.

To compute or approximate one or more visual acuity measures and/or one or more vision problem-related parameters using passive user input/feedback, a system may implement at least in part one or more of the following steps: (1) generate a DRI; (2) process the DRI to create a pre-compensated image ("PCDRI"), whereby image processing may involve at least in part manipulation of said DRI to pre-compensate for vision-related errors, (3) project the original DRI or PCDRI on an individual's retina, (4) capture one or more photos and/or recordings of the RRI while the DRI/PCDRI is being projected, (5) amplify/process said captured RRI, (6) store the amplified/processed RRI in memory, (7) process the stored RRI and/or the DRI/PCDRI to determine/approximate one or more visual acuity measures, and (8) process the RRI and/or the DRI/PCDRI to determine/approximate one or more vision problem-related parameters.

The above techniques for processing the RRI and/or DRI/PCDRI may include, but are not limited to, filtering, inversion, mirroring, rotation, averaging, scaling (amplification or attenuation), calculating a PSF or PF, calculating an inverse PSF or PF, calculating an OTF, calculating an inverse OTF, calculating a BOTF, calculating an inverse BOTF, applying one or more signal processing techniques on the original/pre-compensated DRI and/or the RRI to compensate for refractive errors (including but not limited to applying a PSF or an inverse PSF), comparing characteristics of one or more pixels, subsets of pixels and/or clusters of pixels of a first image to characteristics of one or more pixels, subsets of pixels or clusters of pixels of a second image. Characteristics may include but are not limited to content, color, contrast or brightness of the one or more pixels. Other processing steps are also possible. Deterministic or known statistical analysis methods may be used to perform the comparison.

In one specific set of embodiments of the present disclosure, an image is projected onto an individual's retina. The image may be a DRI or a PCDRI. The corresponding RRI (i.e., the reflection of the projected image by the retina) is captured and amplified using physical optics (e.g., one or more magnifying lenses), recorded by an electronic recording device (e.g., a digital camera), and stored in memory on said electronic device. Digital signal processing and/or software-based amplification methods may also be used in addition or in the alternative to physical optics. It is possible that the RRI, once recorded, is transferred to another electronic device and stored on said other electronic device. This can include transferring the RRI over a network (e.g., the Internet) to a remotely located electronic device or server.

The projected image (i.e., Digital Reference Image or Pre-Compensated Digital Reference Image) and/or the Reflected Retinal Image are then processed to determine the value of one or more vision problem-related parameters for the individual subjected to the eye exam.

Figure 7:
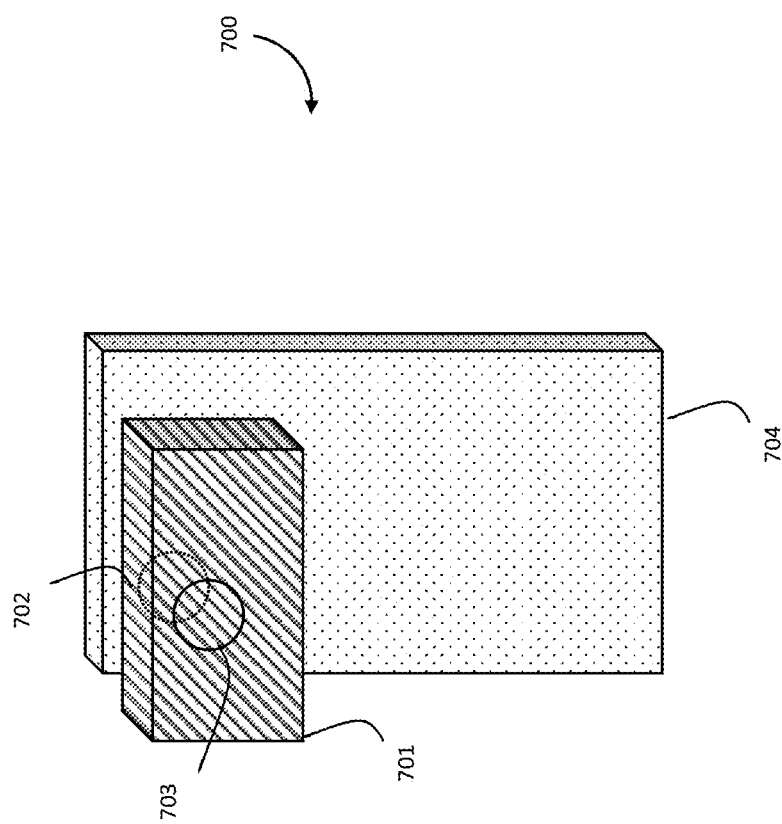
FIG. 7 is a diagram illustrating aspects and embodiments of a system for mounting a first electronic device onto a second electronic device.

FIG. 7 is a 3-D picture depicting embodiments of a system 700 for mounting a first electronic device 701 (mounted device) onto a second electronic device 704 (base device). The combination of the mounted device 701 and the base device 704 may collectively implement the functions provided by the electronic device 101 as shown in FIG. 1A, and may collectively practice the methods described by FIG. 1B The base device 704 may, for example, be a smart phone, a tablet, a laptop, smart glasses, etc. Other recording devices are also possible, as long as they have at least one camera or light source.

The mounted device 701 may, for example, be a camera module or a projector module. In one example, the mounted device 701 is aligned with and mounted over camera 702 of the base device 704, or otherwise attached thereto, and configured to modify or amplify the incoming optics of the camera 702. In another example, the mounted device 701 is aligned with and mounted over a projector 702 of the base device 704, or otherwise attached thereto, and configured to modify or amplify the outgoing light of the projector 702.

In various embodiments, the mounted device 701 may consist at least in part of one or more of the following: (1) one or more outward-facing projectors, (2) a lens that is placed over/aligns with the electronic device's camera, (3) power management unit ("PMU"), and (4) radio circuitry. One or more miniaturized projector(s) such as a retinal projector (aka virtual retinal display) or a femtoprojector may be used. Retinal projectors and femtoprojectors such as for example those described in are well known to those skilled in optical systems. A retinal projector projects a dot matrix directly onto the retina of the eye and is commonly used in A/R and V/R optical systems.

An example of such a retinal projector can be found here: https://digitalnature.slis.tsukuba.acjp/wp-content/uploads/2018/06/2018-siggraph-retinal.pdf, which is hereby incorporated by reference in its entirety for the purposes of describing exemplary structure and functionality of a retinal projector in various embodiments of this disclosure. A projector system comprised of a projector and prism, like the system used in Google Glass [https://www.cnet.com/news/how-google-glass-works-now-and-tomorrow] could also be used as a platform for implementing this invention, which is hereby incorporated by reference in its entirety for the purposes of describing exemplary structure and functionality of a retinal projector in various embodiments of this disclosure. An example of an optical system using an integrated femtoprojector can be found in U.S. Pat. No. 10,580,334 entitled "Peripheral femtoprojector optical systems" to Brian Lemoff (hereinafter Lemoff), which is hereby incorporated by reference in its entirety for the purposes of describing exemplary structure and functionality of a retinal projector in various embodiments of this disclosure.

The projector(s) may be integrated in the lens. A miniaturized projector may be desirable to minimize interference with the capture and recording of image(s) of the retina. The first electronic device 701 may be placed against or otherwise near an individual's eye, with the one or more projectors or camera facing the individual's eye.

The base device 704 may send one or more image(s) to the mounted device 701. Mounted device 701 may project said image on the individual's retina. The image may be an original digital reference image or a pre-compensated image. Pre-compensation processing may involve applying signal processing to compensate for refractive errors, for damage of certain areas of the retina or for night blindness. One or more projectors integrated in mounted device 701 may project said image onto the individual's retina. Camera module 702 inside the base device 704 may record one or more images of the retina corresponding to the projected image. A lens, built into mounted device 701 and positioned in front of camera module 702 may magnify or otherwise manipulate the one or more images projected onto the retina. The magnified/manipulated image may be recorded by camera module 702 in electronic device 704 and stored in memory in base device 704. Alternatively, magnification optics may be built into the base device 704. In yet another embodiment, a reflected retinal image may be recorded and subsequently further processed and amplified.

The "D-Eye" (see https://www.d-eyecare.com) imaging system is one example of a smartphone-based imaging system that can capture retinal images, which is hereby incorporated by reference in its entirety for the purposes of describing exemplary structure and functionality of an electronic device that can capture retinal images, for use in various embodiments of this disclosure.

Processing techniques related to passively collected visual acuity information described elsewhere in this disclosure may be applied to determine a visual acuity measure for an image recorded at a retina, and/or to determine one or more physical vision problem-related parameters for the individual on whom the eye exam is performed. Image processing parameters for optimal, near optimal or otherwise improved digital compensation for said individual's vision problems may also be determined. Other vision diagnostics outputs are also possible.

Mounted device 701 may communicate wirelessly with the base device 704, for example to receive image(s) to be projected onto the individual's retina. Alternatively, a cable or wire may be used to transfer data and/or power between mounted device 701 and base device 700. Other methods for powering mounted device 701 may also be possible. In a variant embodiment, one, more or all components of mounted device 701 may be housed inside or integrated with base device 704.

Figure 8:
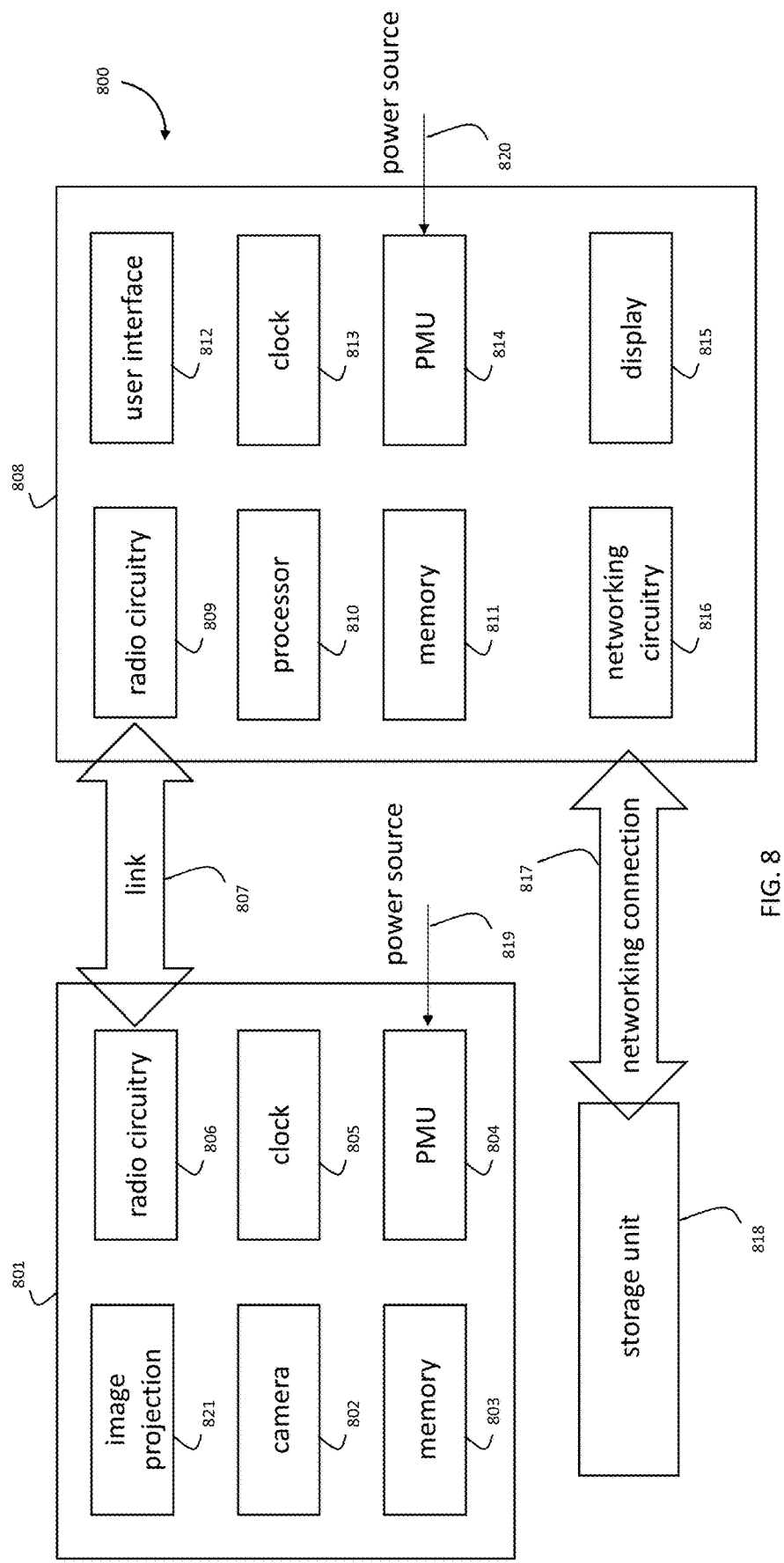
FIG. 8 is a diagram illustrating aspects and embodiments of a system for performing vision care diagnostics and/or vision compensation.

FIG. 8 is a diagram illustrating embodiments of a system 800 for integrating software-based vision diagnostics methods such as those illustrated in FIG. 1B, into a dedicated hardware unit 801, such as an electronic eyewear unit. The system 800, comprising dedicated hardware 801 for implementing electronic eyewear, a storage unit 818 and an electronic device 808 for providing computing and networking to the dedicated hardware 801, may collectively support the same function as the electronic device 101 shown in FIG. 1A, and practice the methods described in FIG. 1B. In various embodiments, the system 800 includes electronic eyewear 801 communicatively coupled to an electronic device 808 via a wired or wireless communications link 807. In certain embodiments, the system 800 describes further characteristics of the system 100 described in FIG. 1A, the system 600 shown in FIG. 6, and/or the system 700 described in FIG. 7. For example, some portions of the electronic device 101 described in FIG. 1A may be implemented in the dedicated hardware 801, while other portions may be implemented in the electronic device 808, as is described below.

Dedicated hardware unit 801 may communicate over wireless link 807 with an additional electronic device 808. Electronic device 808 may in turn communicate with an external local or remote storage unit 818 using a networked connection 817 (e.g., an Internet connection). Alternatively, electronic device 808 may also communicate over a wireless link with an Access Point ("AP") or base station, which in turn may communicate with an external local or remote storage unit 818 over a networked connection 817. It is also possible that dedicated hardware 801 and/or electronic device 808 may alternatively or additionally access data one or more local storage unit(s).

In various embodiments where dedicated hardware unit 801 is electronic eyewear, said eyewear may comprise the form factor of a pair of glasses or contact lens(es). Other form factors are also possible, as long as they are such that electronic eyewear device 801 can be temporarily or permanently mounted on an individual's eye, an individual's head, or otherwise inserted in a stable way in an individual's regular line of vision/field of view. Electronic eyewear device 801 may for example be a set of Augmented Reality ("A/R") glasses, Virtual Reality ("V/R") glasses, A/R contact lenses or V/R contact lenses. Other examples of electronic eyewear are also possible. Such an electronic eyewear device may be prescription or non-prescription eyewear. The individual wearing the electronic eyewear device is hereafter referred to as "the wearer" or "the individual" or "the user."

Examples of electronic eyewear devices include but are not limited to Google Glass, Everysight Raptor, Kopin SOLOS, which are each hereby incorporated by reference in their entirety for the purposes of describing exemplary structure and functionality of an electronic eyewear device. Other examples are described in U.S. patent application Ser. No. 15/937,284 (Wiemer et al.), U.S. patent application Ser. No. 15/993,028 (Kniess et al.), and U.S. Pat No. 10,459,255 (Tuan et al.), which are each hereby incorporated by reference in their entirety for the purposes of describing exemplary structure and functionality of an electronic eyewear device.

Electronic eyewear device 801 includes at least one image projection module 821 for projecting an image onto the retina(s) of an individual wearing or otherwise using the device 801. Image projection module 821 may comprise any known combination of digital image projection hardware using one or more known light emitting elements (e.g., LCD, LED, OLED, lasers, and other known digital light emitting elements and pixel-based image projection elements). For example, digital image projection hardware could include a display chip with an array of individually addressable pixel or sub-pixel light emitting elements. Additionally, image projection module 821 may comprise any known combination of analog image projection hardware (e.g., lenses, mirrors, prisms, gratings, beam splitters, diffusers, optical filters, optical modulators, electro-optical elements, and other known optical elements). Image projection module 821 utilizes said digital and/or analog image projection hardware to control digital and/or analog display characteristics of the projected image (e.g., digital display characteristics such as pixel brightness, pixel color, pixel contrast; and analog display characteristics such as phase, frequency, amplitude, polarization, and other known analog display parameters). Image projection module 821 may be miniaturized so as not to, or minimally, interfere with the user's field of view. Alternatively, image projection module 821 may display or project images or recordings that replace the user's regular field of view, or at least a portion of the user's regular field of view (e.g., to substantially preserve or approximate the user's regular field of view absent the presence of image projection module 821 and/or electronic eyewear device 801).

In certain exemplary embodiments, image projection module 821 may include a digital projector (e.g., retinal projector or femto projector) capable of electronically generating a digital image and projecting said image along an optical axis towards the retina of an individual. Such digital projectors may be designed to project images onto the retina so that the images completely or substantially appear in a person's natural field of vision and/or depth of field. Image projection module 821 may further include additional optical components positioned in the optical path of the retinal projector and configured to modify one or more optical characteristics of the projected image. In addition to the optical components listed above, said additional optical components may further include one or more deformable mirrors, liquid crystals, actuators, and/or MEMS components. For example, the image projection module 821 may include a 2-D array of liquid crystals or deformable mirrors with various cells of the array positioned to receive and operate on one or more pixels or groups of pixels in the projected image.

In various embodiments, electronic eyewear device 801 is structured such that the image projection module 821 digitally projects an image comprising all or substantially all of the light received by the individual's eye (e.g., virtual reality). In other embodiments, electronic eyewear device 801 can be structured such that the image projection module 821 digitally projects an image comprising a portion of the light occupying certain areas or the entirety of the individual's field of view (e.g., augmented reality or digital content overlay).

In one exemplary set of embodiments, the optical projection module 821 includes one or more ultra-miniaturized projectors, for example a retinal projector (aka virtual retinal display) or a femto projector. The device 801 may further include one or more image camera modules 802 (e.g., a camera or wavefront sensor), a memory unit 803, a power management unit ("PMU") 804, a clock or crystal 805, and a radio circuitry 806. Although not shown, other components like one or more sensors, capacitors, resistors, inductors may also be included in said electronic eyewear device.

The power source for electronic eyewear device 801 may be a battery. Alternatively, the device may use energy harvesting to generate the power necessary for the electronic eyewear device to function. Other power sources are also possible. For example, PMU 804 may contain a power coil and may use that coil to receive power wirelessly, for example via magnetic induction.

Radio circuitry 806 may be used to receive one or more images for projection on the wearer's retina using one or more projectors 821. Such one or more images may be received from electronic device 808 over wireless link 807. Radio circuitry 806 may also be used to transmit one or more images captured by the one or more camera modules 802.

Images may be compressed or otherwise reduced in resolution/size by electronic device 808 before being transmitted over radio circuitry 809 to radio circuitry 806 in electronic eyewear device 801. It is also possible that the processed image(s) are already compressed or otherwise sufficiently low resolution. It is also possible that a compression or reduction in resolution was done at an earlier time by electronic device 808 or by another electronic device. Reducing the size of the image(s) may be important because the bandwidth of the wireless link may be limited. It may also be important to minimize the power consumption of the electronic components inside the electronic eyewear device since its power capacity may be very constrained.

Ultra-miniaturized projector(s) 821 may include an image source and an optical system. Ultra-miniaturized projector(s) 821 may be designed to project one or more images from the image source onto the wearer's retina. The projector(s) are typically extremely small (e.g. 1 to 2 mm in any dimension) so as to not significantly interfere with the wearer's view through the eyewear lens(es) nor with any image capture. If multiple projectors are used, such projectors may be positioned at different locations across the eyewear lens(es).

Electronic device 808 may for example be a phone, a tablet, a game console, a laptop or a computer. Electronic device 808 may also be a wearable device such as a watch, ring, necklace, headphones. Other form factors are also possible. While FIG. 8 shows an example embodiment where all components of electronic device 808 housed in a single device. Components may also be distributed across multiple devices.

Electronic device 808 typically includes at least in part one or more of the following: a processor unit 810, memory 811, a clock or crystal 813, a power management unit ("PMU") 814 and a radio module 809. Electronic device may also include one or more user interfaces 812, one or more displays 815, and one or more networking modules that may be used to communicate with an external local or remote storage unit via a networking connection. Although not shown, other components like one or more camera modules, sensors, capacitors, resistors, inductors may also be included in said electronic device 808.

Electronic device 808 may transmit an image to electronic eyewear device 801. Said image is projected onto the wearer's retina and visual acuity information associated with projected image is collected. In one example embodiment, wearer may provide visual acuity feedback using one or more interfaces 812. User interface 812 may be a voice interface, a keyboard or pen, a camera, a gesture sensing interface etc. Other user interfaces are also possible. User inputs may be a voice input, a written or typed text input, a hand gesture input, an image or recording etc. Other inputs are also possible. User interface(s) 812 may be bi-directional. For example, electronic device 808 may communicate an instruction or a question to a wearer via a speaker, headphones or other audio output. A microphone may be used to capture the wearer's response. In another example, electronic device 808 may request the wearer to re-enter or clarify a response. Other examples of bi-directional user interfaces are also possible.

Electronic device 808 may process or otherwise manipulate user input using processor 810 to convert said input into a structured data format. The data format may for example be a string or an array. Examples of structured machine-readable data formats are CSV, JSON, XML, etc. Other data formats are also possible. The formatted/structured input may be recorded as one or more fields in a wearer's data record. The wearer's data record may also be stored in memory 811. It may be desirable that the data format and the order in which user input is recorded in a wearer's data record matches that of one or more fields in a reference record. The reference record may be stored in a database or lookup table.

Electronic device 808 may perform additional processing steps on a user input or a stored reference. Electronic device 808 may store one or more outputs of said processing steps in addition to or instead of the user input. The outputs may also be stored in a wearer's data record. Processing steps may include but are not limited to one or more of the steps shown in FIGS. 1B, 2, and 3 (comparison, computation of visual acuity measure, etc.). Such processing steps may be implemented as instructions that can be stored in memory 811 and executed on processor 810. Such processing steps may be implemented in software, in hardware, or partially in hardware and partially in software.

The wearer may be shown a series of images, and user input for each image may converted to machine-readable format, optionally further processed and stored in one or more wearer's data records. Outputs of the further processing steps (e.g. comparison of user input to a reference or computation of a visual acuity measure) may be stored in addition to or instead of the user input. Instructions stored in memory 811 may be executed on processor 810 to determine the parameters for the next pre-compensated image to be created/displayed, to select which image is projected next, or to determine which pre-compensated images are displayed and in what order.

Vision-related parameters and/or relevant image processing parameters associated with the projected image may be stored in a wearer's data record along with user input or other output(s) from obtained from further user input processing. Alternatively, such parameters may not be stored, but a wearer's data record may be structured such that it is possible to trace a user input uniquely back to a specific pre-compensated image or to a set of parameters associated with a specific pre-compensated image. For example, user input (or outputs obtained from further user input processing) associated with a first known image may be placed in the first field of a wearer's data record, user input (or outputs obtained from further user input processing) associated with a second known image may be placed in the second field of the data record etc. Other examples are also possible.

Methods and systems described elsewhere in this disclosure may be applied to determine one or more parameters of vision or of a vision problem (e.g. lens prescription parameters, localization parameters for retinal damage, other known physical vision and vision problem-related parameters, etc.) from one or more wearer's data records. Such methods may be implemented as instructions that can be stored in memory 811 and executed on processor 810. Such methods may be implemented in software, in hardware, or partially in hardware and partially in software. In one embodiment in accordance with the present disclosure, the one or more vision-related parameters may be stored in memory 811. The one or more image processing parameters associated with the selected lens prescription parameters may also be stored. Alternatively, a wearer's data record(s) may be transferred to an external processing and storage unit 818 over networking connection 817, and the methods to determine one or more parameters of a vision problem may be implemented as instructions on the external processing unit and stored in external memory. The one or more outputs of said processing may also be stored in said external memory unit. In some specific embodiments, one or more outputs of said processing may be sent back to electronic device 808 over networking connection 817.

In specific embodiments of the present disclosure, it may not be necessary to determine any vision-related parameters. Such embodiments may determine the image processing parameters that result in the best visual acuity for the user. The image processing parameters may be computed or stored in addition to or instead of one or more vision-related parameters.

One or more computed or approximated vison-related parameters and/or one or more image processing parameters may be displayed to the user using display 815. Alternatively, they may be stored in memory 811 or 803 for use by electronic device 808, for use by electronic eyewear device 801, or for sharing with an external device or system. For example, one or more parameters may be used to configure or adjust one or more parameters of image projection module 821, or to adjust content, brightness, contrast or other related parameter (e.g. RGB value) of one or more pixels, a subset of pixels or a cluster of pixels of one or more images or recordings prior to said images/recordings being projected or displayed by image projection module 821. One or more parameters may be used to configure or adjust one or more parameters of display 815, or to adjust content, brightness, contrast or other related parameter (e.g. RGB value) of one or more pixels, a subset of pixels or a cluster of pixels of one or more images or recordings prior to said images/recordings being displayed by display 815. Said parameters may be sent to an external processing and/or storage unit over a network connection. The network connection can be wired or wireless. Other methods to output the computed parameters and/or image processing parameters are also possible.

Said outputted parameters may for example be sent to and stored in a medical record or other patient information management system. Some or all outputs may also be sent to an eyewear ordering system. In some embodiments, one or more outputs may be used to configure or adjust one or more display parameters of a digital display, A/R or V/R glasses or contact lenses. Some or all outputs may be used to adjust the content, brightness, contrast or parameter value (e.g., RGB value, gamma value, YCbCr value, or other digital color/pixel related values) of one or more pixels, a subset of pixels or a cluster of pixels of one or more images or recordings prior to being displayed on a digital display or on A/R or V/R glasses or contact lenses.

As described above, in certain embodiments of the present disclosure, it may be desirable that visual acuity information is collected without any active user input (or without collecting as much active user input). One or more eye-facing cameras 802 are built into electronic eyewear device 800. Said camera(s) are typically miniaturized so as to not significantly interfere with the wearer's view through the eyewear lens(es) nor with the image capture. Image projection module 821 may display or project an image on the wearer's retina and said camera(s) may capture one or more retinal image(s) corresponding to the displayed or projected image. Retinal image(s) may be transmitted to electronic device 808 for further processing. A combination of active (i.e. with user action) and passive (i.e. without explicit user action) visual acuity data collection is also possible.

In some embodiments, it may be desirable to test the vision problems associated with only one eye, or only one eye at a time. The wearer may be asked to close the other eye or a processed image may only be projected on one eye's retina at a time. Alternatively, both eyes may be tested simultaneously. In that case, an image to be projected may be divided into a left eye image (projected onto the left eye's retina) and a right eye image (projected onto the right eye's retina). The left-eye image generally covers the left side of the to-be-projected image, whereas the right-eye image generally covers the right side of the to-be-projected image, with some overlap in the center. The division is such that the brain fuses the left-eye and right-eye image into a single image that generally matches the content of the to-be-projected image. The creation of a left-eye and a right-eye image from a to-be-projected image may be implemented on electronic device 808 and transmitted to one or more electronic eyewear devices 801 to minimize the power consumed by electronic eyewear device(s) 801. In the case electronic eyewear device 800 is a set of glasses, both images may be transmitted to the set of glasses and logic inside the glasses may route the left-eye image to the left-eye projector(s) and the right-eye image to the right-eye projector(s). In case electronic eyewear device 801 is a set of contact lenses, the left-eye image may be sent to the left contact lens and the right-eye image may be sent to the right contact lens. Other implementations are also possible.

In specific embodiments, electronic eyewear device 801 is a device through which the user may observe the physical world, such as for example augmented reality glasses or augmented reality contact lenses. In such cases it may be desirable to request that the wearer faces a neutral background while conducting the eye exam, covers the eyewear so external inputs are disabled. In certain embodiments, the electronic eyewear device 801 may mechanically, optoelectronically, programmatically, or otherwise automatically (i.e., without user action) block, suppress or modify specific visual content observable by wearer.

The methods and apparatus described in this disclosure, including the electronic device 801, may also be implemented in other devices such as electronically augmented windows or electronically augmented windshields of transportation vehicles.

Figure 9:
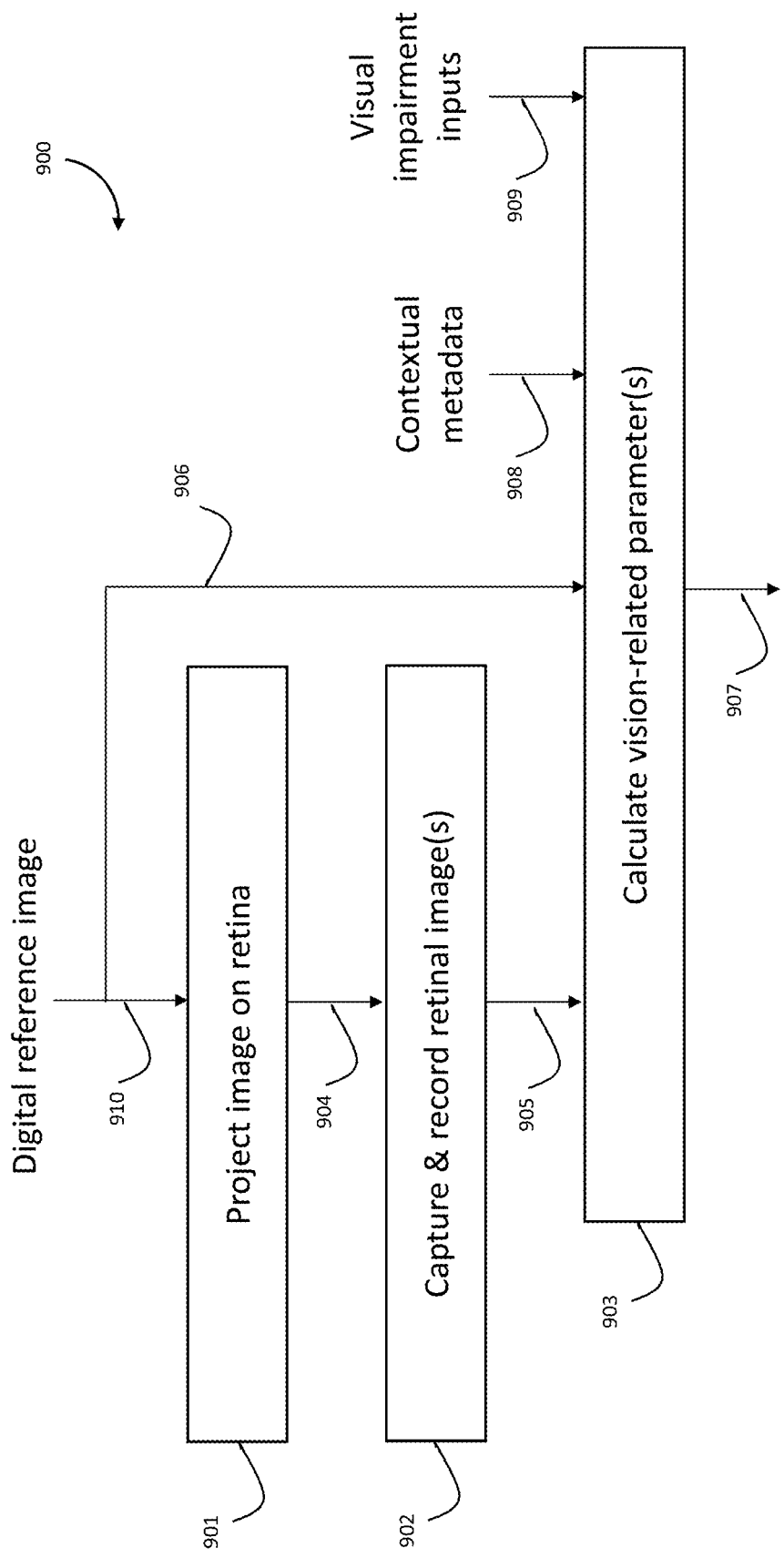
FIG. 9 is a diagram illustrating aspects and embodiments of a method for performing vision care diagnostics.

FIG. 9 illustrates aspects and embodiments of a method 900 for passively diagnosing vision problems and associated optical/vision parameters. At step 901, a DRI 910 is generated or taken as an input and projected through an individual's eye and onto their retina. For the purposes of this invention, an individual can include either a human and a non-human subject having an eye and a retina. At step 902, the RRI 904 of the projected DRI is captured and recorded. Proceeding to step 903, recorded RRI 904 and the DRI 910 are processed to derive the individual's visual acuity and/or at least one vision-related parameters 907. Optionally, step 903 may receive as inputs one or more contextual metadata 908. Optionally, step 903 may further receive as inputs one or more additional inputs 909, for example visual impairment inputs relating to the individual's vision problem(s).

Contextual metadata 908 may among other data include one or more of the following: distance of display from eye, individual's pupil size, display parameters (e.g. resolution, size, luminance), ambient light level (e.g. room illuminance). Additional ancillary sensor inputs may be used to calculate one or more contextual metadata inputs. Ancillary sensors may include but are not limited to one or more of the following: camera, ambient light sensor, speaker, microphone, motion sensors (e.g. accelerometer, gyroscope, magnetometer), vital sign sensors (e.g. blood pressure sensor, heart rate sensor, body temperature sensor). In addition to or instead of ancillary sensor inputs, an individual's personal information may also be used to compute one or more contextual metadata 908. Personal information may among other information include one or more of the following: age, gender, medical history (e.g. smoking, diabetes, retinopathy, glycemic control), current or historical activity or behavior information (e.g. physical activity, sleep patterns, stress). It is possible that some of the contextual metadata are retrieved from a tracking device (e.g. a wearable), a medical record or other patient information management system. It is possible that the individual undergoing the eye exam is asked to confirm one or more contextual metadata inputs before they are used to calculate vision-problem related parameters in processing step 903. It is also possible that the individual is asked to consent to the tracking/recording of information and/or consent to the use of the tracked/recorded information for the purpose of the eye exam.

Additional inputs 909 may include visual impairment information, for example, information describing the type of vision problem being tested for, one or more parameters of the individual's current eyewear lens prescription, one or more parameters of the individual's historical eyewear lens prescriptions. It is also possible that one or more of the visual impairment inputs 909 are retrieved from a medical record or other patient information management system. In some embodiments, the individual undergoing the eye exam may be asked to confirm or consent to one or more additional inputs 909 before they are used.

In an exemplary set of embodiments, the method 900 of FIG. 9 may be implemented using the system 100 depicted in FIG. 1A, or the system 800 shown in FIG. 8.

Figure 10:
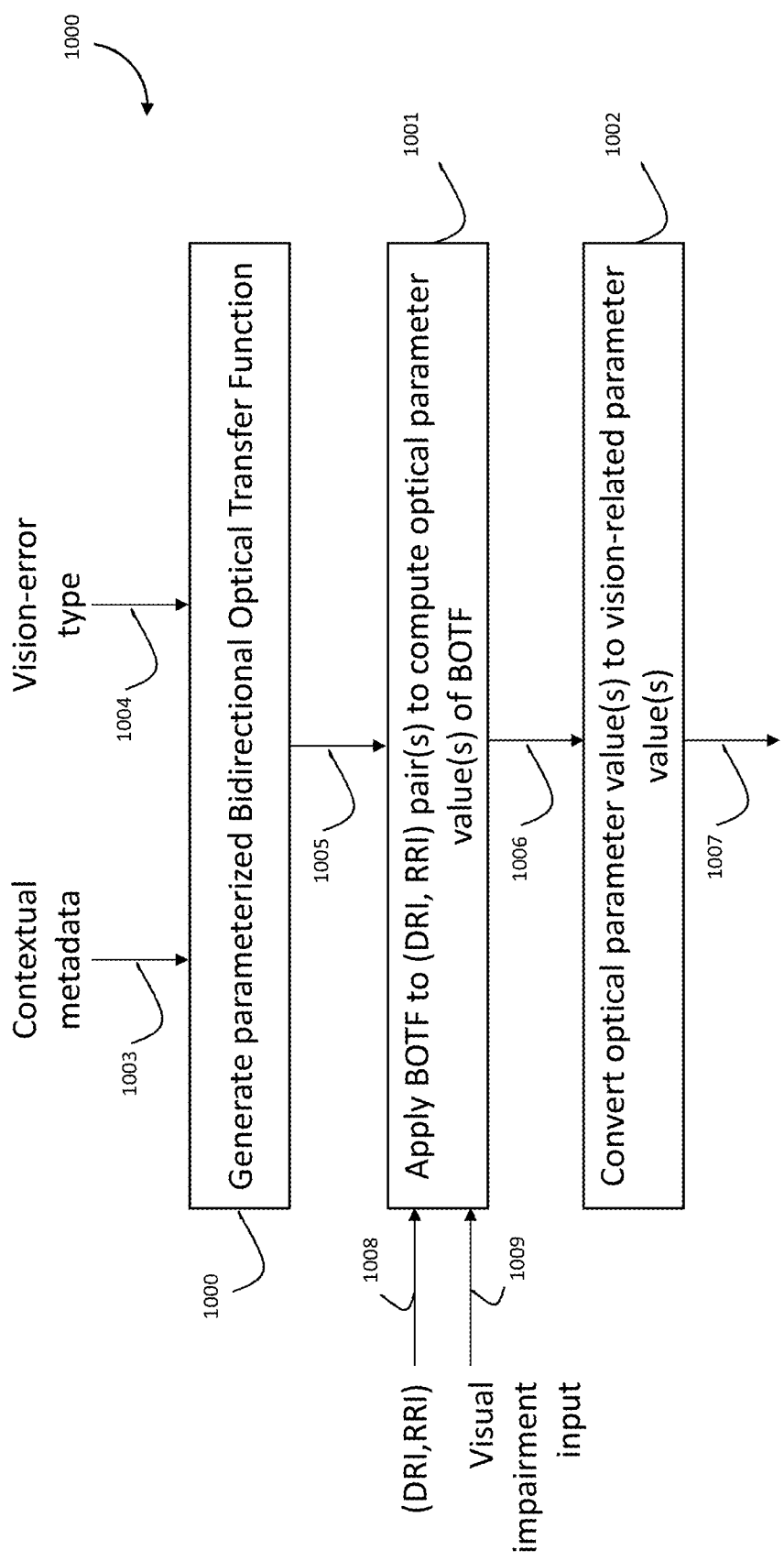
FIG. 10 is a diagram illustrating aspects and embodiments of a method for calculating optical parameters of an individual.

FIG. 10 illustrates aspects and embodiments of a method 1000 for calculating optical parameters and/or vision-related parameters for an individual undergoing an automated eye exam. The method 1000 may, for example, comprise substeps of step 903 in the method 900 shown in FIG. 9. Processing step 1000 generates a parameterized BOTF for one or more specified vision problem types 1004. The BOTF may characterize a single or more than one vision problem type, and may include low-order aberrations, high-order aberrations, or other visual impairments. The pupil function (PF) described above may be used to generate the parameterized BOTF. Processing method 1000 may further take as an input one or more contextual metadata 1003 (e.g., pupil size or distance between the reference image plane and the eye's cornea). One or more contextual metadata 1003 may for example be used to calculate certain parameter values of the BOTF, such that the only remaining unknown parameter(s) in the parameterized BOTF are parameters characterizing optical characteristics of the eye.

At step 1001, the parameterized BOTF generated at step 1001 is used compute one or more optical parameter value(s). In one exemplary embodiment, Eq. 3 is applied to one or more DRI-RRI input pairs 1008 to solve for one or more unknown optical parameters in the parameterized BOTF.

In another exemplary embodiment, the parameterized BOTF (BOTF$_{\beta i}$) is solved by using the DRI to calculate a series of theoretical reflected retinal images (RRI$_{\beta i}$), each such theoretical image corresponding to a specific value $\beta i$ (the unknown optical parameter) using the following equation:

$$RRI_{\beta i}=BOTF_{\beta i}(DRI) \quad (Eq.\ 4)$$

Theoretical reflected retinal images RRI$_{\beta i}$ are then processed and compared to the captured and recorded reflected retinal image RRI using well-known signal processing, statistical analysis, and/or machine learning or artificial intelligence methods and the parameter values for the theoretical reflected retinal image that most closely matches the actual RRI is selected and mapped to output 1006.

In yet another exemplary embodiment, the captured RRI is used to calculate a series of theoretical digital reference images DRI$_{\alpha i}$, each image corresponding to a specific value $\alpha i$ for the unknown optical parameter(s) using the following equation:

$$DRI_{\beta i}=BOTF^{-1}{}_{\beta i}(RRI) \quad (Eq.\ 5)$$

Where BOTF$^{-1}{}_{\beta i}$ is the inverse Bidirectional Optical Transfer Function corresponding to parameter value $\beta i$. Theoretical digital reference images RRI$_{\beta i}$ are then processed and compared to the captured and original DRI using well-known signal processing, statistical, and/or machine learning or artificial intelligence methods. The parameter values for the theoretical digital reference image that most closely matches the actual DRI is selected and mapped to output 1006.

In certain embodiments, more than one optical parameter may be calculated or solved for. For example, multiple DRI-RRI pairs 1008 may be used to solve for the more one optical parameter value. Further, step 1001 may solve the parameterized BOTF using a combination of the above techniques based on Eq. 4 and Eq. 5. Such a combination, may involve one or more iterations of the Eq. 4 process combined with one or more iterations of the Eq. 5 process.

In some optional embodiments, additional visual impairment inputs 1009 related to the individual's vision problems may be used to facilitate processing step 1001. For example, an individual's current and/or historical optical parameter values or vision-problem related parameter values (e.g. lens prescription values) may be used as an initial condition or to inform a range over which theoretical images are generated. Such current/historical optical parameters may be used to assist in generating a DRI, pre-compensated DRI, or theoretical RRI. Other examples are also possible.

In some embodiments, it may be desirable to convert optical parameter value(s) 1006 into different vision-related parameter value(s). This can be accomplished in step 1002, for example, by converting optical parameter value(s) 1006 into physical vison-related parameter values that match the parameters of a conventional eyewear lens prescription. Said converted parameters 1007 can then be stored and sent to a user, patient management or medical record system, eyewear re-ordering system. Other examples are also possible.

Figure 11:
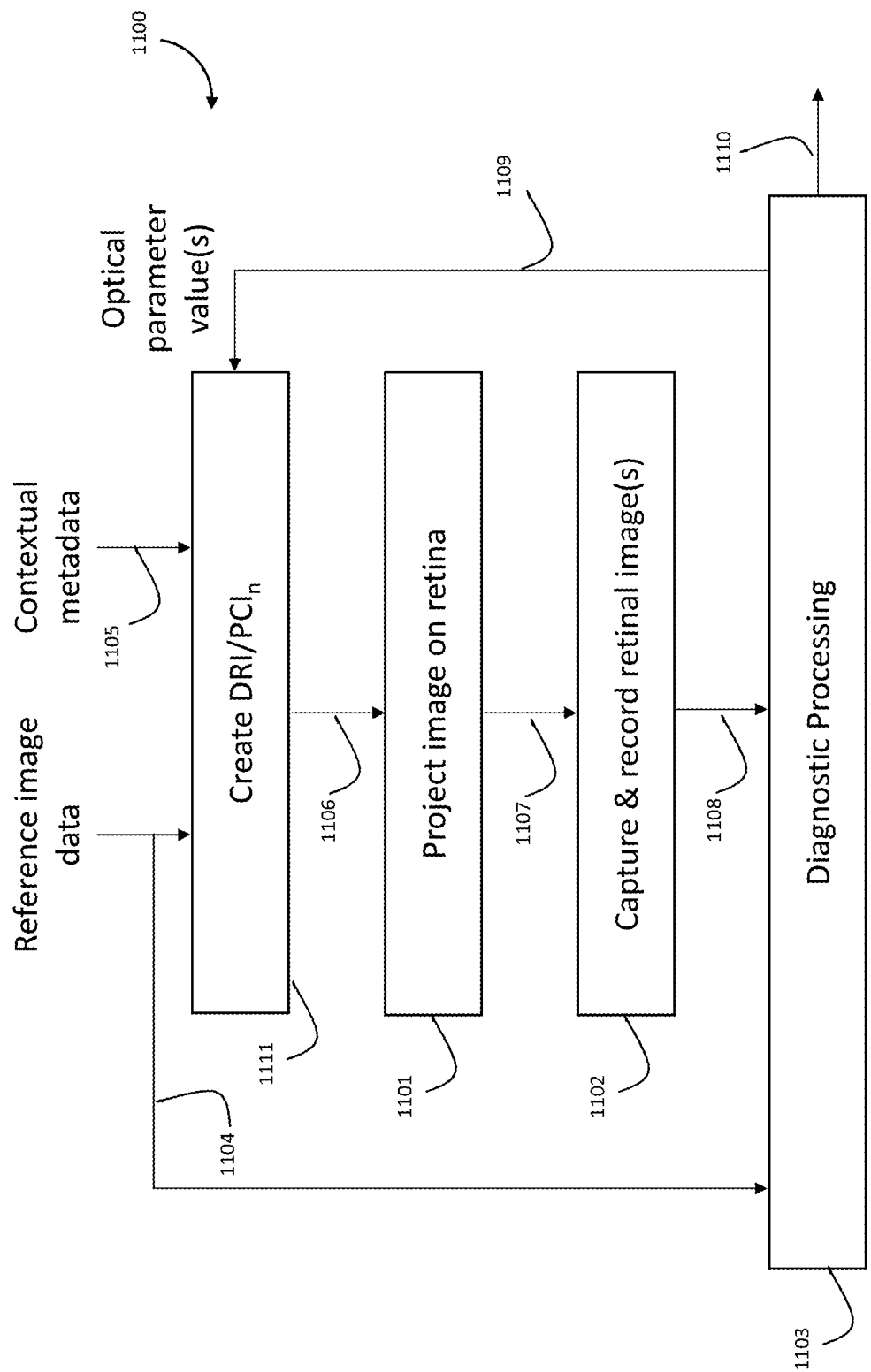
FIGS. 11 and 12 are diagrams illustrating aspects and embodiments of a method for performing vision care diagnostics.

FIG. 11 illustrates aspects and embodiments of a method 1100 for diagnosing vision problems and associated parameters using DRIs and PCDRIs combined with passive user feedback. At step 1111, a DRI or PCDRI is generated. In some embodiments, the method 1100 describes further characteristics of the methods 150, 900, and 1000 illustrated in FIGS. 1B, 9, and 10, respectively, or combinations thereof. The method 1100 may further be implemented using the electronic devices 101, 401, and 801 illustrated in FIGS. 1A, 4, and 8, respectively, or combinations thereof.

At step 1111, the DRI may be created, captured from 1104 and/or processed to create a PCDRI wherein the PCDRI is pre-corrected, at least in part, according to one or more vision error parameter values. For example, a PCDRI corresponding to optical parameter values $\beta_i$ may be constructed such that an RRI received from an individual's eye with optical parameter values $\beta_i$ is identical to or approximates the DRI to within a given degree of accuracy or error. Contextual metadata 1105 (as discussed elsewhere in this specification) may also be input into step 1111 and further used to create a PCDRI.

In exemplary embodiments, the eye of an individual undergoing examination can be modeled as a shift-invariant linear system represented by the PF of Eq. 1. In such embodiments, the relationship between the DRI and the PCDRI can be expressed as:

$$PCDRI=BOTF^{-1}{}_{\beta i}(DRI) \quad (Eq.\ 6)$$

Accordingly, at step 1101, PCDRI is projected onto the individual's retina, and subsequently at step 1102 the RRI is captured and recorded. Next, at step 1103, the DRI and RRI are processed and compared in diagnostics processing step 1103 using known signal processing, statistical analysis, machine learning, or artificial intelligence techniques. In one example, the techniques may include the computation of a statistical distance between the DRI and the RRI. If the difference between the DRI and the RRI (e.g., as measured by a statistical distance) is above a specified or pre-configured threshold, a new set of optical parameter value(s) 1110 is computed. The new set of optical parameter values may be computed based on baseline, expected, or previous optical parameter values and/or known difference measures of prior DRI-RRI pairs. Alternately, if the difference (e.g., statistical difference) between the DRI and RRI is below a specific threshold, the set of optical parameter value(s) 1110 are saved and used to approximate or measure the individual's vision error in terms of vision-related parameters.

In yet another set of embodiments, the method 1100 is used to determine one or more areas of retinal damage or visual impairment. Unlike refractive errors which are generally fixable by usual means, such as prescription glasses or contact lenses, vision impairment (e.g., visual impairment or vision loss) is a decreased ability to see that are not easily addressed with traditional glasses or contact lenses. Vision impairment may be caused by infection, injury or aging of the eye or retinal disorders, for example, and may be directly caused by retinal damage. Vision impairment/retinal damage is often permanent, but typically only affects localized parts of the retina. As an example, macular degeneration or diabetic retinopathy affect central vision while leaving peripheral vision intact. As another example, glaucoma may affect peripheral vision while leaving central vision intact. An impaired ability for an eye to adapt to dark environments (aka night blindness) is another example of a vision impairment.

When diagnosing vision impairment, one or more images are projected onto an individual's retina at step 1101. The retinal image(s) are optionally amplified and captured/recorded with a camera or similar recording device. The retinal image and/or projected image may be further processed (e.g. filtered, scaled, resized, mirrored, manipulated for contrast, color or brightness), and equivalent pixels of both images may be compared (e.g. to identify areas of retinal damage). Individual pixels and/or subsets of pixels are mapped to specific areas of the retina. Equivalent individual pixels or subsets of pixels may for example be analyzed for differences in content, color, brightness and/or contrast. For example, if larger than typical differences in color are observed between certain pixels in the projected image versus the equivalent pixels in the retinal image, it may be determined that the retinal area corresponding to those pixels is damaged. "Larger" may be defined as larger than an absolute threshold, or larger than the majority of the other pixels in the image. "Larger" could also be defined as larger than the average or maximum difference observed for pixels that have deemed to be located in a non-damaged portion of the retina. These are just some examples. Other criteria are also possible.

In another embodiment of the present invention, at least one image is projected on an individual's retina. Two or more corresponding retinal images are captured, corresponding to two or more environmental conditions (e.g. different light levels, different times of day). The retinal images are optionally amplified and captured/recorded with an eye-facing camera or similar eye-facing recording device. The retinal images and/or projected image may be further processed (e.g. filtered, scaled, resized, mirrored, manipulated for contrast, color or brightness). Two or more images may be analyzed and characteristics, such as content, color, brightness and/or contrast may be compared. Comparison of characteristics may be performed at an individual pixel level, averaged over a subset of pixels or averaged over all pixels. Alternatively, only a single retinal image may be captured at a specific environmental condition (e.g. at a low light level) and retinal image, optionally after processing, may be compared against a reference image.

In such embodiments, at step 1102, information describing characteristics of one or more pixels, subsets of pixels, and/or clusters of pixels in the RRI is determined. Said determination may involve an image post-processing step following RRI capture. At step 1103, the DRI or PCDRI is compared to the RRI using known statistical analysis techniques, and locations within the image having significant differences in one or more characteristics can be identified and mapped to corresponding areas on the individual's retina, and provided as outputs 1110. Such locations may be identified as areas where retinal damage is present. Said characteristics may include, but are not limited to, content, color, contrast, brightness, or location of the one or more pixels, subsets of pixels, and/or clusters of pixels. Said statistical analysis techniques may include, at least in part, averaging, computation of standard deviation, minimum, maximum, least square regression, or other known statistical regressions.

Figure 12:
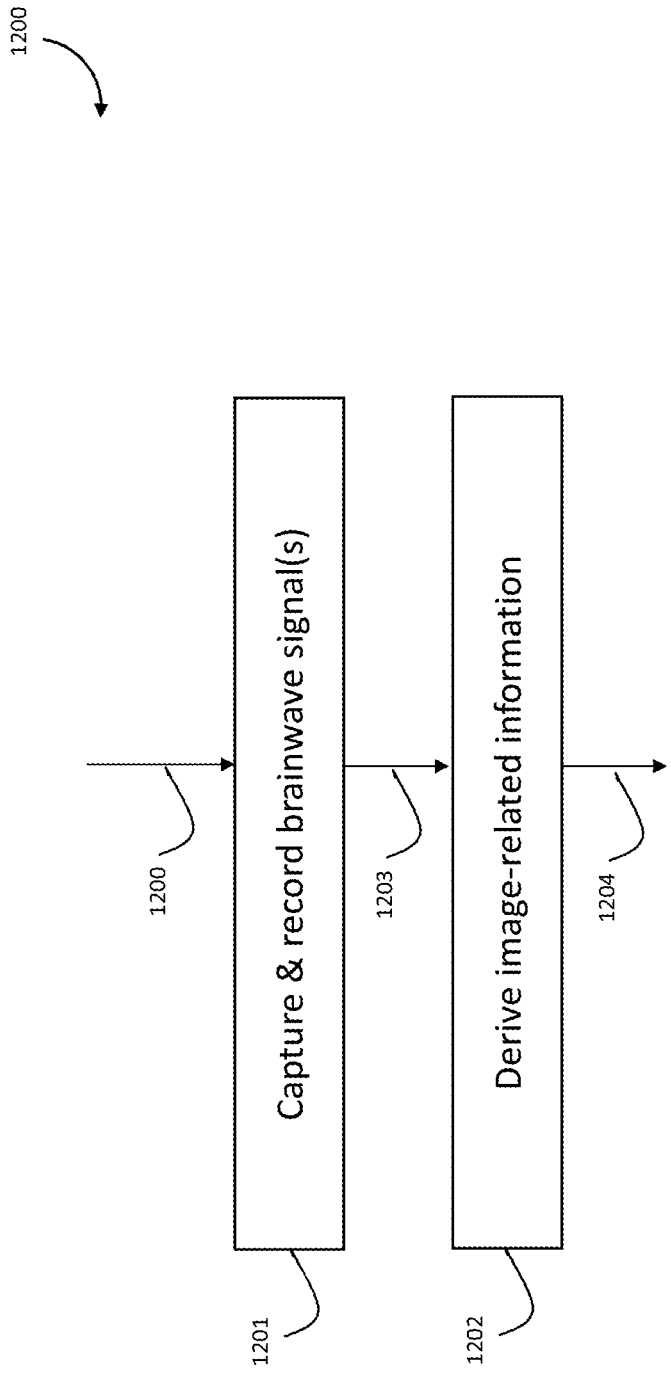

FIG. 12 illustrates aspects and embodiments of a method 1200 for diagnosing vision problems and associated parameters using digital reference images and passive user neural feedback. In certain exemplary embodiments, a brain-computer interface ("BCI") is used to passively obtain visual acuity information. An image or pattern is projected onto an individual's retina, and brain waves are recorded and processed to deduce or approximate the image or pattern received on the retina, or otherwise deduce or approximate information about the image or pattern received on the retina. The projected image or pattern and corresponding deduced retina image/retina image information (obtained via brain wave analysis) may then be processed to deduce visual acuity information without requiring explicit/active user inputs. One or more EEG sensors capable of detecting/measuring brain waves may be positioned throughout the scalp and used for this purpose. Other known sensor types and sensor arrangements for detecting neurological activity (including brain waves) may similarly be used to aid in deducing or approximating the image or pattern received on the retina.

At step 1201, one or more nerve signals received by an individual's light-sensing nerve cells in their retina are captured and recorded using a BCI. Alternatively, or in addition, one or more brain wave signals resulting from nerve signals received by the light-sensing nerve cells in the retina and sent along the optic nerve to the brain are captured and recorded using a BCI. The recorded nerve signal(s) and/or brain wave signal(s) are further processed in step 1202 to deduce information about the image received by the individual's retina. The post-processing at step 1202 may involve, among other things, performing at least a partial reconstruction of the retinal image and/or specific characteristics of said retinal image including reconstructing characteristics of specific pixels of said retinal image. For example, a digital representation of the retinal image may be created by decoding one or more brain wave signals and mapping the information that was encoded in the one or more brain wave signals to one or more characteristics of specific pixels or groups of pixels in the image received by the retina. Such information may include but is not limited to content, brightness, contrast or other related parameters (e.g. RGB value) of one or more pixels, a subset of pixels or a cluster of pixels.

In some embodiments, the methods 900 and 1100 (illustrated in FIG. 9 and FIG. 11, respectively) may be modified to incorporate the method 1200. For example, steps 1201 and/or 1202 may be performed instead of step 902 or instead of step 1101. such that the corresponding methods 900 and 1100 measure the individual's brain wave activity instead of capturing images reflected by individual's retina. Accordingly, the results of step 1202 may be output to step 903 or 1103, respectively, and used to perform the vision diagnostics instead of the RRI. In certain other implementations, the methods 900 or 1100 may be modified to incorporate the method 1200 while continuing to perform step 902 or step 1101, respectively. In such embodiments, both the brain activity of the individual and the RRI are captured and output to diagnostic processing step 903 or 1103, respectively.

When incorporating the method 1200 into the methods 900 or 1100 and performing diagnostic processing at step 903 or step 1103, respectively, the methods may similarly compute a parameterized PF, OTF, or PSF. Alternatively, the methods may compute an optical-to-electrical transfer function (OtETF) that models light received by one or more light-sensing receptors inside the retina to one or more brain wave signals, establishing a relationship between an input image (DRI or PCDRI) and a brain wave signal by considering, among other things, the OTF and/or OtETF to calculate or solve for one or more optical parameter values.

In a variant set of embodiments of the method 1200, rather than reconstructing the retina image from one or more brain wave signals, brain wave signals are processed and analyzed for content that might be related to a projected image. Method 1200 may also implement functions of the system 300 described in FIG. 3, where in such cases, the neurological input 308 is obtained passively by scanning and analyzing brain wave signals. For example, if the projected image contains an eye chart or other text, a user may be asked to read the content of the eye chart or of the text, and one or more brain wave signals may be processed and analyzed to deduce what letters, words or text were decoded by the brain upon reading the text on said projected image. The decoded content (considered passively obtained user neurological input 308) may then be processed, reformatted into a suitable data structure and its content may be compared to a reference data element 306.

In certain embodiments, the systems and the methods of the present invention for diagnosing and/or compensating for an individual's vision problem and associated parameters may include iterative programming and/or steps. For example, an individual may be shown a sequence of PCDRIs. The original DRI may also be shown initially and/or during a sequence of PCDRIs. A system according to one or more embodiments of the present disclosure may obtain visual acuity information for each of the images in the sequence. Visual acuity information of one or more previously displayed images may be taken into account to calculate the value of one or more vision-related parameters used for the creation of a new pre-compensated image in the sequence (e.g., as illustrated by the dotted line in FIG. 1B). In some embodiments, pre-compensated images may be created and stored prior to or at the start of an eye exam.

In other embodiments of the present disclosure, pre-compensated images may be created dynamically (e.g., in real-time or near real-time) as the eye exam is being conducted. Dynamic creation of pre-compensated images may, for example, be desirable if visual acuity information from previously displayed images is used to calculate parameters for one or more subsequent images. For example, the method 150 of FIG. 1B may perform dynamic, successive, and/or iterative creation of pre-compensated images over the course of a vision exam, particularly if one or more contextual metadata change over the course of the eye exam. Other examples are also possible.

In some of these embodiments, collected visual acuity information 158 may be used to determine or modify which image (e.g., DRI/PCDRI) is processed, how an image is processed (e.g. what error pre-compensation parameters are applied), which image is being displayed and/or how an image is being displayed (e.g. for how long, what size, brightness level, contrast level, etc.).

The set of vision-related parameters for the next image to be displayed in such a sequence may be fixed and pre-defined. It is also possible that this set of parameters is based at least in part on additional inputs 161 such as user inputs or other inputs obtained and/or recorded by the system. It is also possible that one of additional input 161 is the current eyewear lens prescription and/or one or more historical eyewear lens prescriptions of the individual undergoing the eye exam. It is also possible that some of the additional inputs 161 are retrieved from a medical record or other patient information management system. It is also possible that the individual undergoing the eye exam is asked to confirm one or more additional inputs before they are used. It is also possible that the individual is asked to consent to one or more additional inputs being used. It is also possible that which pre-compensated images are created/shown and in what order they are created or shown changes dynamically based on visual acuity information obtained from the individual during the conduct of the eye exam.

Images may be shown one at a time, or multiple images may be shown at the same time. All processed images may be shown as part of an eye exam to determine an eyewear lens prescription or only a subset of processed images may be shown. The eye exam procedure may be performed on one eye only, on one eye at a time or on both eyes simultaneously. If only on one eye, the user may be asked to cover or close the other eye. Algorithms may be used to determine which images are shown and in what order.

Various embodiments of the present invention include systems and methods for providing digital vision compensation of a user's field of view or of analog information within a user's field of view of patients with refractive errors and other vision problems. In a preferred set of embodiments, one or more images of a user's field of view or at least a portion of a user's field of view (and/or associated parameters of said one or more images) are sensed and/or processed in real-time (or near real-time). Analog information may be digitally captured, processed (e.g., to compensate for vision-related problems), and projected directly into an individual's field of view, onto an image plane lying within the individual's field of view or projected on an individual's retina. Processed (e.g., to compensate for vision-related problems) information representing or otherwise related to an individual's field of view or to at least a portion of an individual's field of view may alternatively or additionally be emitted by a digital display (e.g., as pixels). Methods described herein may be used to pre-compensate for an individual's known or suspected vision problem(s).

Systems configured to implement automated, digital vision compensation can include one or more electronic devices such as smartphones, laptops, tablets and other consumer electronic devices, electronic (or "smart") swim goggles, ski goggles, windshields, safety glasses, sunglasses, head or eye-mounted eyewear, and A/R or V/R headsets or contact lenses.

The corresponding methods for providing automated, digital vision diagnostics and/or compensation can include one or more of the following steps:
(1) capture image(s) or recording of an individual's field of view,
(2) determine (e.g., based on passive or active feedback in response to one or more projected or displayed DRIs/PCDRIs) and/or access one or more vision problems or vision-related parameter values required for compensation processing,
(3) compute or otherwise access one or more contextual metadata and/or personal information,
(4) manipulate said image(s)/recording to reduce processing power required for subsequent compensation processing and/or file size of image(s)/recording (e.g., based one or more vision problems, vision-related parameter values, contextual metadata, and/or personal information),
(5) process an image(s)/recording to pre-compensate for one or more vision problems, and
(6) display pre-compensated image(s) or recording in real-time or near real-time on the display of an electronic device, or project directly on an individual's retina.

Figure 13:
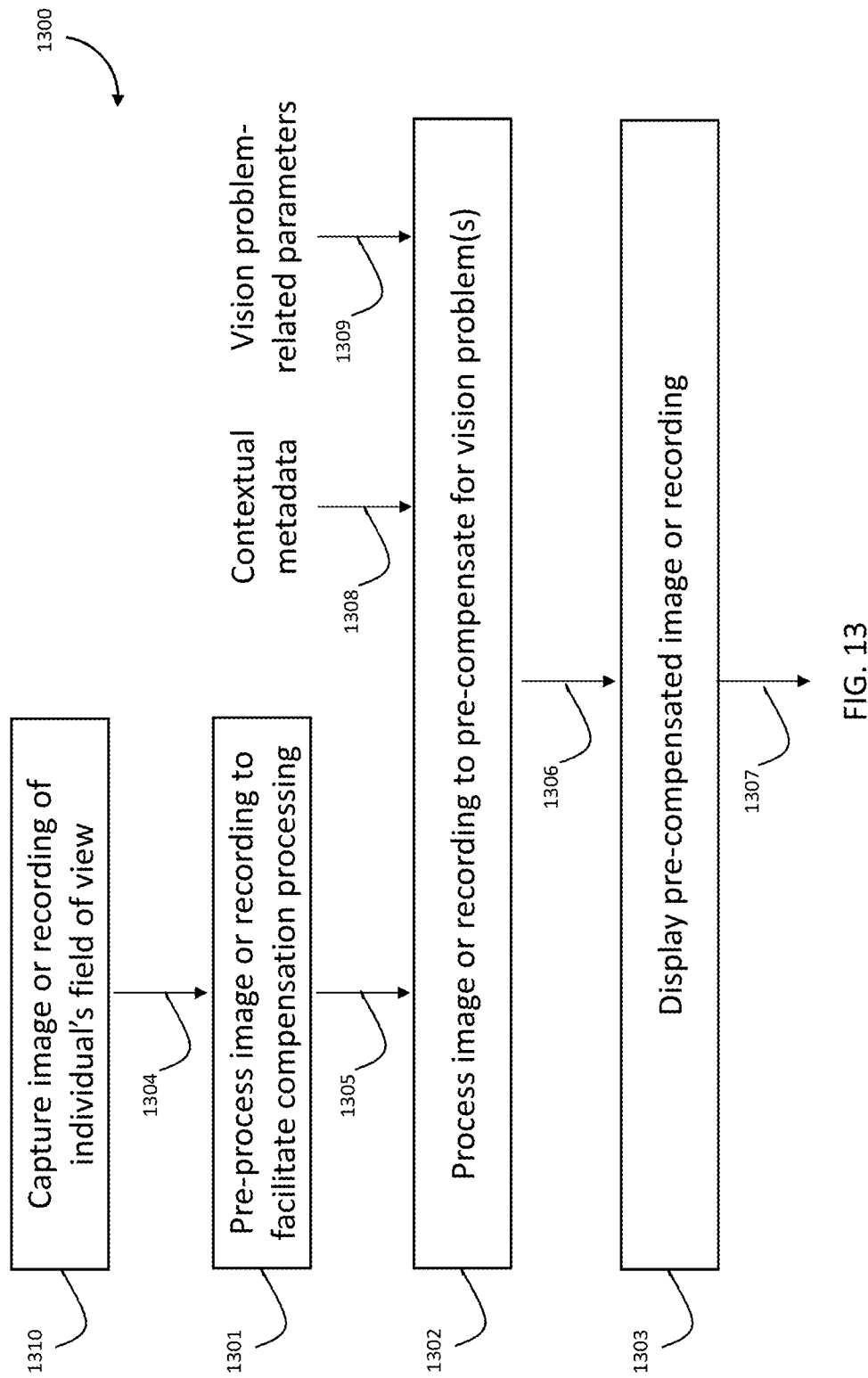
FIG. 13 is a diagram illustrating aspects and embodiments of an image processing system that receives prescription information as an input.

FIG. 13 is a diagram illustrating embodiments of a digital vision problem pre-compensation system, which may be implemented in a digital vision compensation system. The system includes at least one image acquisition unit 1310, which may capture an image(s) or recording of an individual's regular field of view or a portion thereof. In some embodiments, the image(s)/recording may be manipulated by a pre-processing module 1301 prior to being processed by a vision problem compensation module 1302. Pre-processing module 1301 may for example reduce the sampling rate or frame rate, or the resolution of a recording.

Additionally, pre-processing module 1301 may also remove one or more areas of the field of view captured by the image(s)/recording (e.g. the edges). Other pre-processing steps are also possible. Pre-processing may for example be desirable to reduce the computation power required by vision problem compensation module 1302, to reduce the achievable latency or to reduce the amount of memory required to store the recording. In a specific embodiment, pre-processing module 1301 may compare two or more frames of a recording (or all or a subset of pixels of said frames). If it determines, from the comparison, that the two or more frames are sufficiently similar, it may decide to remove one or more of the frames. Two or more frames may be analyzed and characteristics, such as content, color, brightness and/or contrast may be compared. Comparison of characteristics may be performed at an individual pixel level, averaged over a subset of pixels or averaged over all pixels. Deterministic or conventional statistical analysis methods may be used to perform the comparison of the two or more frames. One or more thresholds may be configured and used to determine if a frame can be removed.

In a specific set of embodiments, pre-processing module 1301 may use image recognition algorithms and processes to convert the text content in one or more captured image(s) to a machine-readable data format. Image recognition algorithms and processes may include machine learning, Artificial Intelligence, traditional signal processing or other statistics-based algorithms. Pre-processing module 1301 may use the text in machine-readable data format to create an equivalent digital image or other file format that contains the same or similar content as the original image, but may use different fonts, layout, colors, font sizes, capitalization etc. It may also translate the text content to a different language using a translation engine or machine-readable dictionary. Pre-processing module 1301 may send said equivalent digital image to pre-compensation module 1302 for pre-compensation and display to the individual.

Vision problem pre-compensation module 1302 takes as an input the one or more images or recording captured by image acquisition module 1310 and optionally pre-processed by pre-processing module 1301. Vision problem pre-compensation module 1302 may also take into account one or more contextual metadata 1308. Contextual metadata input 1308 may among other data include the following: distance of display to individual's eye, individual's pupil size, display parameters (e.g. resolution, size, luminance), ambient light level (e.g. room illuminance), and/or other examples referenced throughout this disclosure. Other examples of contextual metadata are also possible. Vision problem pre-compensation module 1302 also takes as an input one or more vision problem parameters 1309. Vision problem-related parameters may for example include one or more parameters of a conventional eyewear prescription (e.g. power, base curve, diameter, brand, cylinder, axis, add prism, acuity, pupillary distance), one or more parameters required to calculate a Point Spread Function ("PSF"), one or more parameters outlining an area of the image or recording (which can for example be mapped to a specific retinal area once projected on the retina), one or more parameters defining a contrast level, and/or other examples of personal information, image parameters, or vision-related parameters referenced throughout this disclosure. Other examples of vision problem-related parameters are also possible.

Pre-compensation module 1302 may interact with an external system to retrieve one or more vision-related parameters. For example, pre-compensation module 1302 may retrieve said information from a medical record, from a patient information management system or from a vision diagnostics system. It is also possible that vision-related parameters are entered manually by the individual, a caregiver, a clinician, an optometrist or another person who has access to said information. It is also possible that one or more vision-related parameters are computed or otherwise derived by diagnostics logic and/or software internal to the pre-compensation system or electronic device housing the pre-compensation system. For example, diagnostics methods described throughout this disclosure may be implemented and housed in the same system or electronic device that implements the components and/or functionality of system 1300. In certain embodiments of the present disclosure, vision-related parameters may be periodically updated. Such updates may be performed automatically and/or based on access to the contents of one or more external databases or APIs (e.g., via a wired or wireless Internet connection).

Pre-compensation module 1302 processes the one or more images or the one or more frames of recording 1305. Processing of an image or frame by pre-compensation module 1302 may include at least in part one or more of the following: filtering, smoothing, image inversion, image mirroring, image rotation, image scaling (amplification or attenuation), image superposition, modifying image color, brightness or contrast, modifying color, brightness or contrast of one or more specific pixels within the image, modifying parameters that correlate with color, brightness or contrast of one or more pixels within the image (e.g. RGB values), applying a brightness or contrast gradient to one, all or a subset of pixels, superimposing color, brightness or contrast information related to one pixel onto one or more other pixels; altering color, brightness or contrast of one or more pixels based on the position or location of said pixel or pixels in the image, calculating a Point Spread Function ("PSF"), resampling, interpolation.

Pre-compensation module 1302 may use statistical analysis methods, machine learning methods and other artificial intelligence methods possibly in combination with one or more processing techniques described above to determine the color, brightness and/or contrast for one or more pixels of the pre-compensated image/recording output 1306. Other processing steps are also possible. Pre-compensation module 1302 may also take into account user input or inputs obtained from one or more ancillary sensors.

Pre-compensation module 1302 may apply other processing steps, not directly related to the individual's specific vision problem to improve readability or visibility. Such processing steps may include but are not limited to amplification, changing or adjusting colors of one or more pixels, changing or adjusting contrast of one or more pixels. Other examples are also possible.

Pre-compensated image(s)/recording 1306 may be shown to the user using display module 1303, via a screen or other display. Alternatively, one or more projectors may be used to project the pre-compensated image(s) or recording on the individual's retina.

In some embodiments, an individual's vision error may be eye specific. For example, one eye may need more correction than the other eye. A vision problem pre-compensation system may create one set of image(s)/recording for a first eye and a second set of image(s)/recording for the second eye. The system may use 2 different cameras or a single camera. A vision problem pre-compensation system may further take as an input one set of vision problem-related parameters for said first eye and another set of vision-related parameters for said second eye. The system may further create two sets of pre-compensated image(s)/recording, one for each eye. The system may further use at least one projector to project the first set of pre-compensated image(s)/recording on the retina of the first eye and at least one other projector to display the second set of pre-compensated image(s)/recording on the retina of the second eye.

In other embodiments, only a single display or projector may be available. In that case, only a single set of vision problem-related parameters, or an average of both sets may be used to generate the pre-compensated image(s)/recording 1306.

In a preferred embodiment of the present invention, the processing by pre-processing module 1301 and pre-compensation module 1302 happens in real-time or in near real-time and there is no noticeable delay to the user.

In a specific set of embodiments, a digital vision pre-compensation system, such as the system 1300, may make adjustments to the configuration settings of the display or projector. For example, it may adjust the screen brightness based on ambient light levels or based on the readability of the content. For example, if the colors or handwriting make an image or recording hard to read, it may increase the screen's brightness.

In another set of embodiments, the system 1300 may store image(s)/recording(s) in memory and access them at a later time. They may also be sent to another external system or device over a network connection. Storing may be controlled by a user command. The image(s)/recording(s) may be machine or user annotated before being recorded. Annotations may apply to image(s)/recording(s) as a whole, to specific frames in a recording and/or to specific subsets of pixels within a frame.

In certain embodiments of the system 1300, a setting or command issued by the user, a caregiver or a local or remote patient management system controls whether or not pre-compensation is enabled. A command can for example be a voice command, a touch command, a gesture, an eye blinking pattern, a signal from an external coupled device, a button push. Other examples are also possible.

In yet another set of embodiments of the system 1300, the individual may be able to interact with the pre-compensated image(s) or recording. Examples of interaction may include a touch or tap, a voice command, gestures, an eye blinking pattern. For example, an individual may use a touch (e.g. pinch) or specific gesture to request that the image(s)/recording be zoomed in or amplified in a specific area. An individual may use touch to select an object displayed in the image(s)/recording. An individual may use a pre-configured eye blinking pattern to store an image(s)/recording or exit out of a certain mode. Other examples of interaction of an individual with the system are also possible, including interaction with the various user interfaces and user feedback mechanisms discussed throughout this disclosure.

Various embodiments of the above systems and methods are capable of compensating for more than one vision problem and automatically adapt compensation based on one or more contextual metadata inputs. For example, an adaptive vision compensation system may take into account the output(s) of an eye tracking module to determine the current focus of an individual. It may further compute or estimate the distance of one or more objects in the individual's field of focus. Based on the estimated distance, it may decide to pre-compensate for either the individual's farsightedness or his/her nearsightedness. In another example, an adaptive vision compensation system may take into account ambient light levels. Based on the ambient light level, it may decide to pre-compensate for night blindness in addition to compensating for the individual's farsightedness or nearsightedness.

In one set of embodiments of a digital image compensation system, the present disclosure is applied to turn a multi-functional mobile consumer electronic device like a smart phone or tablet into a set of reading glasses. For example, an individual could pull out his smart phone, open up his "reading glasses application" with embedded refractive error correction software, hover the camera over the restaurant menu if at a restaurant, or over a food label if at a grocery store, and a digital image of the menu or food label, pre-compensated for the individual's far sightedness or presbyopia, would be displayed on the phone's display.

Rather than pre-compensating the actual captured or recorded image(s), the application may convert the text content in the image(s) to a machine-readable data format. It may use machine learning, Artificial Intelligence or other statistics-based algorithms for the conversion. Using the text in machine-readable data format, it may create an equivalent digital image or other file format that contains the same content as the original image, but may use different fonts, layout, colors, font sizes, capitalization etc. It may also translate the text content to a different language using a translation engine or machine-readable dictionary. The equivalent digital image may be pre-compensated for a user's vision errors before being displayed to the user.

The user may enter one or more vision-related parameters required to perform the digital pre-compensation. Additionally, the application may retrieve one or more vision-related parameters from another application, an external device or an external system such as for example a medical record, a patient management system, an eye care ordering system. It is also possible that software to derive one or more vision-related parameters is built into the application. In specific embodiments, one or more vision-related parameters may be updated periodically (e.g., as part of a vision diagnostic system or process as described throughout this disclosure including the system 100 of FIG. 1A and/or the method 150 of FIG. 1B). This may happen with user intervention (e.g. user enters updated values) or automatically (e.g. through a fully automated background vision diagnostics check or through an API call to an external device or system that may holds updated values).

In various embodiments, such an application may access or compute one or more contextual metadata required to perform the digital pre-compensation operations. The application may access other sensors embedded in the mobile electronic device or coupled to the mobile electronic device to compute said contextual metadata. For example, the application may access the inward-facing (ie user-facing) camera of the mobile electronic device to take one or more images of the user or specific user body parts such as the user's head or eyes. The application may process said one or more images to estimate the distance between the user's eye and the display of the mobile electronic device and/or the user's pupil size. The application may ask the user to provide his/her consent before activating the inward-facing camera. In one specific embodiment, the application may compute an initial estimation of the distance between the user's eye and the device's display using one or more inward-facing cameras. The application may further access the motion sensors built into the mobile electronic device or coupled to the mobile electronic device to track changes in distance between a user's eye and the mobile electronic device. If the distance changes beyond a certain threshold, the application may update the distance parameter used for pre-compensation. The application may also access other sensors such as ambient light sensors to adjust one or more display settings (e.g. brightness) and/or to estimate or compute the user's pupil size.

The application may display one or more pre-compensated image(s)/recording(s) to user. In specific embodiments, the user may interact with the pre-compensated image(s)/recording(s) using methods described elsewhere herein.

Various embodiments of the above systems and methods for providing digital vision compensation may be implemented in whole or in part using some or all of the components found in systems 100 (FIG. 1A), 200 (FIG. 2), 300 (FIG. 3), 400 (FIG. 4), 500 (FIG. 5), 600 (FIG. 6), 700 (FIG. 7), 800 (FIG. 8), and/or 1300 (FIG. 13). Various embodiments may further be implemented in whole or in part using some or all of the steps described in methods 150 (FIG. 1B), 900 (FIG. 9), 1000 (FIG. 10), 1100 (FIG. 11), and/or 1200 (FIG. 12). The systems and methods for providing digital vision compensation may further be implemented alongside automatic vision diagnostic components or functionality described elsewhere in this specification.

Certain embodiments of the present invention further include systems and methods for processing an individual's lens prescription used as an input a signal processing unit and/or software application. These may be implemented as part of the various vision diagnostic and/or vision compensation systems and methods described throughout the present disclosure. If the prescription is for contact lenses, information may include power (aka sphere or strength), base curve, diameter, brand, etc. If the prescription is for eyeglasses information may include power (aka sphere or strength), cylinder, axis, add, prism, base, acuity, pupillary distance, etc. An individual's prescription may also be a set of parameters computed using software-based diagnostic eye exams, such as eye exams that use the signal processing methods described herein.

A patient, caregiver, optometrist, healthcare practitioner or other individual who has access to an individual's lens prescription may manually enter prescription information using an interface available on the electronic device that houses the signal processing unit. Information may also be entered on a different device and sent to the electronic device over a communication link using the radio circuitry, or over a cable or wire that is connected to the electronic device. Prescription information may also be sent automatically or semi-automatically from a diagnostic vision care equipment, from a diagnostic vision care software application, or from a storage unit where the prescription information has been stored.

The processing unit may use this input to determine what processing steps to apply. The processing unit may also use this input to determine the value of one or more variables or parameters used by the signal processing. For example, if signal processing involves an image attenuation, the value of one or more inputs from a prescription may be used to determine the amount of attenuation.

Figure 14:
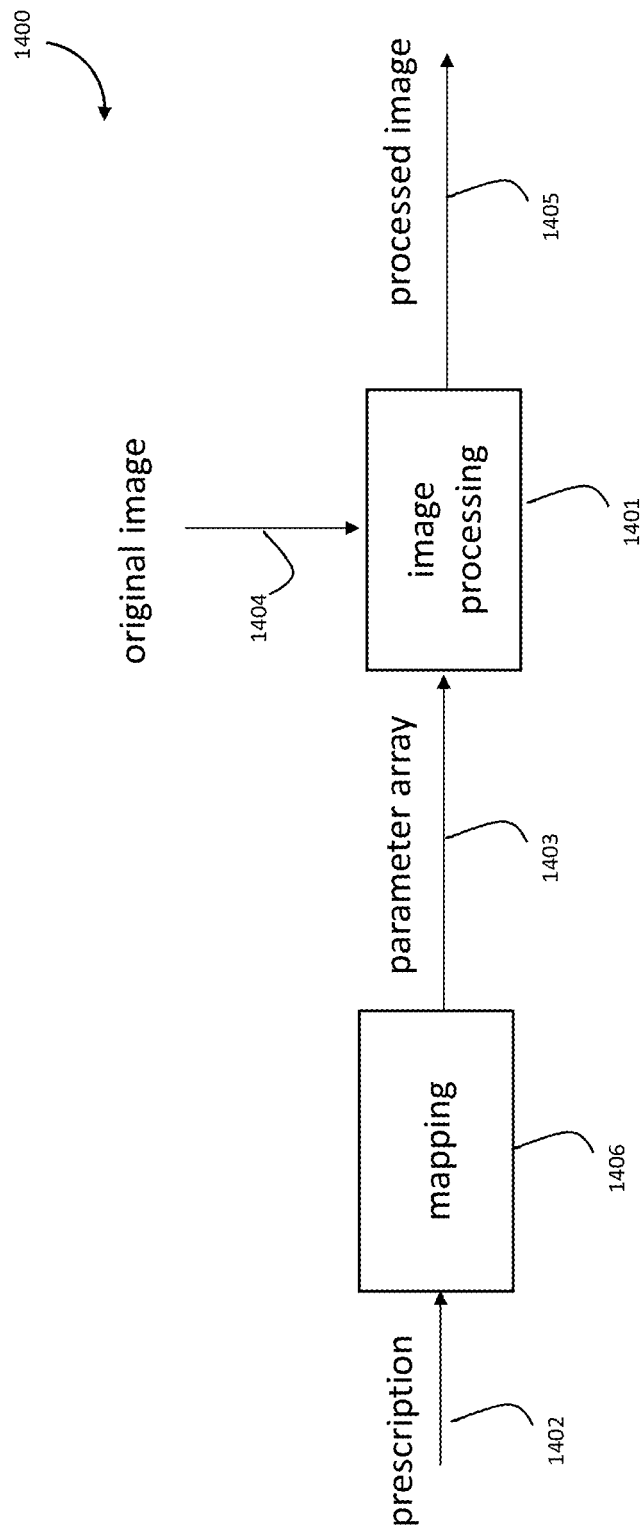
FIG. 14 is a diagram illustrating aspects and embodiments of a system for computing image processing parameters.

FIG. 14 is a diagram illustrating embodiments of a signal processing system 1400 with prescription input 1402. The signal processing system includes at least in part conversion or mapping logic 1406 which maps one or more inputs from prescription input 1402 to one or more variables or parameters in parameter array 1403 used by an image processing unit 1401 to process original image(s) 1404, derivatives of image(s) 1404, or one or more pixels within original image(s) 1404 or derivatives of image(s) 1404.

In one specific embodiment of the invention, the value of a prescription's power may be used to compute a radius or a distance from a center pixel. The radius may be a variable in parameter array 1403. The radius may be used by image processing unit 1401 to define a boundary of an area around a center pixel. Information related to one or more characteristics of a center pixel, such as content, color, brightness and/or contrast of said center pixel, may be used to modify, or may otherwise (in processed or unprocessed format) be superimposed on pixels that fall within the radius. The amount of modification or superposition may vary based on the location of a pixel relative to the center pixel, may vary based on the location of a pixel relative to a distance from the area's boundaries. Other criteria to determine how or how much a pixel is modified with information related to one or more characteristics of the center pixel are also possible. A radius as described above may also be used to define a gradient pattern.

In one specific embodiment of the invention, the sign of a prescription's power may be a parameter in a parameter array 1403. This parameter may be used by image processing unit 1401 to determine if an image scaling step is an image amplification step or an image attenuation step.

In some cases, an individual's lens prescription may be available, and it may be desirable to compute, using at least in part said lens prescription information, one or more image processing parameters that are required to digitally compensate an image for the individual's refractive errors.

Figure 15:
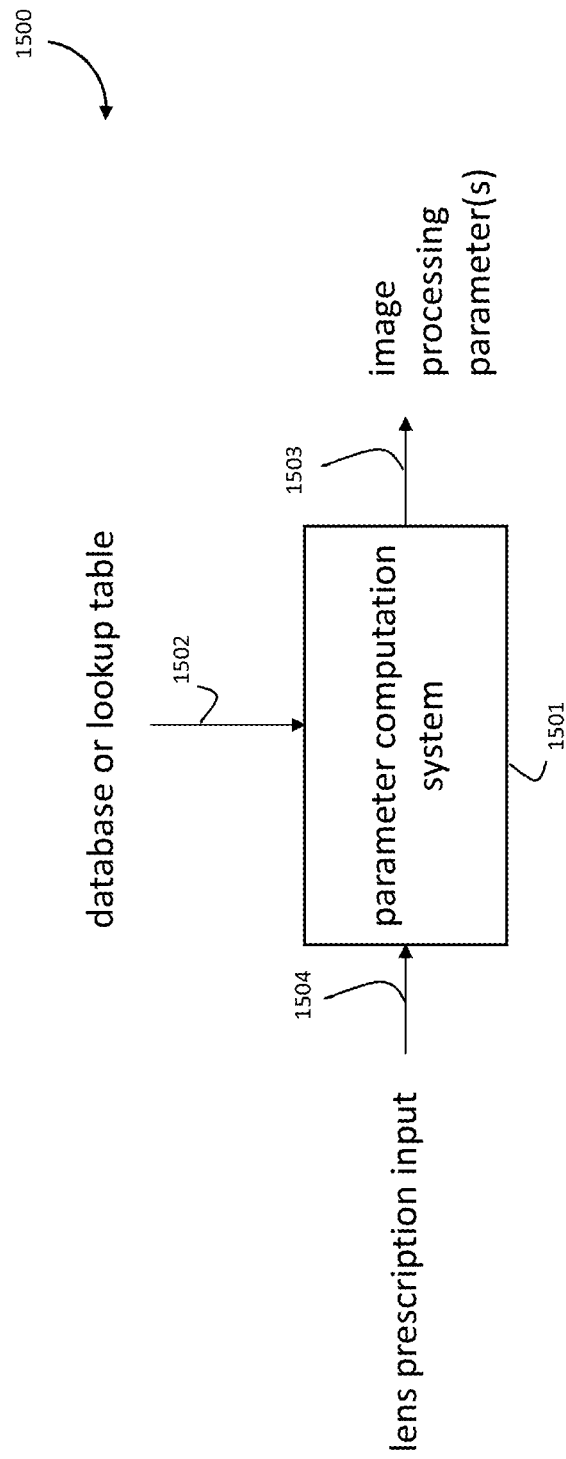
FIG. 15 is a diagram illustrating aspects and embodiments of a parameter computation system in accordance with at least one embodiment of the present disclosure.

FIG. 15 is a diagram illustrating embodiments of a parameter computation system 1500 in accordance with at least one embodiment of the present disclosure. Parameter computation system 1501 takes as inputs lens prescription input 1504 and database or lookup table input 1502. Other inputs, for example the contextual metadata, personal information, passive/active feedback, or other inputs discussed throughout this specification, are also possible inputs 1502. Lens prescription input 1504 may be a structured data input such as a vector, an array or a string. Other data formats are also possible. Parameter computation system 1501 may store lens prescription input 1504 in memory and/or retrieve it from an external source using a communications interface or user interface.

Parameter computation system 1501 may compare a single, a subset or all fields of lens prescription input 1504 against a single, a subset or all corresponding fields of one or more entries in a database or lookup table 1502. Database or look up table input 1502 may at least in part contain one or more of the following fields: lens prescription parameter(s), image processing parameter(s), visual acuity measure(s), metadata input(s), In specific embodiments, not all the above fields may be present. For example, in certain embodiments, only image processing parameter(s) (or a reference to image processing parameters) and one or more lens prescription parameters may be recorded in data records of database or lookup table and provided as an input 1402.

By mapping a single, a subset or all fields of lens prescription input 1504 to a single, a subset or all corresponding fields of one or more entries in the database or look up table input 1502, one or more image processing parameters corresponding to said database record(s) can be associated with lens prescription input 1504 and used to generate image processing parameter output(s) 1503.

Different mapping methods may be used. For example, a mapping method may look for an exact match between one or more fields in lens prescription input 1504 and one or more corresponding fields in one or more data records of database or look up table 1502. Processing methods used by parameter computation system 1501 to determine which entry or entries of database 1502 best match lens prescription input 1504 may include but are not limited to one or more of the following: data manipulation, filtering, interpolation, statistical computing, statistical regression (e.g. least square regression), data compression, and machine learning. In specific embodiments of the present disclosure, processing methods may select more than one database entry, and additional processing steps may be required to determine image processing parameter output(s) 1503. As an example, two database records may be selected and the additional processing may involve averaging, low-pass filtering, statistical regression (e.g. least square regression) and/or interpolation of one or more image processing parameter values for said database records. Image processing parameter outputs 1503 may be a string, a vector, an array. Other structured data formats are also possible.

In another example embodiment, image processing parameters(s), corresponding visual acuity measures, and lens prescription parameters are recorded as data records in database or lookup table and provided as an input 1502. Parameter computation system 1501 compares the fields of lens prescription input 1504 to the corresponding fields in the data records recorded in database and provided as an input 1502, and identifies those data records for which the lens prescription fields match the fields of the lens prescription input are selected. Of all data records with matching prescription fields, the record with the highest visual acuity rating is selected and used to generate outputs 1503. The system 1400 (FIG. 14) may incorporate one or more of the above parameter computation methods.

Various embodiments of the above systems illustrated in FIG. 14 and FIG. 15 may be implemented in whole or in part using some or all of the components found in systems 100 (FIG. 1A), 200 (FIG. 2), 300 (FIG. 3), 400 (FIG. 4), 500 (FIG. 5), 600 (FIG. 6), 700 (FIG. 7), 800 (FIG. 8), and/or 1300 (FIG. 13). Various embodiments may further be implemented in whole or in part using some or all of the steps described in methods 150 (FIG. 1B), 900 (FIG. 9), 1000 (FIG. 10), 1100 (FIG. 11), and/or 1200 (FIG. 12).

Figure 16:
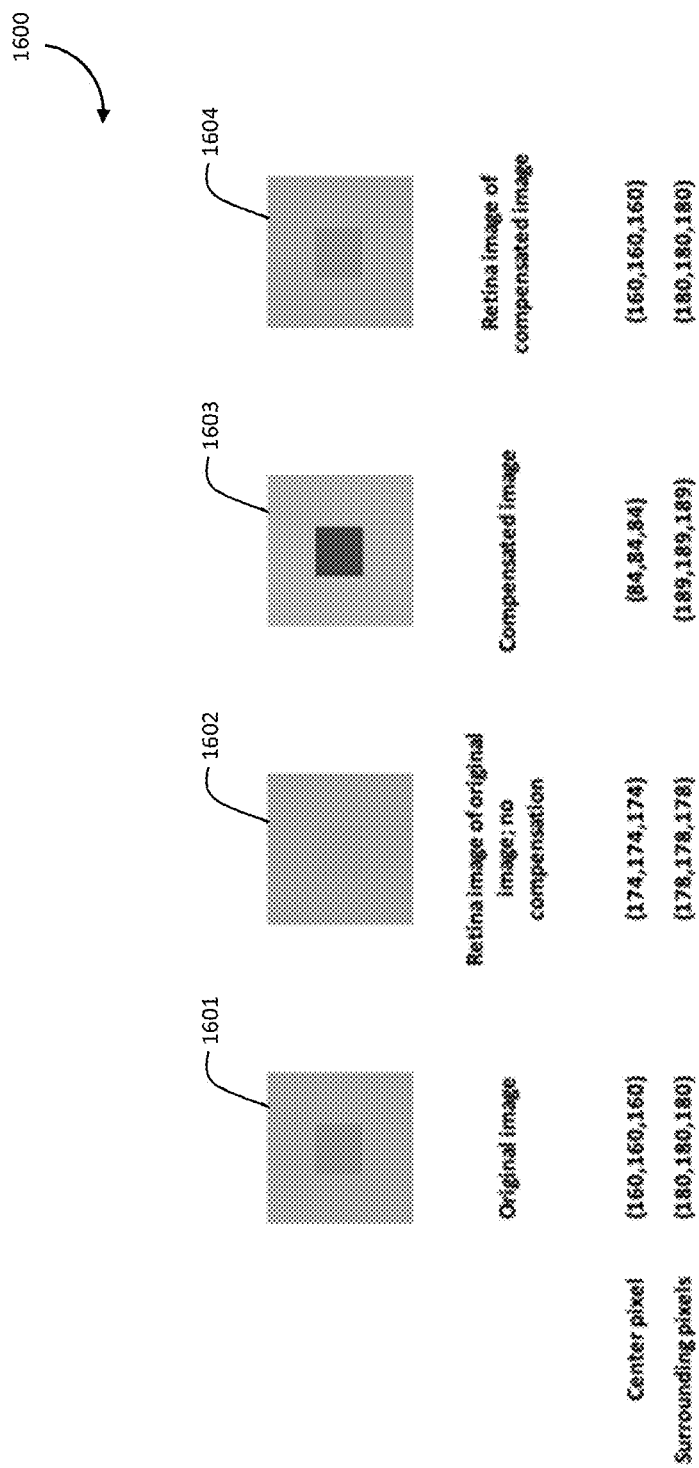
FIG. 16 is a diagram illustrating aspects and embodiments of a system for adapting a digital image to compensate for one or more vision problems and/or vision-related parameters of an individual.

FIG. 16 illustrates aspects and embodiments of a system 1600 for adapting a digital image (e.g., DRI, PCDRI, or other image projected onto or displayed to an individual's retina) to compensate for one or more vision problems and/or vision-related parameters of an individual. In general, the system 1600 can include components (e.g., the electronic device 101 of the system 100 shown in FIG. 1A) capable of performing digital processing for refractive error or vision loss compensation.

In one set of embodiments of the system 1600, a 24-bit LCD display is compensated and includes a plurality of RGB channels with $2^8$ (or 255 using zero-based numbering) gradation levels that are made available per RGB channel. It should be noted that the light-sensitive nerves (aka rods) in human eyes can only distinguish about 150 gradations in brightness, with inter-gradation precision being highest in the mid-range of those gradation levels. It should also be noted that a human's ability to sense differences in colors is even more constrained. Hence, 255 gradation levels is typically sufficient to represent color and brightness digitally. In case of an LCD display that has 10 bits of resolution per RBG channel, up to 1023 gradation values are available per RGB channel.

In a simplified example, a digital image displayed by the LCD display includes a pixel with an RGB value (r1, g1, b1) and is further surrounded by pixels with RGB value (r2, g2, b2). For the purpose of this example, let's assume that r1=g1=b1=X and r2=g2=b2=Y. In this specific example, since the RGB values are identical, the different RGB values represent different level of brightness on a grey scale. Note that the methods described below can easily be extended to situations where the R, G, and/or B values are different, therefore covering the entire color spectrum. It is further assumed that an individual's eye aberrations cause α% of a pixel's RGB value to be projected on each of the eight adjacent pixels that are touching said pixel. The system 1600 can thus calculate the RGB value of the pixels in the digital image that are projected onto the retina as follows:

$$Z=(1-8\alpha)*X+8*\alpha*Y$$

$$W=(1-\alpha)*Y+\alpha*X$$

The system 1600 can further calculate the RGB values, X' and Y' of a compensated digital image such that as the compensated digital image passes through the eye aberrations, the original image is displayed on the retina using the following calculations:

$$X=(1-8\alpha)*X'+8*\alpha*Y'$$

$$Y=(1-\alpha)*Y'+\alpha*X'$$

Or:

$$Y'=[(1-8*\alpha)*Y-\alpha*X]/[(1-\alpha)*(1-8\alpha)-8*\alpha^2]$$

$$X'=Y-(1-\alpha)*Y'$$

The system 1600 illustrates a specific set of examples for performing digital image compensation on an original digital image 1601 (e.g., a DRI) having 3 by 3 pixels. It should be appreciated, however, that this technique can be applied to numerous pixels to analyze RGB values of all or some of pixels in a digital image having an arbitrary number of pixels. In the original digital image, X is chosen to be equal to 160 and Y is chosen to be equal to 180. Thus, in this example the original image 1601 has 20 gradation levels of brightness contrast between the center pixel and the remaining pixels. It is further assumed for the example image 1601 that the pixel leak α as a result of the individual's eye aberrations is equal to 9%.

Image 1602 corresponds to the image projected on the retina in absence of any compensation. In this case, the RGB values of the center pixels are 174 and that of the surrounding pixels is 178. Due to the individual's eye aberrations, the contrast between the pixels is reduced to 4 gradation levels.

Image 1603 shows the compensated digital image (e.g., a PCDRI or image that has been pre-processed to compensate for the individual's eye aberrations according to various embodiments of the present disclosure). The RGB value for the center pixel of the compensated image is 84 and the RGB value of the surrounding pixels in the compensated image is 189. The brightness contrast of the original image has thus been increased to the 105-gradation level as opposed to the 20-gradation level, to compensate for the reduction in contrast caused by the individual's eye aberrations.

Image 1604 shows the projection of the compensated image on the individual's retina after passing through the eye's aberrations. The RGB values of the projected compensated image are 160 and 180 respectively, which matches the brightness contrast in the original image (i.e., a difference of 20 gradation levels). Thus, the focus properties of the original image can be restored, and the eye's refractive error compensated for, using digital compensation achieved using the methods and systems of the present invention.

The above example works particularly well for compensation of images with brightness levels near the center of the RGB range. As brightness levels are close to one or both extremes of the RGB range (e.g., closer to 0 or to 255), compensation capacity can become more limited, for example because it is not possible to create a negative RGB value or an RGB value that exceeds the limit of the display technology of 255 in this example. This issue can be reduced or overcome by using a display with a higher dynamic brightness and/or color range (e.g., a display with 10 or more bits per RGB channel). If the brightness levels are towards one extreme of the RGB gradation range, a shift or centering step can be applied prior to compensation to bring the brightness gradation levels of the image towards the center of the range. It may also be desirable in certain embodiments to add a pre-configured or otherwise deterministic amount to some or all of the R, G, and B values. In various embodiments, it may be preferred to scale some or all of the R, G, and B values up or down by a pre-configured or otherwise deterministic amount. Other techniques including but not limited to filtering, scaling, smoothening are also possible in certain embodiments. It should be noted that the eye's natural ability to distinguish brightness gradation levels near the end of the RGB range is more limited compared to the center of the range.

It is to be appreciated that various embodiments of the above systems for processing digital images (and parameters thereof) to compensate for vision problems, as illustrated in FIG. 16, may be implemented in whole or in part using some or all of the components found in systems 100 (FIG. 1A), 200 (FIG. 2), 300 (FIG. 3), 400 (FIG. 4), 500 (FIG. 5), 600 (FIG. 6), 700 (FIG. 7), 800 (FIG. 8), 1300 (FIG. 13), 1400 (FIG. 14), and/or 1500 (FIG. 15). Various embodiments may further be implemented in whole or in part using some or all of the steps described in methods 150 (FIG. 1B), 900 (FIG. 9), 1000 (FIG. 10), 1100 (FIG. 11), and/or 1200 (FIG. 12).

Various embodiments of the vision diagnostic and/or vision compensations systems and methods discussed in this disclosure may further include or implement one or more cameras built into electronic head-mounted or eye-mounted eyewear that continuously or periodically captures one or images/recording of the eye to monitor an individual's eye(s) for specific characteristics such as for example movement, blinking, color of sclera, level of dryness.

Alternately or in addition, image processing techniques may be applied to analyze one or images to determine the dryness of an individual's eye. Image processing techniques may among other techniques include machine learning or artificial intelligence methods.

In another set of embodiments, image processing techniques are applied to identify an eye blinking pattern or identify changes in eye blinking pattern. Machine learning, Artificial Intelligence, traditional signal processing or other statistical methods may be used to detect an eye blinking pattern or a change in eye blinking pattern. Specific eye blinking patterns or changes in eye blinking patterns may be used to infer a health condition, a behavioral or emotional state or a change in health condition, behavioral or emotional state such as fatigue, stress, boredom, sadness, joy, anxiety etc. Detection of an eye blinking pattern or change in eye blinking pattern may trigger an action. An action may be a user-initiated command (whereby the user initiation happens by means of eye blinking), an automated outreach to a caregiver or medical response system, a suspension of an electronic device or application, a change in settings of an external but coupled electronic device such as for example dimming of lights, turning up volume, changing genre of music played). Other examples are also possible.

In specific embodiments of the present disclosure, an activity or behavior an individual is engaged in (e.g. gaming, watching a video, daydreaming, driving) can be inferred by monitoring and analyzing one or more characteristics or changes in one or more characteristics of the individual's eye.

In an exemplary set of embodiments, an individual may focus on/stare at an object and/or text in the individual's field of view. An eye monitoring system embedded in electronic eyewear or in another electronic device with a user-facing camera automatically detects a focus is happening and identifies the object/text/person on which the individual is focused. Eye monitoring and feedback system may signal this information to an image processing and display unit. Said image processing unit may take action based on received signal. For example, it may zoom in on the object/text, it may create an equivalent digital image of the text with same or similar content but different font, size, color etc, it may identify the object/person or characteristics of the object/person and annotate an image with said identification information.

Various embodiments and examples in this disclosure describe systems and methods for performing vision diagnostics and/or compensation with reference to the an "eye" or "retina" of an individual. It should be appreciated that in certain embodiments, vision diagnostic or compensation techniques may be performed on both of an individual's eyes simultaneously or sequentially to provide specific diagnoses or compensations for each eye individually and/or both eyes collectively. In certain embodiments, for example, where an individual's visual acuity or refractive error varies between eyes, it may be appropriate to calculate a diagnosis and/or provide compensation that reflects the individual's collective visual capabilities as perceived by both eyes simultaneously.

The figures and the description in this disclosure relate to preferred embodiments by way of illustration only. It should be noted that from the discussion, alternative embodiments of the structures and methods disclosed herein will be readily recognized as viable alternatives that may be employed without departing from the principles of what is claimed.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An electronic eyewear system for compensating for an individual's vision problem, the system comprising:
   a screen configured to display from a first image plane a reference image within a field of view of an individual, the reference image moving from the first optical plane to the individual's retina along a first optical path having a first optical path length, and having a first angle of incidence at the retina relative to the central axis of the individual's field of view;
   a sensor configured to record at a second image plane a recorded image based on said reference image as processed by the individual's retina, the recorded image moving from the individuals' retina to the second optical plane along a second optical path having a second optical path length, and having a second angle of incidence at the retina relative to the central axis of the individual's field of view;
   at least one processor communicatively coupled to the screen and the sensor, said processor configured to:
      calculate an inverse optical transfer function by comparing the reference image at the first optical plane to the recorded image at the second optical plane;
      wherein the inverse optical transfer function is based in part on at least one of a difference between the first optical path length and the second optical path length and a difference between the first angle of incidence and the second angle of incidence;
      create a pre-compensated reference image by using the inverse optical transfer function; and
      cause the screen to display the pre-compensated reference image.

2. The electronic eyewear system of claim 1, wherein the processor is additionally configured to receive a captured image, create a pre-compensated captured image by using the inverse optical transfer function, and cause the screen to display the pre-compensated captured image.

3. The electronic eyewear system of claim 2, wherein the screen is a backlit digital display.

4. The electronic eyewear system of claim 2, wherein the screen further comprises an image projector configured to project the pre-compensated captured image onto the first image plane.

5. The electronic eyewear system of claim 2, wherein the screen further comprises an image projector configured to project the pre-compensated captured image directly onto the retina.

6. The electronic eyewear system of claim 2, wherein the pre-compensated captured image is displayed in real-time or near real-time following the capture of the reference image.

7. The electronic eyewear system of claim 1, wherein the recorded image is based at least in part on a reflected retinal image of the individual.

8. A handheld integrated electronic device for passively determining an error value of an optical parameter of an individual's vision, comprising:
   (A) a screen for displaying at a first image plane digital reference images to an individual's retina;
   (B) a sensor for capturing at a second image plane recorded images of the individual's retina as the retina is processing said digital reference images;
   (C) a processor configured to
      (A) obtain the digital reference images,
      (B) project the digital reference images from the first image plane on to a retina via a first optical path having a first length and a first angle of incidence relative to the central axis of the individual's field of view,
      (C) receive a reflected image from the retina at a second image plane via a second optical path having a second length and a second angle of incidence relative to the central axis of the individual's field of view,
      (D) model, by comparing the digital reference image to the reflected image, an optical transfer function comprising one or more optical parameters, the optics between the first image plane and the retina along the first optical path, the optics associated with absorption or reflection of light at the retina, and the optics between the retina and the second image plane along the second optical path, the difference between the first length and the second length, and the difference between the first angle and the second angle; and
      (E) calculate at least in part based on the optical transfer function an error value for one of the optical parameters; and,
   (D) a memory for storing the error value for communication from or display on the integrated device.

9. The device of claim 8, wherein the processor is further configured to transmit to the screen a signal that causes an adjustment of a displayed image, wherein said adjustment is based at least in part on the error value of the one of the optical parameters.

10. The device of claim 8, wherein the processor is further configured to determine a value of a prescription parameter, for correction of a vision error, based at least in part on the calculated error value of the one of the optical parameters.

11. The device of claim 10, wherein the processor is further configured to transmit to the screen, a signal that causes an adjustment of a displayed image, wherein said adjustment is based at least in part on the determined value of the prescription parameter.

12. The device of claim 8, wherein the processor is further configured to:
   (F) generate a pre-compensated digital reference image based on the calculated error value of the one of the optical parameters; and
   (G) repeat steps (A) through (F) iteratively, using the pre-compensated digital reference image from step (F) in place of the digital reference image in steps (A) and (B), until the calculated error value of the one of the optical parameters is below a threshold.

13. The device of claim 12, wherein the processor is further configured to determine a value of a prescription parameter, for correction of a vision error, based at least in part on the calculated error value of the one of the optical parameters after said calculated error value is below said threshold.

14. The device of claim 13, wherein the processor is further configured to transmit to the screen a signal that causes an adjustment of a displayed image, wherein said adjustment is based at least in part on the calculated error value of the one of the optical parameters after said calculated error value is below said threshold.

15. The device of claim 14, wherein the adjustment is any one of brightness, contrast, or color associated with at least one pixel in the displayed image.

16. The device of claim 8, wherein the second optical path is the same as the first optical path.

17. The device of claim 9, 11 or 14 wherein the display is integrated in an eyewear device.

18. The device of claim 9, 11 or 14 wherein the display is integrated in a smartphone.

19. A method for passively determining optical information associated with the vision of a person, comprising:
   (A) obtaining a digital reference image;
   (B) projecting the digital reference image from a first image plane via a first optical axis, on to a retina;
   (C) recording a digital representation of the neurological image sensed by the person via at least one brain-computer interface, wherein the neurological image is associated with one or more nerve signals received by the light-sensing nerve cells when that person's retina detects the digital reference image;
   (D) modeling using an optical transfer function comprising one or more optical parameters, the optics between the first image plane and the retina along the first optical axis; and
   (E) comparing the digital reference image to the digital representation of the neurological image to calculate an error value for one of the optical parameters.

20. The method of claim 19, further comprising transmitting to a display, a signal that causes an adjustment of a displayed image generated by the display, wherein said adjustment is based at least in part on the calculated error value of the one of the optical parameters.

21. The method of claim 19, further comprising determining a value of a prescription parameter, for correction of a vision error, based at least in part on the calculated error value of the one of the optical parameters.

22. The method of claim 21, further comprising transmitting to a display a signal that causes an adjustment of a displayed image generated by the display, wherein said adjustment is based at least in part on the determined value of the prescription parameter.

23. The method of claim 19, further comprising:
   (G) generating a pre-compensated digital reference image based on the calculated error value of the one of the optical parameters; and
   (H) repeating steps (A) through (F) iteratively, using the pre-compensated digital reference image from step (G) in place of the digital reference image in steps (A) and (B), until the calculated error value of the one of the optical parameters is below a threshold.

24. The method of claim 23, further comprising determining a value of a prescription parameter, for correction of a vision error, based at least in part on the calculated error value of the one of the optical parameters after said calculated error value is below said threshold.

25. The method of claim 24, further comprising transmitting to a display a signal that causes an adjustment of a displayed image generated by the display, wherein said adjustment is based at least in part on the calculated error value of the one of the optical parameters after said calculated error value is below said threshold.

26. The method of claim 25, wherein the adjustment is any one of brightness, contrast, or color associated with at least one pixel in the displayed image.

27. The method of claim 19, wherein the second optical axis is the same as the first optical axis.

28. The method of claim 20, 22 or 25 wherein the display is integrated in an eyewear device.

29. The method of claim 20, 22 or 25 wherein the display is integrated in a smartphone.

* * * * *